(12) United States Patent
Gajewski et al.

(10) Patent No.: US 7,750,184 B2
(45) Date of Patent: Jul. 6, 2010

(54) VITAMIN D RECEPTOR MODULATORS

(75) Inventors: Robert Peter Gajewski, Indianapolis, IN (US); Charles David Jones, Indianapolis, IN (US); Jared Harris Linebarger, Indianapolis, IN (US); Jianliang Lu, Fishers, IN (US); Tianwei Ma, Carmel, IN (US); Sunil Nagpal, Carmel, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 919 days.

(21) Appl. No.: 10/577,967

(22) PCT Filed: Nov. 8, 2004

(86) PCT No.: PCT/US2004/035513
§ 371 (c)(1),
(2), (4) Date: May 2, 2006

(87) PCT Pub. No.: WO2005/051898
PCT Pub. Date: Jun. 9, 2005

(65) Prior Publication Data
US 2006/0293385 A1 Dec. 28, 2006

Related U.S. Application Data

(60) Provisional application No. 60/523,878, filed on Nov. 20, 2003.

(51) Int. Cl.
*C07C 303/00* (2006.01)
*C07C 305/00* (2006.01)
*A01N 41/06* (2006.01)

(52) U.S. Cl. .......................... 564/84; 558/37; 514/601

(58) Field of Classification Search .................. None
See application file for complete search history.

(56) References Cited

U.S. PATENT DOCUMENTS

| | | | |
|---|---|---|---|
| 6,218,430 | B1 | 4/2001 | Allegretto et al. |
| 6,706,725 | B1 | 3/2004 | Bernardon |
| 2006/0094778 | A1 | 5/2006 | Nagpal et al. |
| 2006/0135484 | A1 | 6/2006 | Nagpal et al. |
| 2006/0287536 | A1 | 12/2006 | Dahnke et al. |
| 2009/0018058 | A1* | 1/2009 | Bunel et al. ............... 514/12 |

FOREIGN PATENT DOCUMENTS

| | | |
|---|---|---|
| WO | WO 03/101978 | 12/2003 |
| WO | WO 2004/048309 A | 6/2004 |
| WO | WO 2005/051893 | 6/2005 |
| WO | WO 2005/051936 | 6/2005 |
| WO | WO 2005/051938 | 6/2005 |
| WO | WO 2005/051940 | 6/2005 |
| WO | WO 2006/069153 | 6/2006 |
| WO | WO 2006/069154 | 6/2006 |

OTHER PUBLICATIONS

CAS online citation 2004:467841 [retrieved Mar. 16, 2009] from STN; Columbus OH, USA.*

Basak, et al., "Comparative effects of calcipotriol and betamethasone 17-valerate solution in the treatment of seborrhoeic dermatitis of the scalp," *European Academy of Dermatology and Venereology JEADV*, vol. 15, pp. 77-92 (2001).

Böhm, et al., "Disseminated superficial actinic porokeratosis: Treatment with topical tacalcitol," *Journal of the American Academy of Dermatology*, vol. 40, pp. 479-480 (1999).

Cunningham, et al., "Topical calcipotriene for morphea/linear scleroderma," *Journal of the American Academy of Dermatology*, vol. 39, pp. 211-215 (1998).

Harrison, "Disseminated superficial actinic porokeratosis responding to calcipotriol," *Clinical Exp. Dermatol.*, vol. 19, No. 1, p. 95 (1994).

Lin, et al., "The pleiotropic actions of vitamin D," *BioEssays*, vol. 26, pp. 21-28 (2003).

Nakayama, et al., "Four cases of sebopsoriasis or seborrheic dermatitis of the face and scalp successfully treated with 1a-24(R)-dihydroxycholecalciferol (tacalcitol) cream," *European Journal of Dermatology*, vol. 10, No. 7, pp. 528-532, (2000).

Sapadin, et al., "Treatment of Scleroderma," *Arch Dermatology*, vol. 138, pp. 99-105 (2002).

Sato, et al., "Epidermal Growth Factor and 1α,25-Dihydroxyvitamin $D_3$ Suppress Kipogenesis in Hamster Sebaceous Gland Cells In Vitro," *The Society of Investigative Dermatology*, vol. 117, pp. 965-970 (2001).

Zinser, et al., "Vitamin $D_3$ receptor ablation sensitizes skin to chemically induced tumorigenesis," *Carcinogenesis*, vol. 23, No. 12, pp. 2103-2109 (2002).

Masahiko Inouye, Toshiyuki Miyake, Masaru Furusyo, Hiroyuki Nakazumi: "Molecular recognition of beta-Ribofuranosides by synthetic polypyridine_macrocyclic receptors" J.Am. Chem. Soc. vol. 117, 1995, pp. 12416-12425, XP001206518.

Ping Huang, John Ramphal, James Wei, Congxin Liang, Bahija Jallal, Gerald McMahon and Cho Tang: "Structure-based design and discovery of novel inhibitors of protein tyrosine phosphatases" Bioorganic & Medicinal Chemistry, vol. 11, 2003, pp. 1835-1849, XP001206517.

Nagpal, S. et al. "Vitamin D Analogs: Mechanism of Action of Therapeutic Applications", *Curr. Med. Chem.* 2001, 1661-1679, vol. 8.

Boehm, M., "Novel Nonsecosteroidal Vitamin D Mimics Exert VDR-modulating Activities" *Chemistry & Biology*, 1999, 265-275, vol. 6(5).

Bouillon R., et al. Endocrine Rev. 1995, 200-257, vol. 16.

Swann et al. "Rational Design of Vitamin D3 Analogues Which Selectively Restore Activity to a Vitamin D Receptor Mutant Associated with Rickets" *Org. Lett.* 2002, p. 1863-3866 vol. 4.

Swann et al. "Structure-Based Design of Selective Agonists for a Rickets-Associated Mutant of the Vitamin D Receptor" *J. Am. Chem. Soc.* 2002 13795-13805, vol. 124.

* cited by examiner

*Primary Examiner*—Karl J Puttlitz
(74) *Attorney, Agent, or Firm*—James B. Myers

(57) ABSTRACT

The present invention relates to novel, non-secosteroidal, sulfonate and sulfonamide functional diaryl compounds with vitamin D receptor (VDR) modulating activity that are less hypercalcemic than 1α,25 dihydroxy vitamin D3. These compounds are useful for treating bone disease and psoriasis.

19 Claims, No Drawings

VITAMIN D RECEPTOR MODULATORS

This application is submitted as a United States national phase entry, pursuant to 35 U.S.C. §371, of PCT/US2004/035513, filed on 8 Nov. 2004, which claims the benefit of U.S. provisional patent application Ser. No. 60/523,878, filed 20 Nov. 2003, which is incorporated by reference herein.

BACKGROUND OF THE INVENTION

Vitamin $D_3$ Receptor (VDR) is a ligand dependent transcription factor that belongs to the superfamily of nuclear hormone receptors. The VDR protein is 427 amino acids, with a molecular weight of ~50 kDa. The VDR ligand, 1α,25-dihydroxyvitamin D3 (the hormonally active form of Vitamin D) has its action mediated by its interaction with the nuclear receptor known as Vitamin D receptor ("VDR"). The VDR ligand, 1α,25-dihydroxyvitamin D3 (1α,25(OH)$_2$D$_3$) acts upon a wide variety of tissues and cells both related to and unrelated to calcium and phosphate homeostasis.

The activity 1α,25-dihydroxyvitamin D3 in various systems suggests wide clinical applications. However, use of conventional VDR ligands is hampered by their associated toxicity, namely hypercalcemia (elevated serum calcium). Currently, 1α,25(OH)$_2$D$_3$, marketed as Rocaltrol® pharmaceutical agent (product of Hoffmann-La Roche), is administered to kidney failure patients undergoing chronic kidney dialysis to treat hypocalcemia and the resultant metabolic bone disease. Other therapeutic agents, such as Calcipotriol® (synthetic analog of 1α,25(OH)$_2$D$_3$) show increased separation of binding affinity on VDR from hypercalcemic activity.

Recently, chemical modifications of 1α,25(OH)$_2$D$_3$ have yielded analogs with attenuated calcium mobilization effects (R. Bouillon et. al., Endocrine Rev. 1995, 16, 200-257). One such analog, Dovonex® pharmaceutical agent (product of Bristol-Meyers Squibb Co.), is currently used in Europe and the United States as a topical treatment for mild to moderate psoriasis (K. Kragballe et. al., Br. J. Dermatol. 1988, 119, 223-230).

Other Vitamin $D_3$ mimics have been described in the publication, *Vitamin D Analogs: Mechanism of Action of Therapeutic Applications*, by Nagpal, S.; Lu, J.; Boehm, M. F., Curr. Med. Chem. 2001, 8, 1661-1679.

Although some degree of separation between the beneficial action and calcium raising (calcemic) effects has been achieved with these VDR ligands, to date the separation has been insufficient to allow for oral administration to treat conditions such as osteoporosis, cancers, leukemias, and severe psoriasis.

One example of a major class of disorder that could benefit from VDR mediated biological efficacy in the absence of hypercalcemia is osteoporosis. Osteoporosis is a systemic disorder characterized by decreased bone mass and microarchitectural deterioration of bone tissue leading to bone fragility and increased susceptibility to fractures of the hip, spine, and wrist (World Health Organization WHO 1994). Osteoporosis affects an estimated 75 million people in the United States, Europe, and Japan.

Within the past few years, several antiresorptive therapies have been introduced. These include bisphosphonates, hormone replacement therapy (HRT), a selective estrogen receptor modulator (SERM), and calcitonins. These treatments reduce bone resorption, bone formation, and increase bone density. However, none of these treatments increase true bone volume nor can they restore lost bone architecture.

Synthetic VDR ligands with reduced calcemic potential have been synthesized. For example, a class of bis-phenyl compounds stated to mimic 1α,25-dihydroxyvitamin $D_3$ is described in U.S. Pat. No. 6,218,430 and the article; "Novel nonsecosteroidal vitamin D mimics exert VDR-modulating activities with less calcium mobilization than 1α,25-Dihydroxyvitamin $D_3$" by Marcus F. Boehm, et. al., *Chemistry & Biology* 1999, Vol 6, No. 5, pgs. 265-275.

Synthetic VDR ligands having an aryl-thiophene nucleus are described in U.S. provisional patent application Ser. No. 60/384,151, filed 29 May 2002.

There remains a need for improved treatments using alternative or improved pharmaceutical agents that mimic 1α,25 (OH)$_2$D$_3$ to stimulate bone formation, restore bone quality, and treat other diseases without the attendant disadvantage of hypercalcemia.

SUMMARY OF THE INVENTION

Novel compounds having a nucleus of formula "(AA)" have been found effective as Vitamin D Receptor (VDR) modulators:

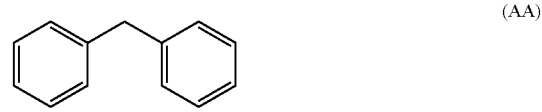

(AA)

The compounds of the invention with VDR modulating activities are represented by formula (I)

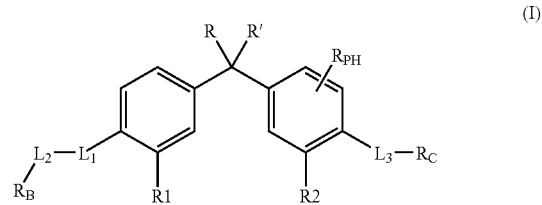

(I)

wherein the variables R, R', R1, R2, $R_{PH}$, $L_1$, $L_2$, $L_3$, $R_B$ and $R_C$ are as hereinafter defined. It is a discovery of this invention that compounds described herein display the desirable cell differentiation and antiproliferative effects of 1,25(OH)$_2$D$_3$ with reduced calcium mobilization (calcemic) effects if substituent $R_C$ possesses a sulfonate or sulfonamide substituent.

In another aspect, the present invention is directed towards pharmaceutical compositions containing pharmaceutically effective amounts of compound of the invention or a pharmaceutically acceptable salt or prodrug thereof, either singly or in combination, together with pharmaceutically acceptable carriers and/or auxiliary agents.

Another aspect of the invention is a pharmaceutical formulation for treatment or prevention of osteoporosis containing pharmaceutically effective amounts of the vitamin D receptor modulator compound of the invention together with pharmaceutically effective amounts of co-agents conventionally used for the treatment of osteoporosis.

Another aspect of the invention is a pharmaceutical formulation for treatment or prevention of psoriasis containing pharmaceutically effective amounts of the vitamin D receptor modulator compound of the invention together with pharmaceutically effective amounts of co-agents conventionally used for the treatment of psoriasis.

Another aspect of the invention is to use the compounds of the invention to treat disease states responsive to Vitamin D receptor ligands.

Another aspect of the invention is the prevention and treatment of acne, actinic keratosis, alopecia, Alzheimer's disease, autoimmune induced diabetes, bone fracture healing, breast cancer, Crohn's disease, prostate cancer, benign prostatic hyperplasia, bladder cancer, colon cancer, Type I diabetes, host-graft rejection, hypercalcemia, Type II diabetes, leukemia, multiple sclerosis, insufficient sebum secretion, osteomalacia, osteoporosis, insufficient dermal firmness, insufficient dermal hydration, myelodysplastic syndrome, psoriatic arthritis, psoriasis, renal osteodystrophy, rheumatoid arthritis, scieroderma, seborrheic dermatitis, skin cancer, systemic lupus erythematosis, skin cell damage from Mustard vesicants, ulcerative colitis and wrinkles; by administering to a mammal in need thereof a pharmaceutically effective amount of a compound of the invention.

DETAILED DESCRIPTION OF THE INVENTION

Definitions

The term, "abscess" refers to adverse complications often associated with surgery, trama, or diseases that predispose the host to abscess formation from encapsulated bacteria lymphocytes, macrophages, and etc.

The term, "adhesion" refers to the adverse and abnormal union of surfaces normally separate by the formation of new fibrous tissue resulting from an inflammatory process.

The term, "compound(s) of the invention" refers to one (or a plurality) of compounds described by Formulae I, II, or III or included in Tables 1, 2, or 3 or described in structural formulae A thru R or any of the compounds prepared as products in the Schemes or Examples set out herein.

The term, "Active Ingredient" means a compound of the invention.

The term, "Mustard" is inclusive of both sulfur mustards and nitrogen mustards, either alone or in any combnation. Examplary of such compounds are the vesicants; bis(2-chloroethyl)sulfide (Chemical Agent Symbol HD), $Cl(CH_2)_2S(CH_2)_2Cl$ 1,2-bis(2-chloroethylthio)ethane (Chemical Agent Symbol Q), $Cl(CH_2)_2S(CH_2)_2S(CH_2)_2Cl$; bis(2-chloroethylthioethyl)ether, $Cl(CH_2)_2S(CH_2)_2O(CH_2)_2S(CH_2)_2Cl$ (Chemical Agent Symbol T); tris(2-chloroethyl)amine (Chemical Agent Symbol HN3) $N(CH_2CH_2Cl)_3$; N-methyl-2,2'-dichlorodiethylamine (Chemical Agent Symbol NH2); and 2,2'-dichlorotriethylamine, $CH_3CH_2N(CH_2CH_2Cl)_2$ (Chemical Agent Symbol NH1).

The term, "(Acidic Group)" means an organic group that acts as a proton donor capable of hydrogen bonding. Illustrative of an (Acidic Group) is a group selected from the following:

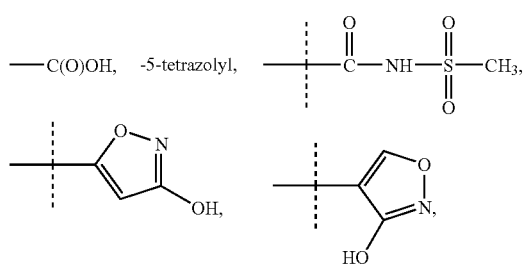

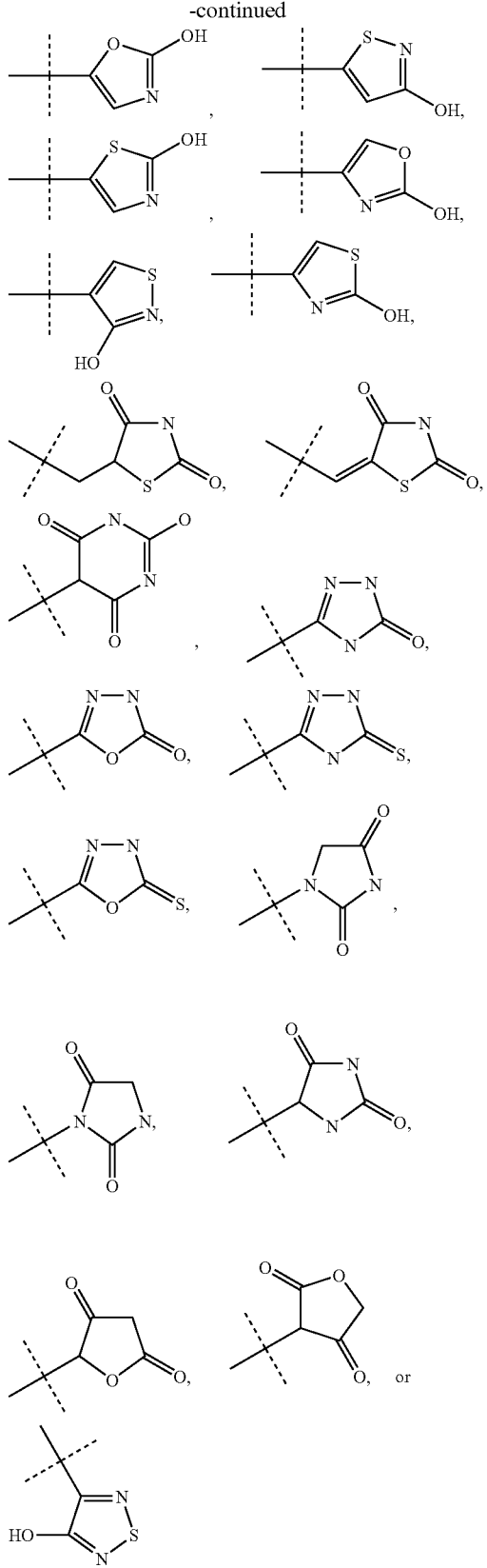

The term, "–1,3-thiazolidine-2,4-dione-5-ethtylidene", refers to the radical represented by the structural formula:

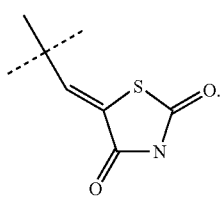

The term, "—CH₂—C(O)—N-pyrrolidine" refers to the radical represented by the structural formula:

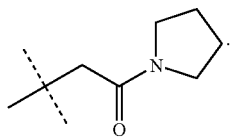

The term, "—CH₂—N-pyrrolidin-2-one" refers to the radical represented by the structural formula:

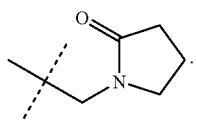

The term, "—CH₂-(1-methylpyrrolidin-2-one-3-yl)" refers to the organic radical represented by the structural formula:

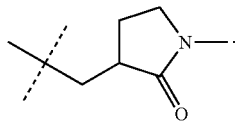

The term, "1,3,4-oxadiazolin-2-one-5-yl" refers to the organic radical represented by the structural formula:

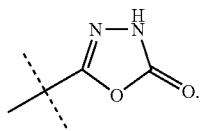

The term, "1,3,4-oxadiazolin-2-thione-5-yl" refers to the organic radical represented by the structural formula:

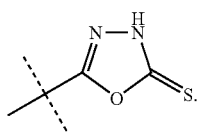

The terml, "imidazolidine-2,4-dione-5-yl" refers to the organic radical represented by the structural formula:

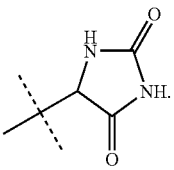

The term, "isoxazol-3-ol-5-yl" refers to the organic radical represented by the structural formula:

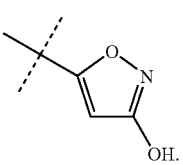

The dotted line symbol crossing a solid line representing a bond

means that the bond so marked is the bond of attachement, for example, the group;

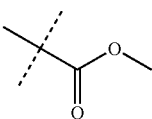

The term, "mammal" includes humans.
The term "halo" refer to fluorine, chlorine, bromine, and iodine.
The term "sulfonate" refers to the group

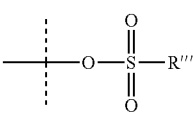

where R''' is $C_1$-$C_5$ alkyl, $C_1$-$C_5$ fluoroalkyl,

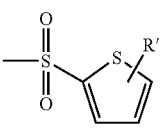

where R' is —$CO_2H$, —$CO_2R'''$, —OH, —$CF_3$, or $C_1$-$C_5$ alkyl.
The term "sulfonamide" refers to the group methyl, ethyl, branched $C_3$-$C_5$ alkyl,

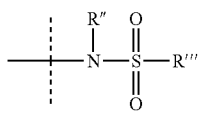

where R" is H, $C_1$-$C_5$ alkyl, $C_1$-$C_5$ fluoroalkyl, or

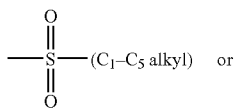

where R''' is $C_1$-$C_5$ alkyl, $C_1$-$C_5$ fluoroalkyl,

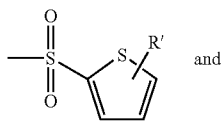 and where R' is —$CO_2H$, —$CO_2R'''$, —OH, —$CF_3$, or $C_1$-$C_5$ alkyl.

The term, "$C_{1-3}$ alkyl" refers to an alkyl group selected from methyl, ethyl, n-propyl, and isopropyl.

The term, "branched $C_3$-$C_5$ alkyl" is an alkyl group selected from 1-methylethyl; 1-methylpropyl; 2-methylpropyl; 1,1-dimethylethyl; 1,1-dimethylpropyl; 1,2-dimethylpropyl; or 2,2-dimethylpropyl. Preferred branched $C_3$-$C_5$ alkyl groups are 2-methylpropyl and 1,1-dimethylethyl, with the 1,1-dimethylethyl group being most preferred.

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. Suitable alkenyl groups have from 2 to about 20 carbon atoms.

The term "$C_1$-$C_5$ alkyl" refers to saturated aliphatic groups including straight-chain, branched-chain, and cyclic groups and any combinations thereof. Examples of $C_1$-$C_5$ alkyl groups are methyl, ethyl, n-propyl, from 1-methylethyl; n-butyl, 1-methylpropyl; 2-methylpropyl; 1,1-dimethylethyl; n-amyl, 1,1-dimethylpropyl; 1,2-dimethylpropyl; and 2,2-dimethylpropyl.

The term "cycloalkyl" includes organic radicals such as cyclopropyl, cyclobutyl, cyclopentyl and cyclohexyl.

The term, "cycloalkenyl" includes organic radicals such as cyclopropenyl, cyclobutenyl, cyclopentenyl and cyclohexenyl.

The term, "$C_1$-$C_5$ fluoroalkyl" is an alkyl group containing fluorine and includes organic radicals such as —$CF_3$, —$CHF_2$, —$CH_2F$, —$CF_2CF_3$, —$CHFCF_3$, —$CH_2CF_3$, —$CH_2CHF_2$, and —$CH_2CH_2F$, with —$CF_3$ being preferred.

The abbreviation, "Me" means methyl.
The abbreviation, "Et" means ethyl.
The abbreviation, "iPr" means 1-methylethyl.
The abbreviation, "tBu" means 1,1-dimethylethyl.

The term "terminal hydroxyalkyl" is a group selected from
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
1-hydroxycycloalkenyl; or
1-hydroxycycloalkyl.

The term, "3-methyl-3-hydroxypentyl" refers to the radical having the structural formula:

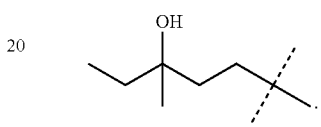

The term, "3-methyl-3-hydroxypentenyl" refers to the radical having the structural formula (both cis and trans isomers):

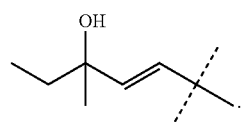

The term, "3-methyl-3-hydroxypentynyl" refers to the radical having the structural formula:

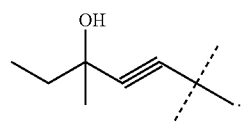

The term, "3-ethyl-3-hydroxypentyl" refers to the radical having the structural formula:

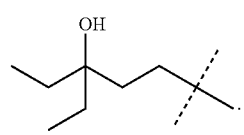

The term, "3-ethyl-3-hydroxypentenyl" refers to the radical having the structural formula (both cis and trans isomers):

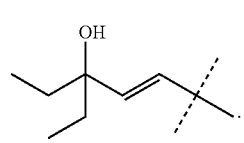

The term, "3-ethyl-3-hydroxypentynyl" refers to the radical having the structural formula:

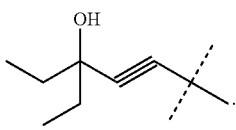

The term, "3-propyl-3-hydroxypentyl" refers to the radical having the structural formula:

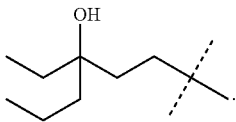

The term, "3-propyl-3-hydroxypentenyl" refers to the radical having the structural formula (both cis and trans isomers):

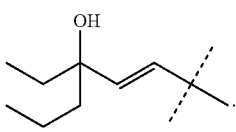

The term, "3-propyl-3-hydroxypentynyl" refers to the radical having the structural formula:

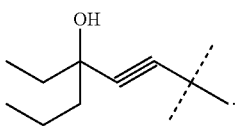

The term, "3-ethyl-3-hydroxy-4-methylpentyl" refers to the radical having the structural formula:

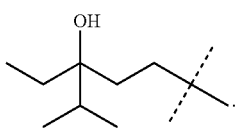

The term, "3-ethyl-3-hydroxy-4-methylpentenyl" refers to the radical having the structural formula (both cis and trans isomers):

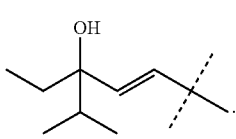

The term, "3-ethyl-3-hydroxy-4-methylpentynyl" refers to the radical having the structural formula:

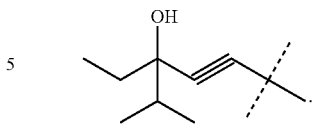

The term, "1-hydroxy-2-methyl-1-(methylethyl)propyl" refers to the radical having the structural formula:

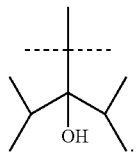

The term, "3-methyl-3-hydroxy-4,4-dimethylpentyl" refers to the radical having the structural formula:

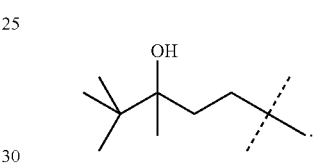

The term, "3-methyl-3-hydroxy-4,4-dimethylpentenyl." refers to the radical having the structural formula (both cis and trans isomers):

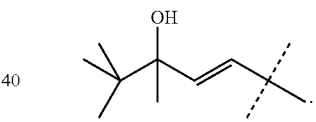

The term, "3-methyl-3-hydroxy-4,4-dimethylpentynyl" refers to the radical having the structural formula:

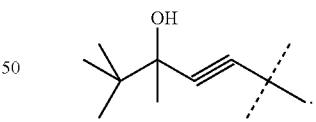

The term, "3-ethyl-3-hydroxy-4,4-dimethylpentyl" refers to the radical having the structural formula:

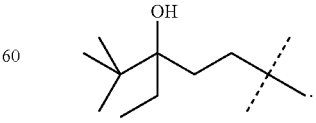

The term, "3-ethyl-3-hydroxy-4,4-dimethylpentenyl" refers to the radical having the structural formula (both cis and trans isomers):

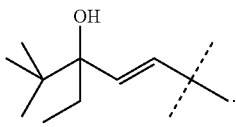

The term, "3-ethyl-3-hydroxy-4,4-dimethylpentynyl" refers to the radical having the structural formula:

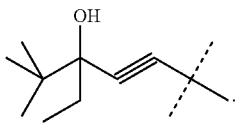

The term, "1-hydroxycycloalkenyl" refers to a radical selected from 1-hydroxycyclopentenyl, 1-hydroxycyclohexenyl, 1-hydroxycycloheptenyl, or 1-hydroxycyclooctenyl.

The term "hydroxycycloalkyl" refers to a radical having the general structural formula:

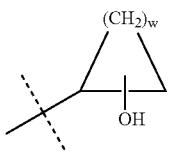

where w is an integer from 1 to 6 and the hydroxyl radical is substituted on any ring carbon atom.

The term "1-hydroxycycloalkyl" refers to a radical having the general structural formula:

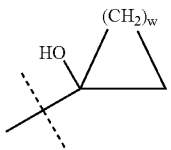

Examples of 1-hydroxycycloalkyl radicals are 1-hydroxycyclopropyl, 1-hydroxycyclobutyl, 1-hydroxycyclopentyl, 1-hydroxycyclohexyl, 1-hydroxycycloheptyl, and 1-hydroxycyclooctyl.

The abbreviation, "Me" means methyl.
The abbreviation, "Et" means ethyl.
The abbreviation, "iPr" means 1-methylethyl.
The abbreviation, "nPr" means n-propyl.
The abbreviation, "3Me3OH-Pentyl" means 3-methyl-3-hydroxypentyl.
The abbreviation, "3Me3OH-Pentenyl" means 3-methyl-3-hydroxypentenyl
The abbreviation, "3Me3OH-Pentynyl" means 3-methyl-3-hydroxypentynyl
The abbreviation, "3Et3OH-Pentyl" means 3-ethyl-3-hydroxypentyl.
The abbreviation, "3Et3OH-Pentenyl" means 3-ethyl-3-hydroxypentenyl
The abbreviation, "3Et3OH-Pentynyl" means 3-ethyl-3-hydroxypentynyl The abbreviation, "3Pr3OH-Pentyl" means 3-propyl-3-hydroxypentyl.
The abbreviation, "3Pr3OH-Pentenyl" means 3-propyl-3-hydroxypentenyl.
The abbreviation, "3Pr3OH-Pentynyl" means 3-propyl-3-hydroxypentynyl.
The abbreviation, "3Et3OH4Me-Pentyl" means 3-ethyl-3-hydroxy-4-methylpentyl.
The abbreviation, "3Et3OH4Me-Pentenyl" means 3-ethyl-3-hydroxy-4-methylpentenyl,
The abbreviation, "3Et3OH4Me-Pentynyl" means 3-ethyl-3-hydroxy-4-methylpentynyl.
The abbreviation, "1OH2Me1MeEt-Propyl" means 1-hydroxy-2-methyl-1-(methylethyl)propyl.
The dotted line symbol crossing a solid line representing a bond

means that the bond so marked is the bond of attachment.
The term, "mammal" includes humans.

Compounds of the Invention

The compounds of the invention with vitamin receptor modulating (VDRM) activity are represented by formula (I) or a pharmaceutically acceptable salt or a prodrug derivative thereof:

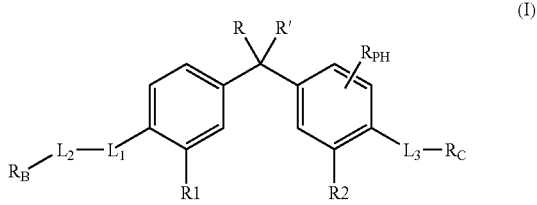

wherein;

R and R' are independently $C_1$-$C_5$ alkyl, $C_1$-$C_5$ fluoroalkyl, or together R and R' form a substituted or unsubstituted, saturated or unsaturated carbocyclic ring having from 3 to 8 carbon atoms;

$R_{PH}$ is hydrogen or methyl;

R1 and R2 are independently selected from the group consisting of hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —NO$_2$, acetyl, —S—$C_1$-$C_5$ fluoroalkyl, $C_2$-$C_5$ alkenyl, $C_3$-$C_5$ cycloalkyl, and $C_3$-$C_5$ cycloalkenyl;

$L_1$ and $L_2$ and $L_3$ are independently divalent linking groups independently selected from the group consisting of

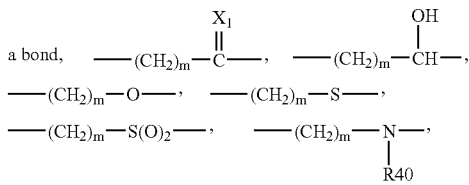

-continued

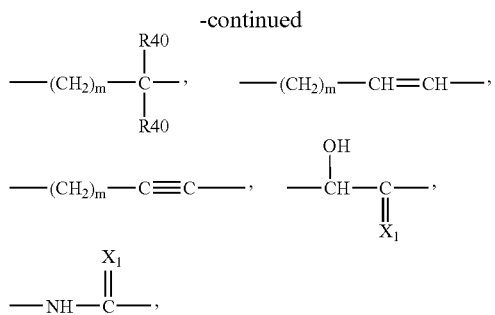

where m is 0, 1 or 2, $X_1$ is oxygen or sulfur, and each R40 is independently hydrogen, $C_1$-$C_5$ alkyl, or $C_1$-$C_5$ fluoroalkyl;

$R_B$ is
branched $C_3$-$C_5$ alkyl,
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
4,4-dimethyl-3-hydroxypropyl,
1-hydroxycycloypentenyl,
1-hydroxycyclohexenyl,
1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
1-hydroxycycloheptyl, or
1-hydroxycyclooctyl;

provided, however, that when
$R_B$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
4,4-dimethyl-3-hydroxypropyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl, or
1-hydroxy-2-methyl-1-(methylethyl)propyl;
then $L_1$ and $L_2$ combine as a bond; and
$R_C$ is
—O—SO$_2$—(R50)
where R50 is
—$C_{1-3}$alkyl, —CF$_3$, —(CH$_2$)$_{1-2}$CF$_3$, —S—$C_{1-3}$alkyl, —SO$_2$—$C_{1-3}$alkyl, —(CH$_2$)$_{1-2}$C(O)NHMe, —(CH$_2$)$_{1-2}$—CO$_2$H; or
—NH—SO$_2$—(R50)
where R50 is
—$C_{1-3}$alkyl, —CF$_3$, —(CH$_2$)$_{1-2}$CF$_3$, —S—$C_{1-3}$alkyl, —SO$_2$—$C_{1-3}$alkyl, —(CH$_2$)$_{1-2}$—CO$_2$H, —(CH$_2$)$_{1-2}$C(O)NHMe, or
—N(SO$_2$R51)$_2$
where each R51 is independently,
—$C_{1-3}$alkyl, —CF$_3$, —(CH$_2$)$_{1-2}$CF$_3$, —(CH$_2$)$_{1-2}$C(O)NHMe, —S—$C_{1-3}$alkyl, —SO$_2$—$C_{1-3}$alkyl, or —(CH$_2$)$_{1-2}$—CO$_2$H.

In the preceding formula I the divalent linking groups to be oriented in either direction, for example, where divalent linker ($L_1$) has the identity —(CH$_2$)$_m$—O—, it may be configured:

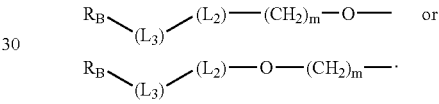

Preferred compounds of the invention with VDR modulating activities are represented by formula (II) or a pharmaceutically acceptable salt or a prodrug derivative thereof:

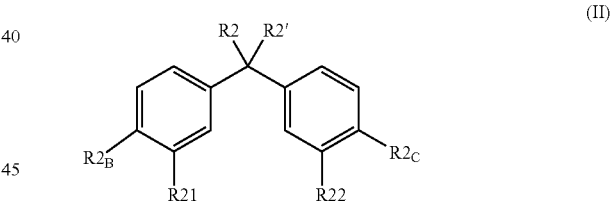

(II)

wherein;
R2 and R2' are independently methyl or ethyl;
R21 and R22 are independently selected from the group consisting of hydrogen, fluoro, —Cl, —CF$_3$, —CH$_2$F, —CHF$_2$, methoxy, ethoxy, vinyl, methyl, ethyl, propyl, 1-methylethyl, 1,1-dimethylethyl, butyl, 1-methylpropyl, 2-methylpropyl, or cyclopropyl;
$R2_B$ is a group represented by the formula:
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl, 3-propyl-3-hydroxypentynyl,
1-hydroxy-2-methyl-1-(methylethyl)propyl
R2$_C$ is

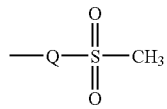

wherein Q is —O— or —NH—.

Preferred compounds have the substituent R2$_C$ of formula II as:

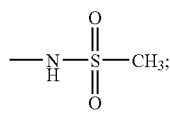

Preferred compounds of the invention with VDR modulating activities are represented by formula (III) or a pharmaceutically acceptable salt or a prodrug derivative thereof:

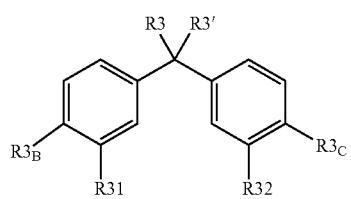

(III)

wherein;

R3 and R3' are independently methyl or ethyl;

R31 and R32 are independently selected from the group consisting of hydrogen, fluoro, —Cl, —CF$_3$, —CH$_2$F, —CHF$_2$, methoxy, ethoxy, vinyl, methyl, ethyl, propyl, 1-methylethyl, 1,1-dimethylethyl, butyl, 1-methylpropyl, 2-methylpropyl, or cyclopropyl;

R3$_B$ is 3-hydroxy-3-ethyl-pentyl or 4,4-dimethyl(-3-hydroxypropyl).

R3$_c$ is

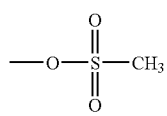 or 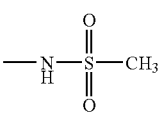

Preferred compounds of the invention are represented by the structural formulae M-1 to M-31 as follows:

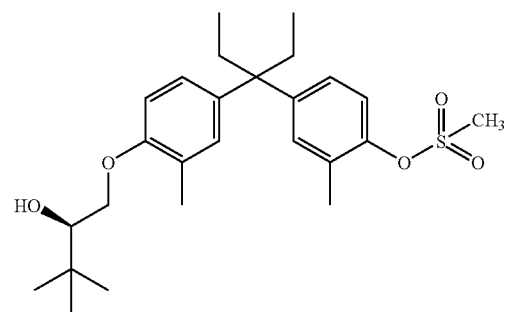

M-1)

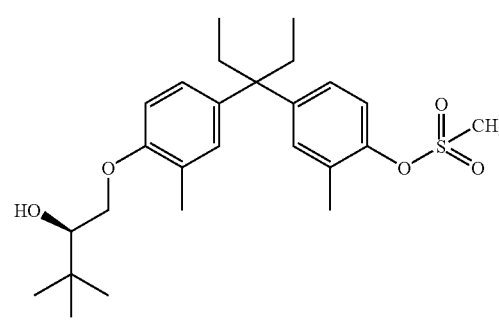

M-2)

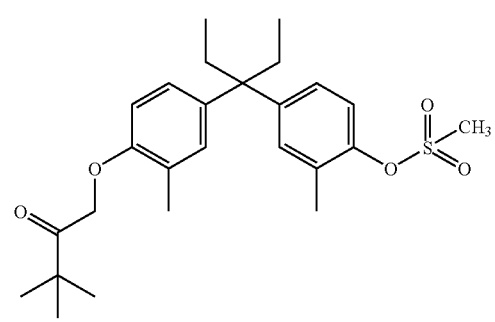

M-3)

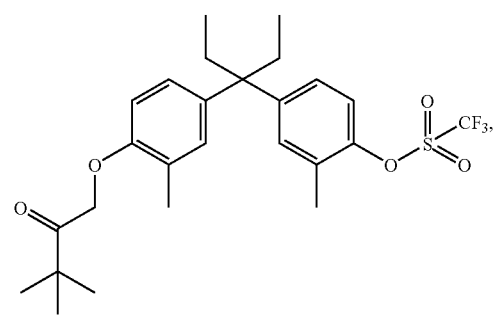

M-4)

M-5)
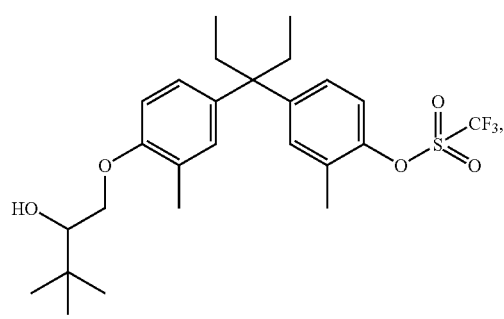
M-6)
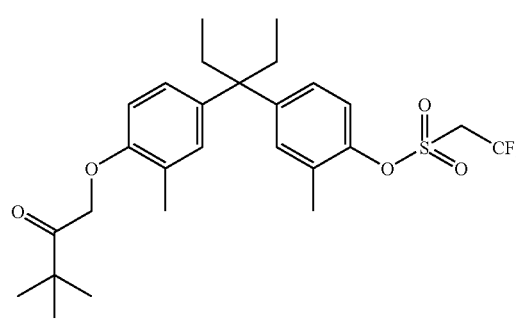
M-7)
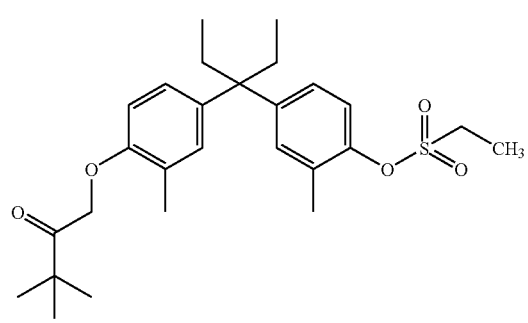
M-8)
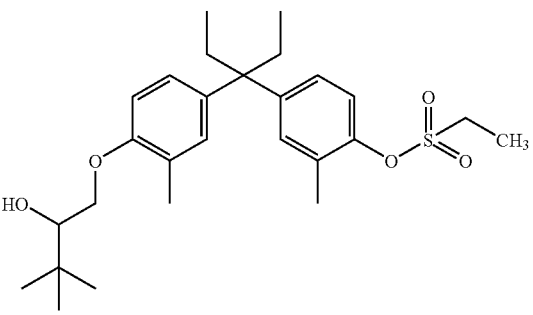
M-9)
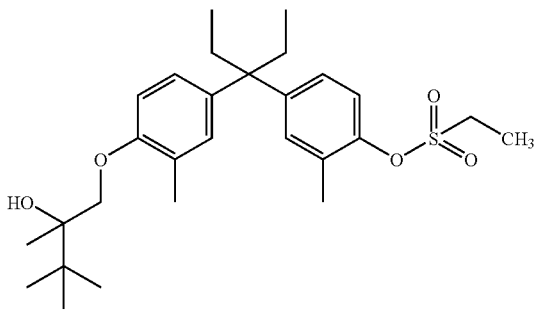
M-10)
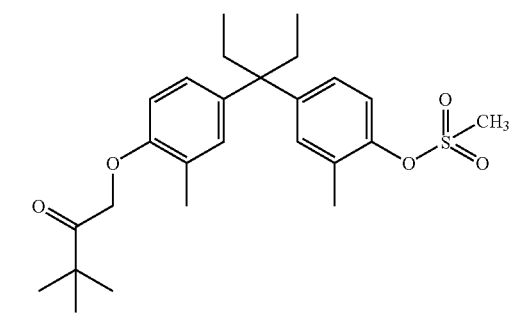
M-11)
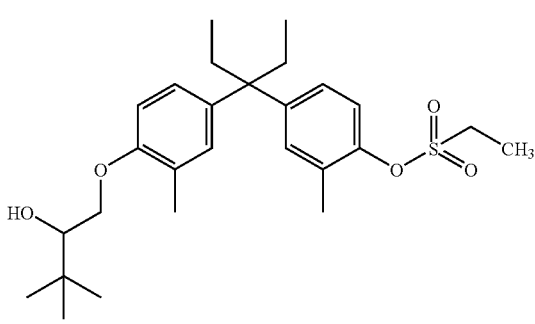
M-12)
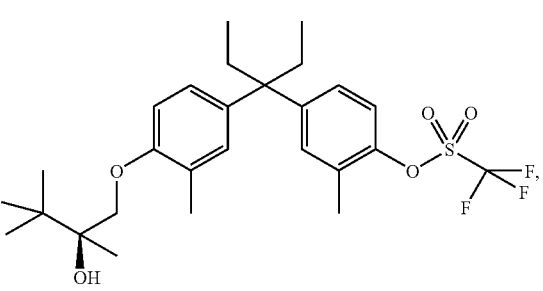
M-13)
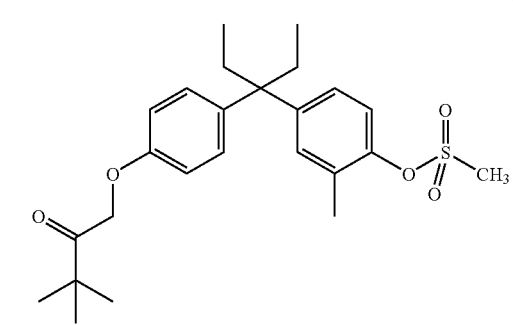

M-14)
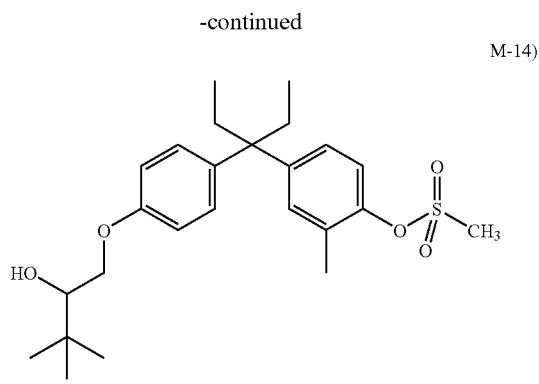
M-15)
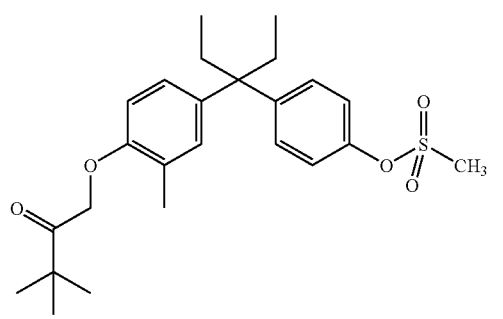
M-16)
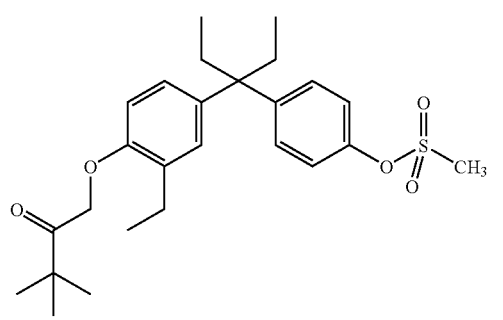
M-17)
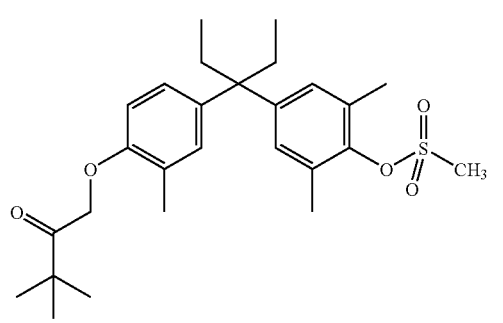
M-18)
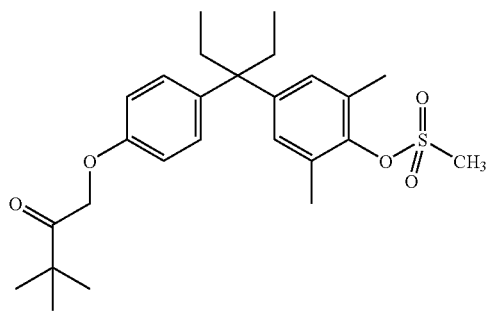
M-19)
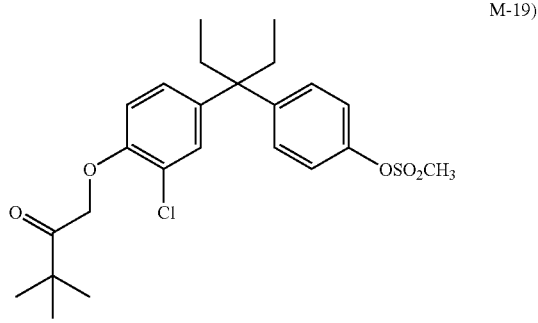
M-20)
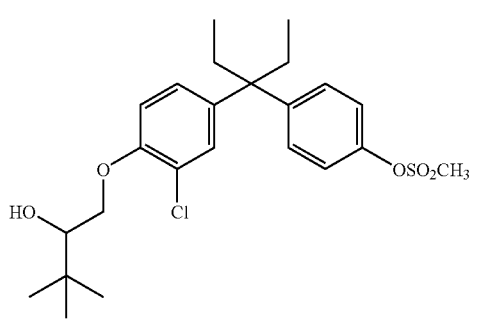
M21)
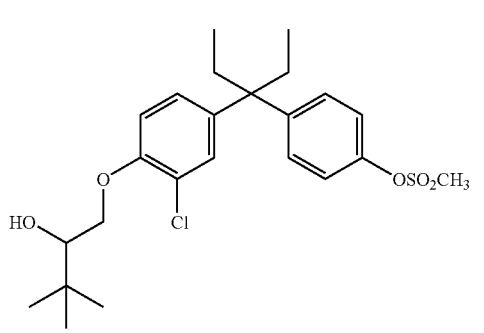
M-22)
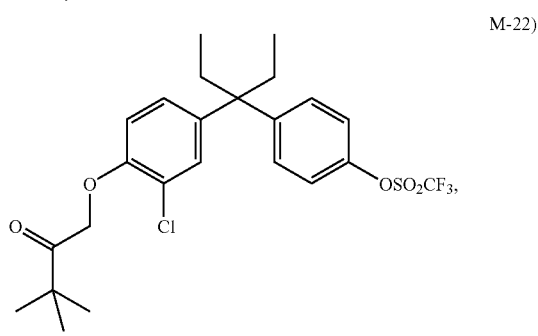

-continued
M-23)
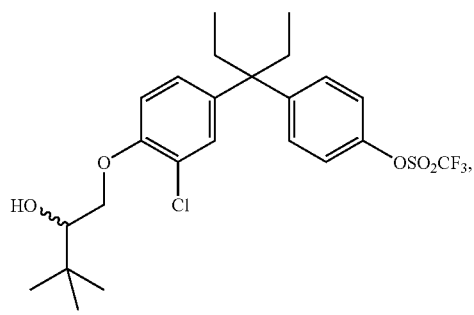
M-24)
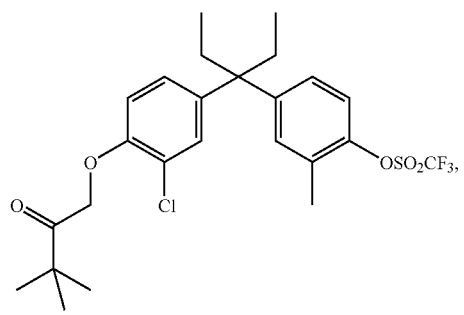
M-25)
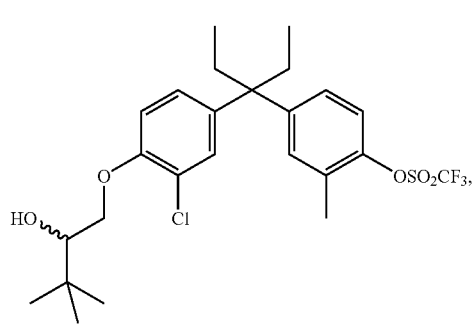
M-26)
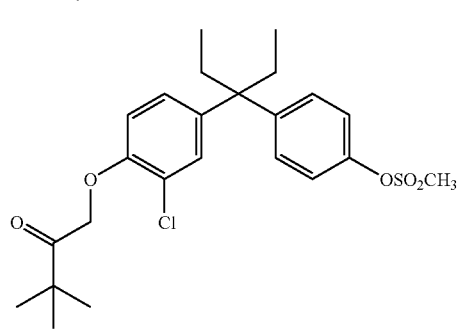
M-27)
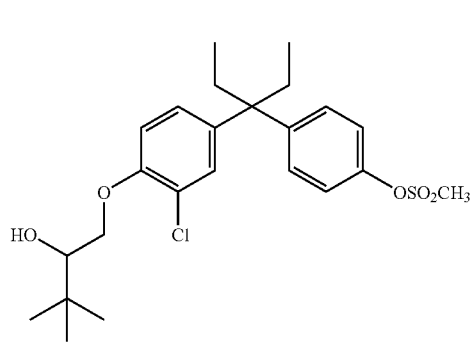
Preferred sulfonamide functional compounds of the invention are represented by the structural formulae M-32 to M-50 as follows:
M-32)
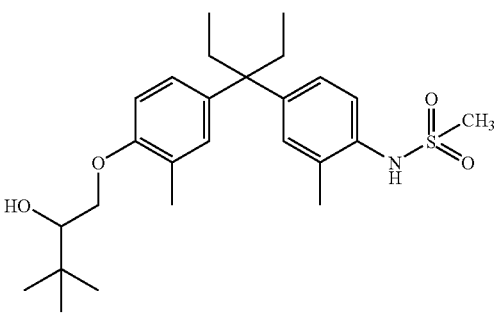
M-33)
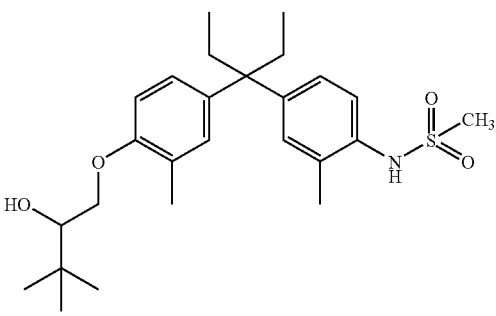
M-34)
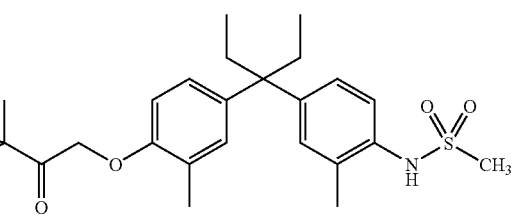
M-35)
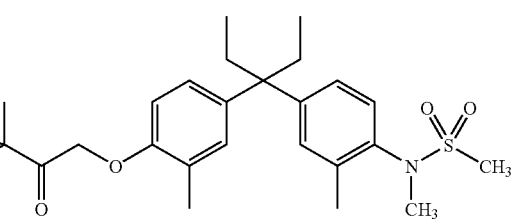
M-36)
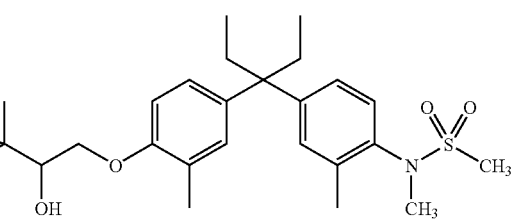

-continued
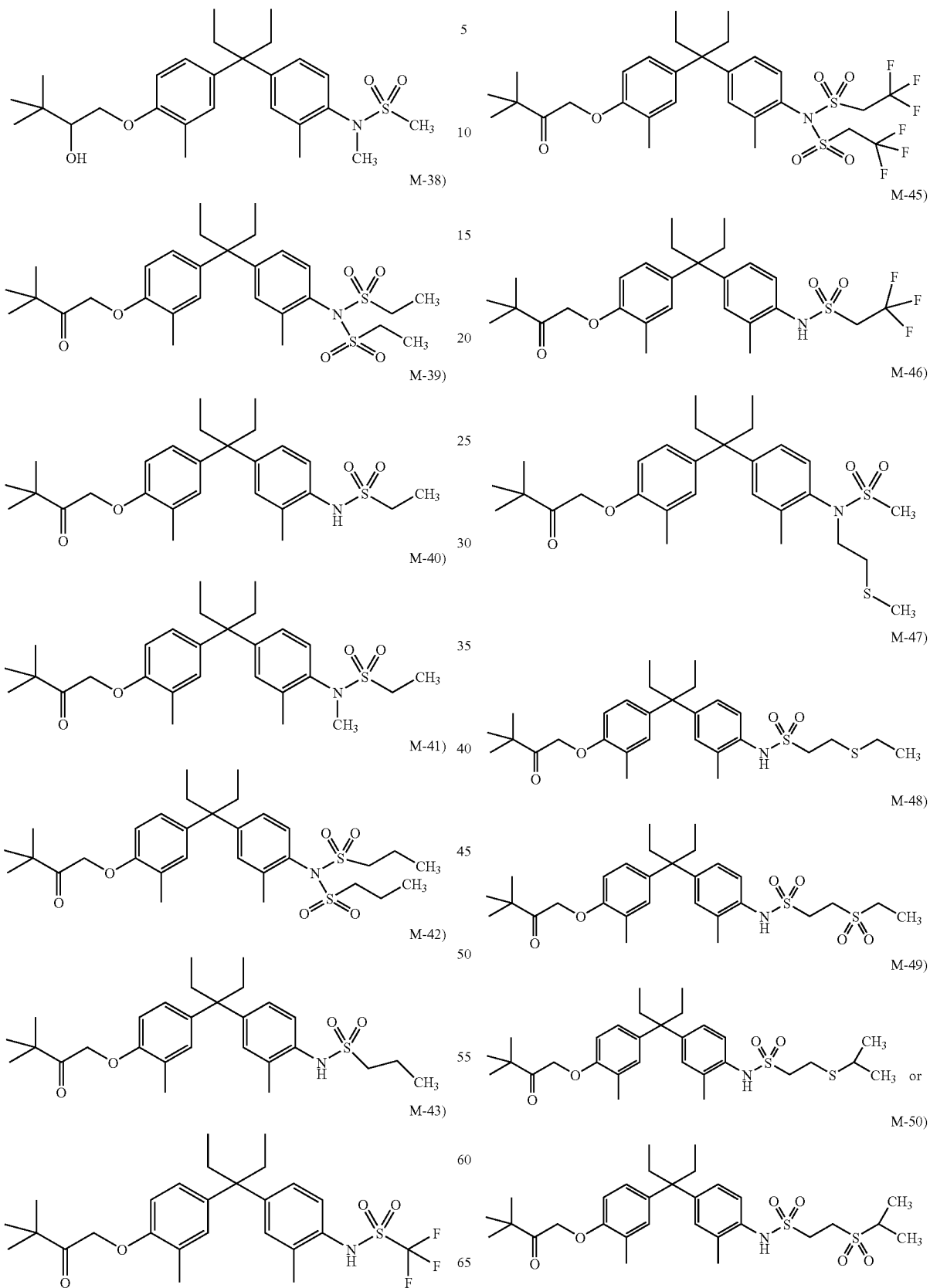

Other preferred compounds of the invention are represented by the formula:
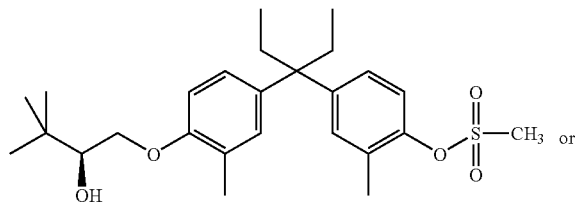
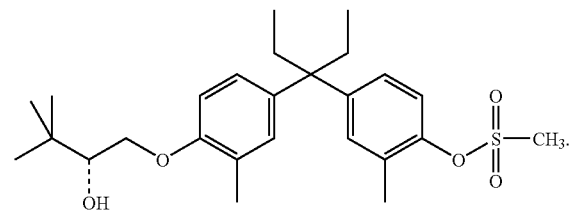
Other preferred compounds of the invention are represented by the formula:
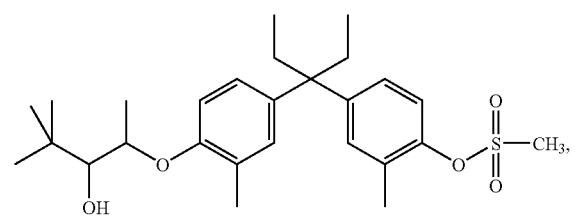
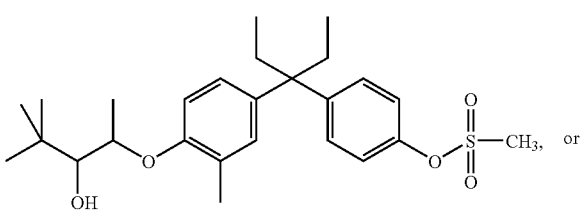
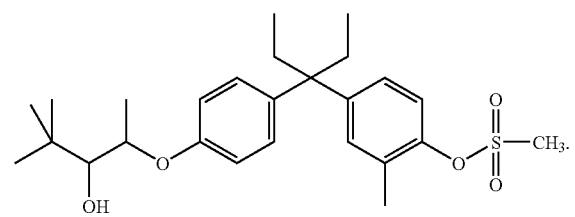
Other preferred compounds of the invention are represented by the formula:
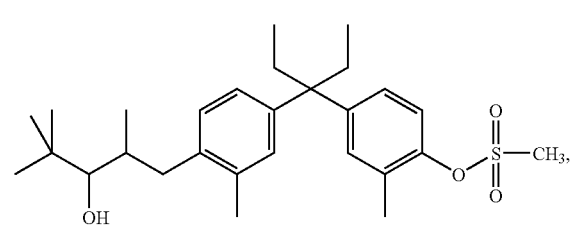
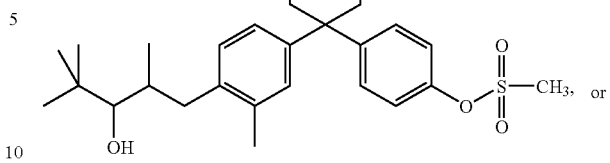
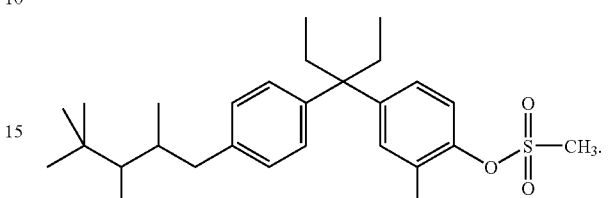
Other preferred compounds of the invention are represented by the formula:
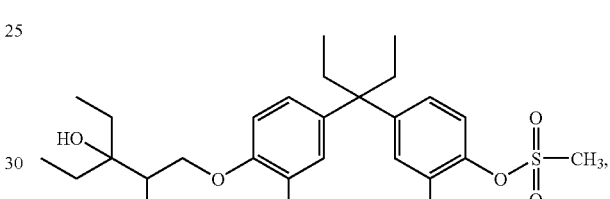
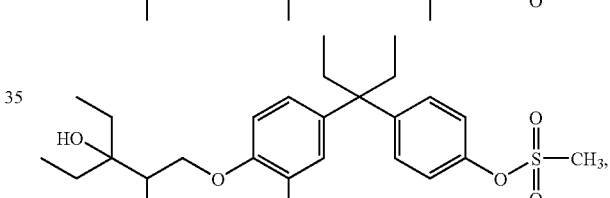
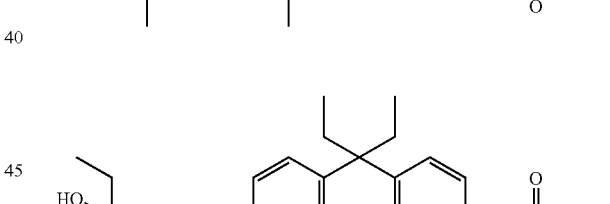
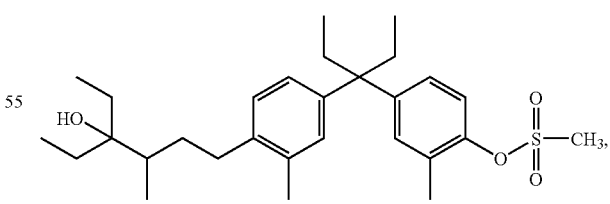
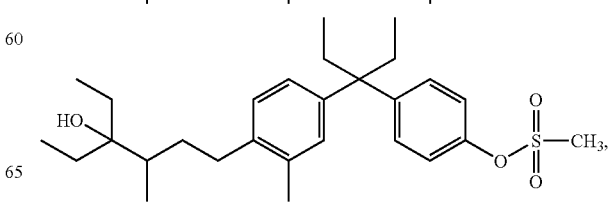

-continued
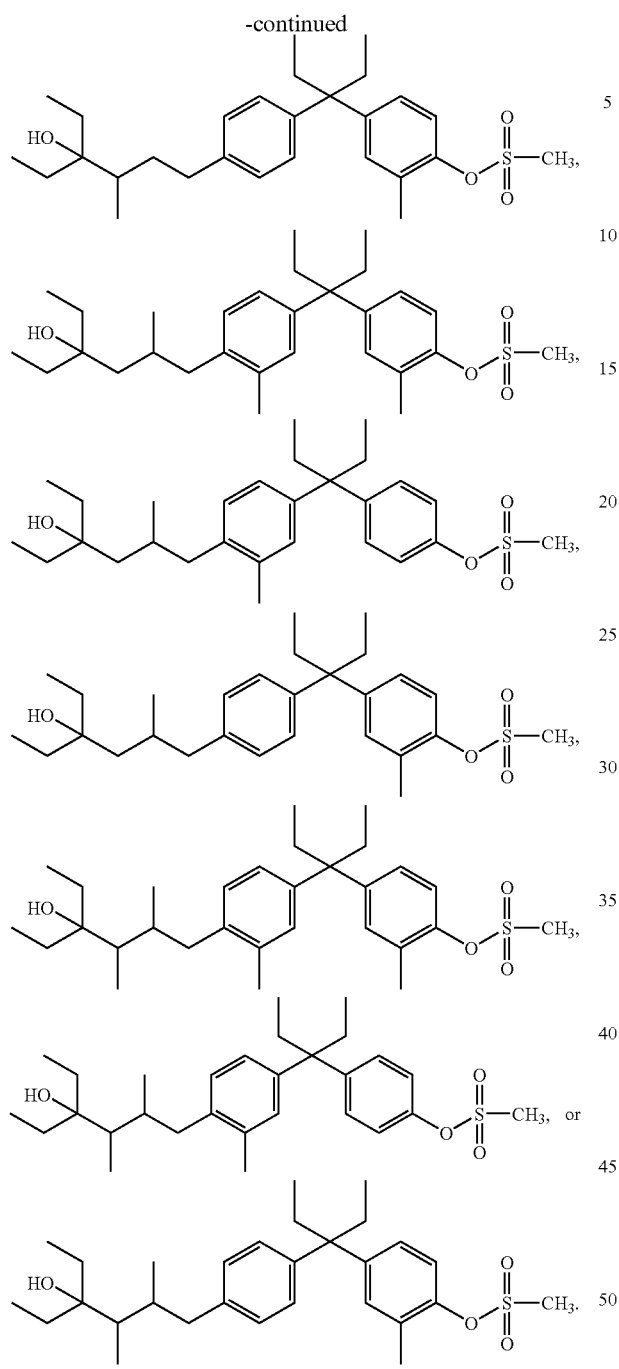
Other preferred compounds of the invention are represented by the formula:
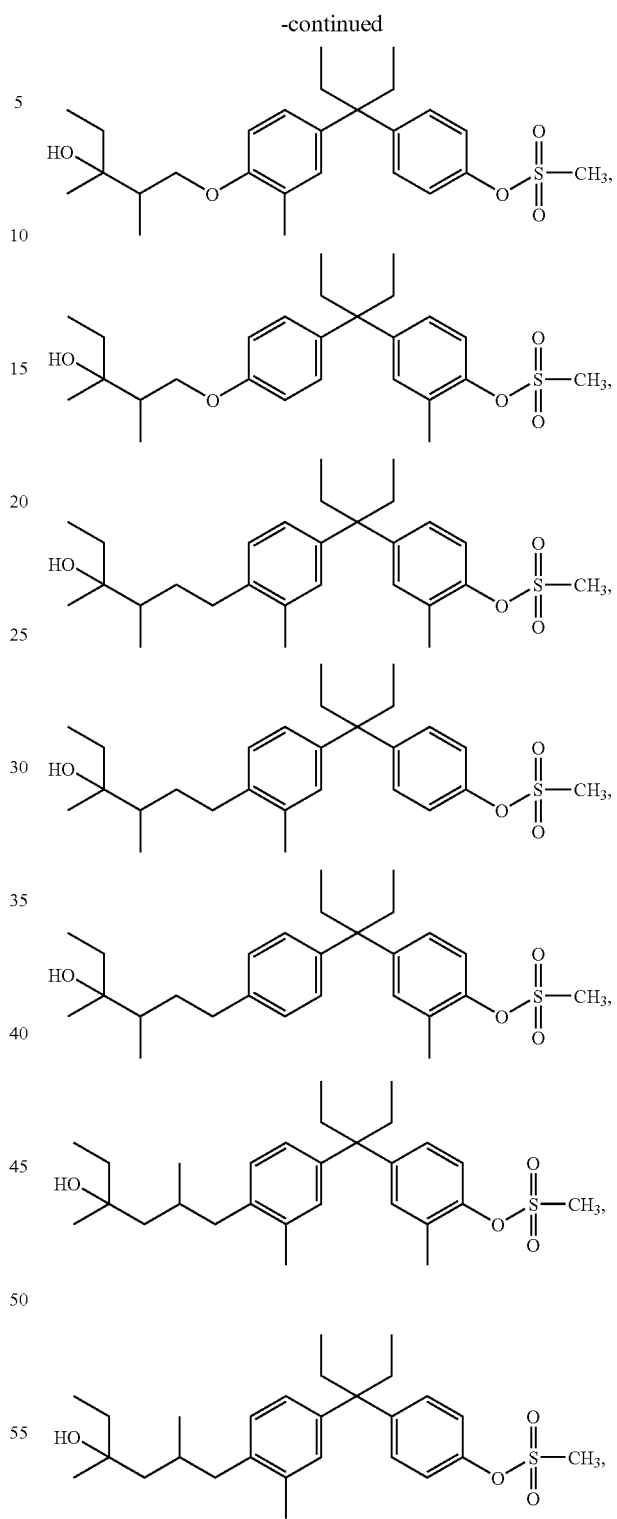

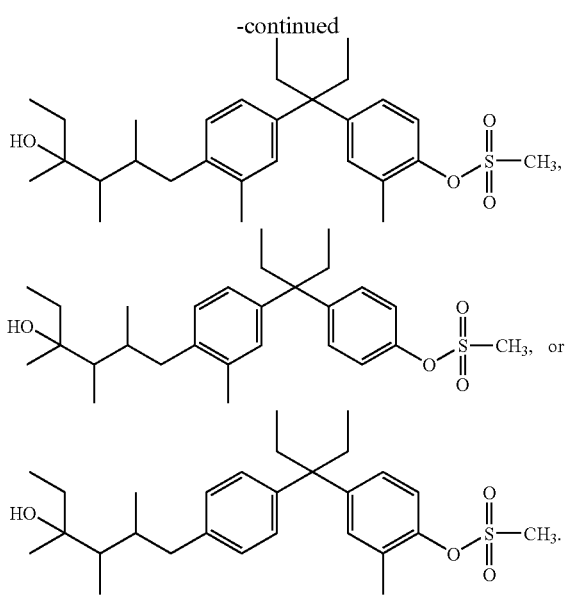

Other specific compounds and pharmaceutically acceptable salts and prodrug derivatives thereof, that are preferred embodiments of this invention and are preferred for for practicing the method of treatment of the invention are set out in the following three Tables. All numbers in the Tables cells reciting chemical species (except for the abbreviation "3Et3OH-Pentyl") are to be understood as subscripts in chemical formulae, for example, in row, Code 11, Column, $R_{C4}$, the symbol, "—O—S(O)2Me" is to be understood as the conventional chemical nomenclature, —O—S(O)$_2$Me. Each row of the Tables is a single compound having an identifying "Code" (e.g., "14", "33A", "21B") defining the specific substituents in the structural formula displayed above each Table, as follows:

A preferred compounds of the invention or a pharmaceutically acceptable salt or an ester prodrug derivative thereof represented by the formula:

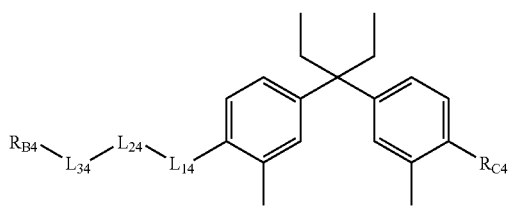

where said compound is selected from a compound code numbered 1 thru 135, with each compound having the specific selection of substituents $R_{B4}$, $R_{C4}$, $L_{14}$, $L_{24}$, $L_{34}$, and RC4 shown in the row following the compound code number, as set out in the following Table 1:

TABLE 1

| Code No. | $R_{B4}$ | $L_{34}$ | $L_{24}$ | $L_{14}$ | $R_{C4}$ |
|---|---|---|---|---|---|
| 1 | tBu | C(O) | CH2 | O | —O—S(O)2Me |
| 2 | tBu | C(O) | CH2 | CH2 | —O—S(O)2Me |
| 3 | tBu | C(O) | CH(Me) | CH2 | —O—S(O)2Me |
| 4 | tBu | CHOH | CH2 | O | —O—S(O)2Me |
| 5 | tBu | CHOH | CH2 | CH2 | —O—S(O)2Me |
| 6 | tBu | CHOH | CH(Me) | CH2 | —O—S(O)2Me |
| 7 | tBu | C(Me)OH | CH2 | O | —O—S(O)2Me |
| 8 | tBu | C(Me)OH | CH2 | CH2 | —O—S(O)2Me |
| 9 | tBu | C(Me)OH | CH(Me) | CH2 | —O—S(O)2Me |
| 10 | 1-hydroxycyclopentyl | bond | CH2 | O | —O—S(O)2Me |
| 11 | 1-hydroxycyclopentyl | bond | CH2 | CH2 | —O—S(O)2Me |
| 12 | 1-hydroxycyclopentyl | bond | CH(Me) | CH2 | —O—S(O)2Me |
| 13 | 1-hydroxycyclopentyl | bond | CH2 | O | —O—S(O)2Me |
| 14 | 1-hydroxycyclopentyl | bond | CH2 | CH2 | —O—S(O)2Me |
| 15 | 1-hydroxycyclopentyl | bond | CH(Me) | CH2 | —O—S(O)2Me |
| 16 | 1-hydroxycyclopentyl | bond | CH2 | O | —O—S(O)2Me |
| 17 | 1-hydroxycyclopentyl | bond | CH2 | CH2 | —O—S(O)2Me |
| 18 | 1-hydroxycyclopentyl | bond | CH(Me) | CH2 | —O—S(O)2Me |
| 19 | 1-hydroxycyclohexyl | bond | CH2 | O | —O—S(O)2Me |
| 20 | 1-hydroxycyclohexyl | bond | CH2 | CH2 | —O—S(O)2Me |
| 21 | 1-hydroxycyclohexyl | bond | CH(Me) | CH2 | —O—S(O)2Me |
| 22 | 1-hydroxycyclohexyl | bond | CH2 | O | —O—S(O)2Me |
| 23 | 1-hydroxycyclohexy | bond | CH2 | CH2 | —O—S(O)2Me |
| 24 | 1-hydroxycyclohexyl | bond | CH(Me) | CH2 | —O—S(O)2Me |
| 25 | 1-hydroxycyclohexyl | bond | CH2 | O | —O—S(O)2Me |
| 26 | 1-hydroxycyclohexyl | bond | CH2 | CH2 | —O—S(O)2Me |
| 27 | 1-hydroxycyclohexyl | bond | CH(Me) | CH2 | —O—S(O)2Me |
| 28 | tBu | C(O) | CH2 | O | —O—S(O)2Et |
| 29 | tBu | C(O) | CH2 | CH2 | —O—S(O)2Et |
| 30 | tBu | C(O) | CH(Me) | CH2 | —O—S(O)2Et |
| 31 | tBu | CHOH | CH2 | O | —O—S(O)2Et |
| 32 | tBu | CHOH | CH2 | CH2 | —O—S(O)2Et |
| 33 | tBu | CHOH | CH(Me) | CH2 | —O—S(O)2Et |
| 34 | tBu | C(Me)OH | CH2 | O | —O—S(O)2Et |
| 35 | tBu | C(Me)OH | CH2 | CH2 | —O—S(O)2Et |
| 36 | tBu | C(Me)OH | CH(Me) | CH2 | —O—S(O)2Et |
| 37 | 1-hydroxycyclopentyl | bond | CH2 | O | —O—S(O)2Et |
| 38 | 1-hydroxycyclopentyl | bond | CH2 | CH2 | —O—S(O)2Et |
| 39 | 1-hydroxycyclopentyl | bond | CH(Me) | CH2 | —O—S(O)2Et |

TABLE 1-continued

| Code No. | $R_{B4}$ | $L_{34}$ | $L_{24}$ | $L_{14}$ | $R_{C4}$ |
|---|---|---|---|---|---|
| 40 | 1-hydroxycyclopentyl | bond | CH2 | O | —O—S(O)2Et |
| 41 | 1-hydroxycyclopentyl | bond | CH2 | CH2 | —O—S(O)2Et |
| 42 | 1-hydroxycyclopentyl | bond | CH(Me) | CH2 | —O—S(O)2Et |
| 43 | 1-hydroxycyclopentyl | bond | CH2 | O | —O—S(O)2Et |
| 44 | 1-hydroxycyclopentyl | bond | CH2 | CH2 | —O—S(O)2Et |
| 45 | 1-hydroxycyclopentyl | bond | CH(Me) | CH2 | —O—S(O)2Et |
| 46 | 1-hydroxycyclohexyl | bond | CH2 | O | —O—S(O)2Et |
| 47 | 1-hydroxycyclohexyl | bond | CH2 | CH2 | —O—S(O)2Et |
| 48 | 1-hydroxycyclohexyl | bond | CH(Me) | CH2 | —O—S(O)2Et |
| 49 | 1-hydroxycyclohexyl | bond | CH2 | O | —O—S(O)2Et |
| 50 | 1-hydroxycyclohexy | bond | CH2 | CH2 | —O—S(O)2Et |
| 51 | 1-hydroxycyclohexyl | bond | CH(Me) | CH2 | —O—S(O)2Et |
| 52 | 1-hydroxycyclohexyl | bond | CH2 | O | —O—S(O)2Et |
| 53 | 1-hydroxycyclohexyl | bond | CH2 | CH2 | —O—S(O)2Et |
| 54 | 1-hydroxycyclohexyl | bond | CH(Me) | CH2 | —O—S(O)2Et |
| 55 | tBu | C(O) | CH2 | O | —O—S(O)2CH2CO2H |
| 56 | tBu | C(O) | CH2 | CH2 | —O—S(O)2CH2CO2H |
| 57 | tBu | C(O) | CH(Me) | CH2 | —O—S(O)2CH2CO2H |
| 58 | tBu | CHOH | CH2 | O | —O—S(O)2CH2CO2H |
| 59 | tBu | CHOH | CH2 | CH2 | —O—S(O)2CH2CO2H |
| 60 | tBu | CHOH | CH(Me) | CH2 | —O—S(O)2CH2CO2H |
| 61 | tBu | C(Me)OH | CH2 | O | —O—S(O)2CH2CO2H |
| 62 | tBu | C(Me)OH | CH2 | CH2 | —O—S(O)2CH2CO2H |
| 63 | tBu | C(Me)OH | CH(Me) | CH2 | —O—S(O)2CH2CO2H |
| 64 | 1-hydroxycyclopentyl | bond | CH2 | O | —O—S(O)2CH2CO2H |
| 65 | 1-hydroxycyclopentyl | bond | CH2 | CH2 | —O—S(O)2CH2CO2H |
| 66 | 1-hydroxycyclopentyl | bond | CH(Me) | CH2 | —O—S(O)2CH2CO2H |
| 67 | 1-hydroxycyclopentyl | bond | CH2 | O | —O—S(O)2CH2CO2H |
| 68 | 1-hydroxycyclopentyl | bond | CH2 | CH2 | —O—S(O)2CH2CO2H |
| 69 | 1-hydroxycyclopentyl | bond | CH(Me) | CH2 | —O—S(O)2CH2CO2H |
| 70 | 1-hydroxycyclopentyl | bond | CH2 | O | —O—S(O)2CH2CO2H |
| 71 | 1-hydroxycyclopentyl | bond | CH2 | CH2 | —O—S(O)2CH2CO2H |
| 72 | 1-hydroxycyclopentyl | bond | CH(Me) | CH2 | —O—S(O)2CH2CO2H |
| 73 | 1-hydroxycyclohexyl | bond | CH2 | O | —O—S(O)2CH2CO2H |
| 74 | 1-hydroxycyclohexyl | bond | CH2 | CH2 | —O—S(O)2CH2CO2H |
| 75 | 1-hydroxycyclohexyl | bond | CH(Me) | CH2 | —O—S(O)2CH2CO2H |
| 76 | 1-hydroxycyclohexyl | bond | CH2 | O | —O—S(O)2CH2CO2H |
| 77 | 1-hydroxycyclohexy | bond | CH2 | CH2 | —O—S(O)2CH2CO2H |
| 78 | 1-hydroxycyclohexyl | bond | CH(Me) | CH2 | —O—S(O)2CH2CO2H |
| 79 | 1-hydroxycyclohexyl | bond | CH2 | O | —O—S(O)2CH2CO2H |
| 80 | 1-hydroxycyclohexyl | bond | CH2 | CH2 | —O—S(O)2CH2CO2H |
| 81 | 1-hydroxycyclohexyl | bond | CH(Me) | CH2 | —O—S(O)2CH2CO2H |
| 82 | tBu | C(O) | CH2 | O | —NH—S(O)2Me |
| 83 | tBu | C(O) | CH2 | CH2 | —NH—S(O)2Me |
| 84 | tBu | C(O) | CH(Me) | CH2 | —NH—S(O)2Me |
| 85 | tBu | CHOH | CH2 | O | —NH—S(O)2Me |
| 86 | tBu | CHOH | CH2 | CH2 | —NH—S(O)2Me |
| 87 | tBu | CHOH | CH(Me) | CH2 | —NH—S(O)2Me |
| 88 | tBu | C(Me)OH | CH2 | O | —NH—S(O)2Me |
| 89 | tBu | C(Me)OH | CH2 | CH2 | —NH—S(O)2Me |
| 90 | tBu | C(Me)OH | CH(Me) | CH2 | —NH—S(O)2Me |
| 91 | 1-hydroxycyclopentyl | bond | CH2 | O | —NH—S(O)2Me |
| 92 | 1-hydroxycyclopentyl | bond | CH2 | CH2 | —NH—S(O)2Me |
| 93 | 1-hydroxycyclopentyl | bond | CH(Me) | CH2 | —NH—S(O)2Me |
| 94 | 1-hydroxycyclopentyl | bond | CH2 | O | —NH—S(O)2Me |
| 95 | 1-hydroxycyclopentyl | bond | CH2 | CH2 | —NH—S(O)2Me |
| 96 | 1-hydroxycyclopentyl | bond | CH(Me) | CH2 | —NH—S(O)2Me |
| 97 | 1-hydroxycyclopentyl | bond | CH2 | O | —NH—S(O)2Me |
| 98 | 1-hydroxycyclopentyl | bond | CH2 | CH2 | —NH—S(O)2Me |
| 99 | 1-hydroxycyclopentyl | bond | CH(Me) | CH2 | —NH—S(O)2Me |
| 100 | 1-hydroxycyclohexyl | bond | CH2 | O | —NH—S(O)2Me |
| 101 | 1-hydroxycyclohexyl | bond | CH2 | CH2 | —NH—S(O)2Me |
| 102 | 1-hydroxycyclohexyl | bond | CH(Me) | CH2 | —NH—S(O)2Me |
| 103 | 1-hydroxycyclohexyl | bond | CH2 | O | —NH—S(O)2Me |
| 104 | 1-hydroxycyclohexyl | bond | CH2 | CH2 | —NH—S(O)2Me |
| 105 | 1-hydroxycyclohexyl | bond | CH(Me) | CH2 | —NH—S(O)2Me |
| 106 | 1-hydroxycyclohexyl | bond | CH2 | O | —NH—S(O)2Me |
| 107 | 1-hydroxycyclohexyl | bond | CH2 | CH2 | —NH—S(O)2Me |
| 108 | 1-hydroxycyclohexyl | bond | CH(Me) | CH2 | —NH—S(O)2Me |
| 109 | tBu | C(O) | CH2 | O | —NH—S(O)2CH2CO2H |
| 110 | tBu | C(O) | CH2 | CH2 | —NH—S(O)2CH2CO2H |
| 111 | tBu | C(O) | CH(Me) | CH2 | —NH—S(O)2CH2CO2H |
| 112 | tBu | CHOH | CH2 | O | —NH—S(O)2CH2CO2H |
| 113 | tBu | CHOH | CH2 | CH2 | —NH—S(O)2CH2CO2H |
| 114 | tBu | CHOH | CH(Me) | CH2 | —NH—S(O)2CH2CO2H |
| 115 | tBu | C(Me)OH | CH2 | O | —NH—S(O)2CH2CO2H |
| 116 | tBu | C(Me)OH | CH2 | CH2 | —NH—S(O)2CH2CO2H |

TABLE 1-continued

| Code No. | $R_{B4}$ | $L_{34}$ | $L_{24}$ | $L_{14}$ | $R_{C4}$ |
|---|---|---|---|---|---|
| 117 | tBu | C(Me)OH | CH(Me) | CH2 | —NH—S(O)2CH2CO2H |
| 118 | 1-hydroxycyclopentyl | bond | CH2 | O | —NH—S(O)2CH2CO2H |
| 119 | 1-hydroxycyclopentyl | bond | CH2 | CH2 | —NH—S(O)2CH2CO2H |
| 120 | 1-hydroxycyclopentyl | bond | CH(Me) | CH2 | —NH—S(O)2CH2CO2H |
| 121 | 1-hydroxycyclopentyl | bond | CH2 | O | —NH—S(O)2CH2CO2H |
| 122 | 1-hydroxycyclopentyl | bond | CH2 | CH2 | —NH—S(O)2CH2CO2H |
| 123 | 1-hydroxycyclopentyl | bond | CH(Me) | CH2 | —NH—S(O)2CH2CO2H |
| 124 | 1-hydroxycyclopentyl | bond | CH2 | O | —NH—S(O)2CH2CO2H |
| 125 | 1-hydroxycyclopentyl | bond | CH2 | CH2 | —NH—S(O)2CH2CO2H |
| 126 | 1-hydroxycyclopentyl | bond | CH(Me) | CH2 | —NH—S(O)2CH2CO2H |
| 127 | 1-hydroxycyclohexyl | bond | CH2 | O | —NH—S(O)2CH2CO2H |
| 128 | 1-hydroxycyclohexyl | bond | CH2 | CH2 | —NH—S(O)2CH2CO2H |
| 129 | 1-hydroxycyclohexyl | bond | CH(Me) | CH2 | —NH—S(O)2CH2CO2H |
| 130 | 1-hydroxycyclohexyl | bond | CH2 | O | —NH—S(O)2CH2CO2H |
| 131 | 1-hydroxycyclohexyl | bond | CH2 | CH2 | —NH—S(O)2CH2CO2H |
| 132 | 1-hydroxycyclohexyl | bond | CH(Me) | CH2 | —NH—S(O)2CH2CO2H |
| 133 | 1-hydroxycyclohexyl | bond | CH2 | O | —NH—S(O)2CH2CO2H |
| 134 | 1-hydroxycyclohexyl | bond | CH2 | CH2 | —NH—S(O)2CH2CO2H |
| 135 | 1-hydroxycyclohexyl | bond | CH(Me) | CH2 | —NH—S(O)2CH2CO2H |

A preferred compound of the invention or a pharmaceutically acceptable salt or an ester prodrug derivative thereof represented by the formula:

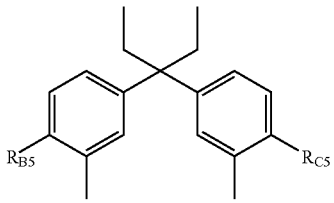

where said compound is selected from a compound code numbered 1A thru 45A, with each compound having the specific selection of substituents $R_{B5}$ and $R_{C5}$ shown in the row following the compound code number, as set out in the following Table 2:

TABLE 2

| Code No. | $R_{B5}$ | $R_{C5}$ |
|---|---|---|
| 1A | 3Et3OH-Pentyl | —NH—S(O)2CH2CO2H |
| 2A | 3Et3OH-Pentyl | —NH—S(O)2CH2CO2H |
| 3A | 3Et3OH-Pentyl | —NH—S(O)2CH2CO2H |
| 4A | 3Et3OH-Pentyl | —NH—S(O)2CH2CO2H |
| 5A | 3Et3OH-Pentyl | —NH—S(O)2CH2CO2H |
| 6A | 3Et3OH-Pentyl | —NH—S(O)2CH2CO2H |
| 7A | 3Et3OH-Pentyl | —NH—S(O)2CH2CO2H |
| 8A | 3Et3OH-Pentyl | —NH—S(O)2CH2CO2H |
| 9A | 3Et3OH-Pentyl | —NH—S(O)2CH2CO2H |
| 10A | 3Et3OH-Pentyl | —O—S(O)2Me |
| 11A | 3Et3OH-Pentyl | —O—S(O)2Me |
| 12A | 3Et3OH-Pentyl | —O—S(O)2Me |
| 13A | 3Et3OH-Pentyl | —O—S(O)2Me |
| 14A | 3Et3OH-Pentyl | —O—S(O)2Me |
| 15A | 3Et3OH-Pentyl | —O—S(O)2Me |
| 16A | 3Et3OH-Pentyl | —O—S(O)2Me |
| 17A | 3Et3OH-Pentyl | —O—S(O)2Me |
| 18A | 3Et3OH-Pentyl | —O—S(O)2Me |
| 19A | 3Et3OH-Pentyl | —O—S(O)2Et |
| 20A | 3Et3OH-Pentyl | —O—S(O)2Et |
| 21A | 3Et3OH-Pentyl | —O—S(O)2Et |
| 22A | 3Et3OH-Pentyl | —O—S(O)2Et |
| 23A | 3Et3OH-Pentyl | —O—S(O)2Et |
| 24A | 3Et3OH-Pentyl | —O—S(O)2Et |
| 25A | 3Et3OH-Pentyl | —O—S(O)2Et |
| 26A | 3Et3OH-Pentyl | —O—S(O)2Et |
| 27A | 3Et3OH-Pentyl | —O—S(O)2Et |
| 28A | 3Et3OH-Pentyl | —O—S(O)2CH2CO2H |
| 29A | 3Et3OH-Pentyl | —O—S(O)2CH2CO2H |
| 30A | 3Et3OH-Pentyl | —O—S(O)2CH2CO2H |
| 31A | 3Et3OH-Pentyl | —O—S(O)2CH2CO2H |
| 32A | 3Et3OH-Pentyl | —O—S(O)2CH2CO2H |
| 33A | 3Et3OH-Pentyl | —O—S(O)2CH2CO2H |
| 34A | 3Et3OH-Pentyl | —O—S(O)2CH2CO2H |
| 35A | 3Et3OH-Pentyl | —O—S(O)2CH2CO2H |
| 36A | 3Et3OH-Pentyl | —O—S(O)2CH2CO2H |
| 37A | 3Et3OH-Pentyl | —NH—S(O)2Me |
| 38A | 3Et3OH-Pentyl | —NH—S(O)2Me |
| 39A | 3Et3OH-Pentyl | —NH—S(O)2Me |
| 40A | 3Et3OH-Pentyl | —NH—S(O)2Me |
| 41A | 3Et3OH-Pentyl | —NH—S(O)2Me |
| 42A | 3Et3OH-Pentyl | —NH—S(O)2Me |
| 43A | 3Et3OH-Pentyl | —NH—S(O)2Me |
| 44A | 3Et3OH-Pentyl | —NH—S(O)2Me |
| 45A | 3Et3OH-Pentyl | —NH—S(O)2Me |

Method of Making the Compounds of the Invention

Compounds of the invention represented by formula (I) may be prepared by the methods set out below. It will be understood by one skilled in the chemical arts that the reactants may be varied to analogous molecules to provide desired substitutions in the final reaction product.

Definitions of symbols used in the Schemes:
(PhO)2P(O)N3—diphenyl phosphorus azide
BBr3—boron tribromide
BF3-OEt2—boron trifluoride etherate
BnBr—benzyl bromide
CH3CN—acetonitrile
DMAP—4-(dimethylamino)pyridine
DMF—N,N-dimethylformamide
DMSO—dimethylsulfoxide
DPPF—dichloro[1,1'-bis(diphenylphosphino)ferrocene
DPPB—1,4-bis(diphenylphosphino)butane EDCI—3-Ethyl-1-[3-(dimethylamino)propyl]carbodiimide hydrochloride
Et3N—triethylamine
EtOH—ethanol
H2NCH2CO2Me—methyl glycinate
HN(OMe)Me—N-methyl-O-methyl hydroxylamine
HNMe2—dimethyl amine
K2CO3—potassium carbonate
KOH—potassium hydroxide
LAH—lithium aluminum hydride
LiHMDS—lithium hexamethyldisilazide
mCPBA—meta-chloroperbenzoic acid
MeI—methyl iodide
MeOH—methanol
NaBH4—sodium borohydride
NaH—sodium hydride
NaI—sodium iodide
NMP—N-methylpyrrolidin-2-one
Na—S—R3—sodium alkylmercaptide
PBr3—phosphorus tribromide
Pd(OAc)2—palladium (II) acetate
Pd—C—palladium on carbon
pTSA—para-toluenesulfonic acid
Pyr—pyridine
R2MgBr—alkyl magnesium bromide
R3MgBr—alkyl magnesium bromide
R5MgBr—alkyl magnesium bromide
R2S(O)2NH2—alkylsulfonamide
tBuC(O)CH2Br—2-bromopinacolone
Tf2O—triflic anhydride
TFA—trifluoroacetic acid
THF—tetrahydrofuran

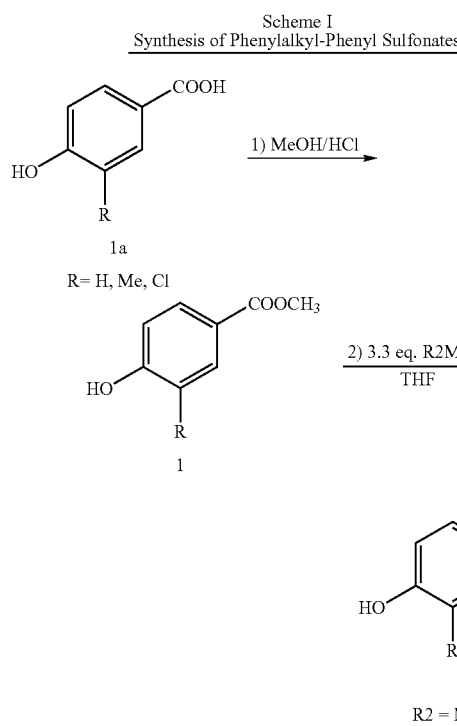

Scheme I
Synthesis of Phenylalkyl-Phenyl Sulfonates

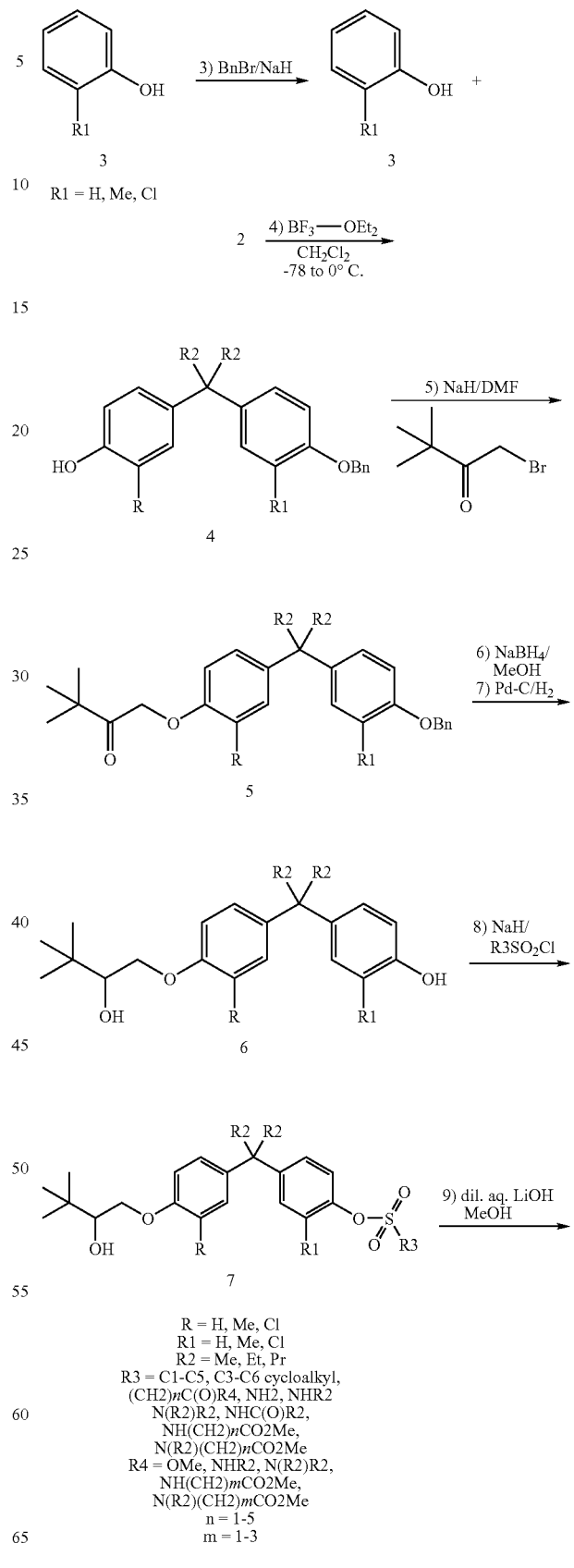

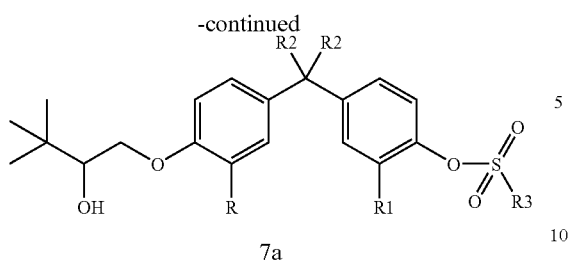
R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1-5
m = 1-3

-continued
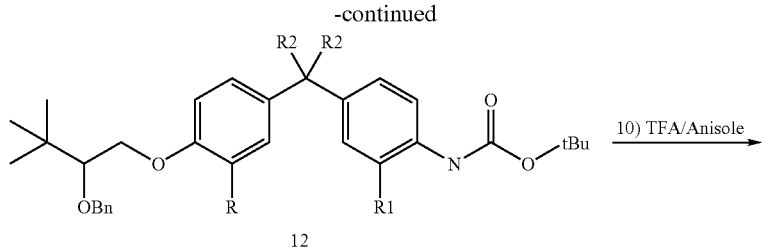
12
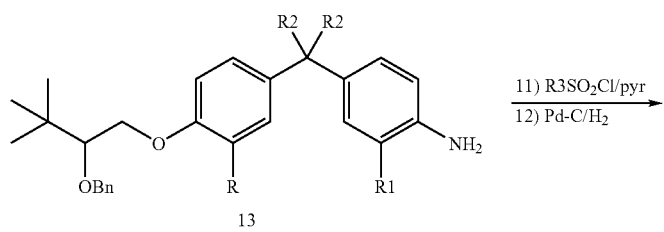
13
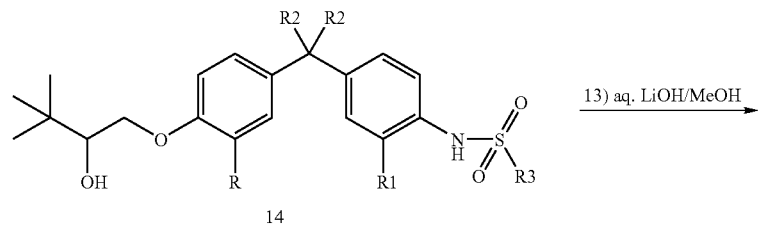
14
R = H, Me, Cl
R1 = H, Me, Cl
R2 = Me, Et, Pr
R3 = C1-C5, C3-C6 cycloalkyl,
(CH2)nC(O)R4, NH2, NHR2
N(R2)R2, NH(CH2)nCO2Me,
N(R2)(CH2)nCO2Me,
R4 = OMe, NHR2, N(R2)R2,
NH(CH2)mCO2Me,
N(R2)(CH2)mCO2Me
n = 1-5
m = 1-3
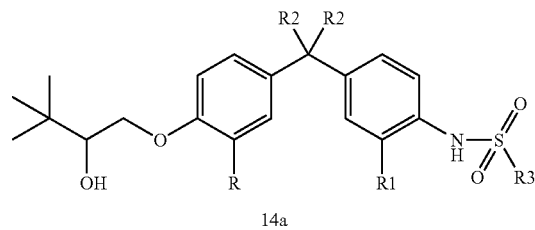
14a
R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1-5
m = 1-3

Scheme 3
Synthesis of Pentanone Sidechain Analogs
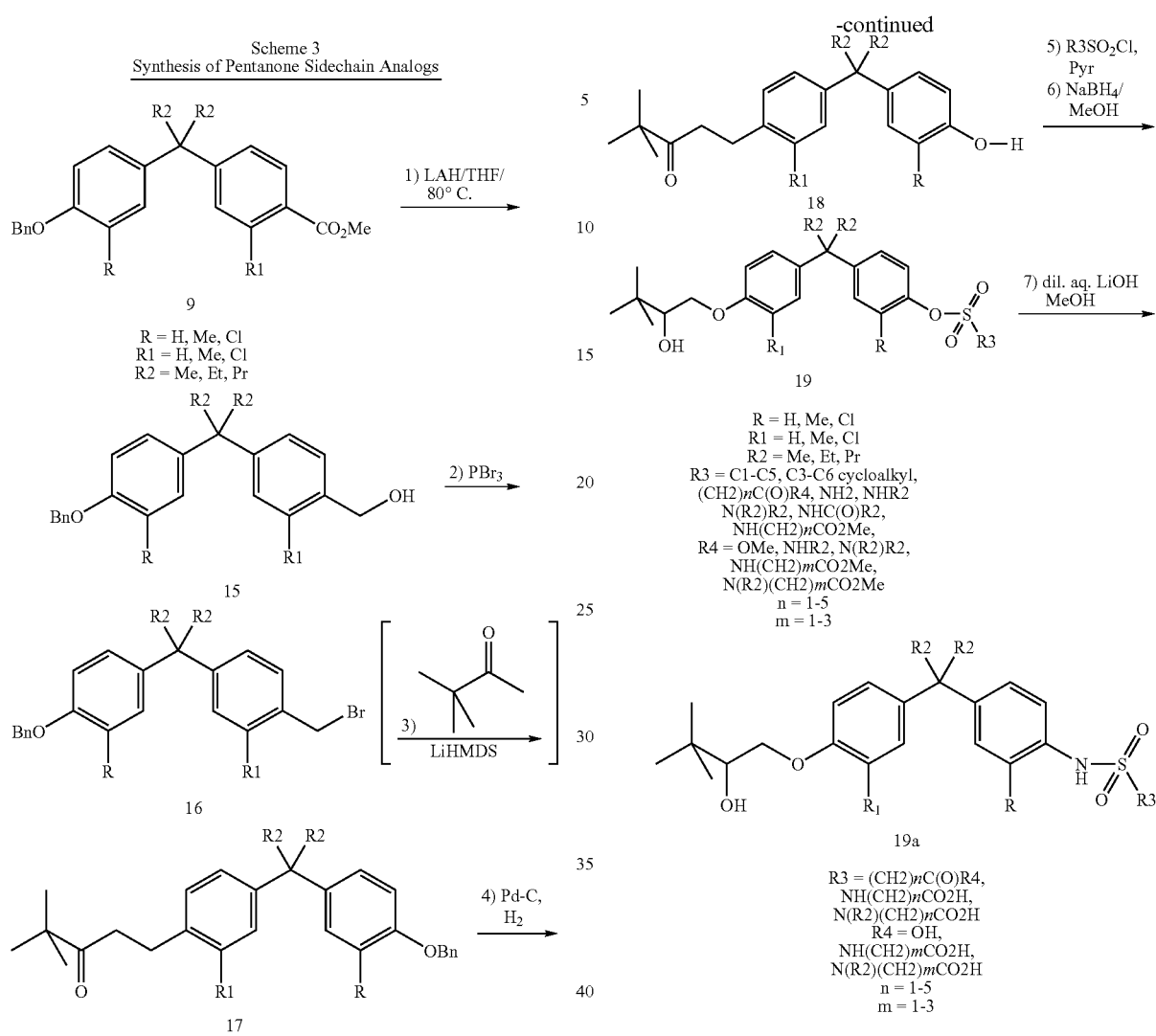
Scheme 4
Synthesis of Pentanone/Sulfonamide Analogs
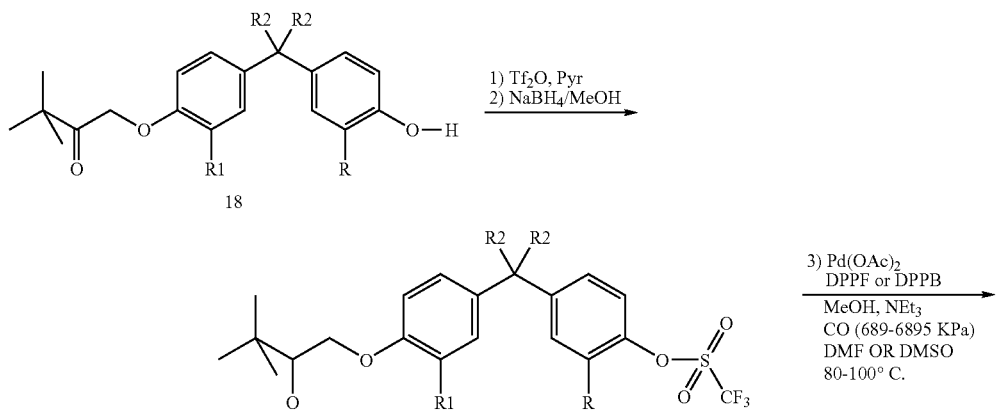

-continued
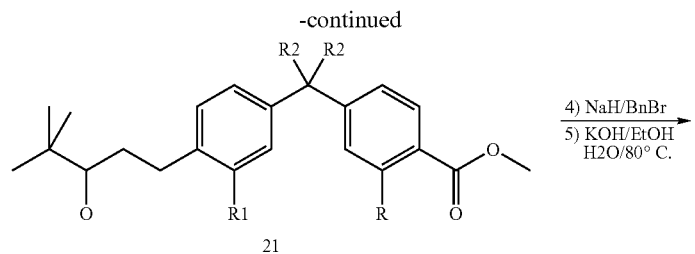
21
4) NaH/BnBr
5) KOH/EtOH
H2O/80° C.
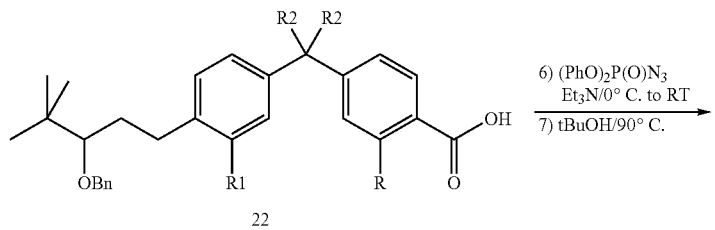
22
6) (PhO)$_2$P(O)N$_3$
Et$_3$N/0° C. to RT
7) tBuOH/90° C.
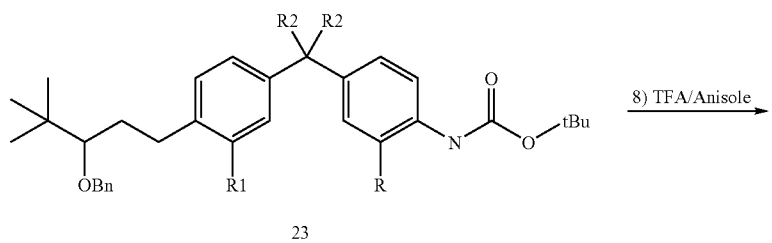
23
8) TFA/Anisole
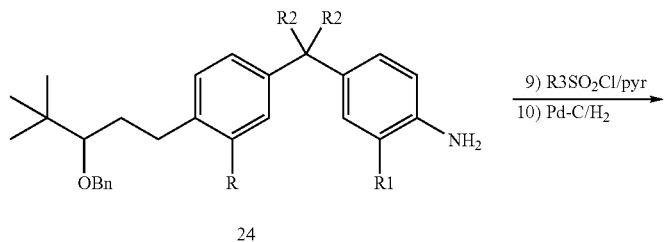
24
9) R3SO$_2$Cl/pyr
10) Pd-C/H$_2$
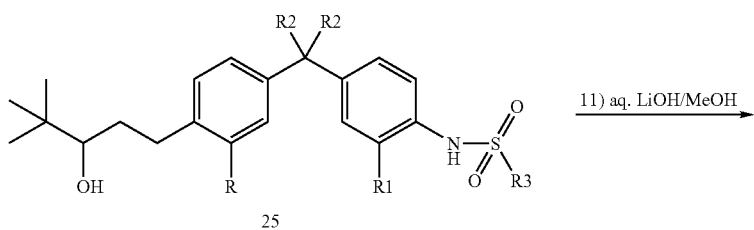
25
11) aq. LiOH/MeOH
R = H, Me, Cl
R1 = H, Me, Cl
R2 = Me, Et, Pr
R3 = C1-C5, C3-C6 cycloalkyl,
(CH2)$n$C(O)R4, NH2, NHR2
N(R2)R2, NHC(O)R2,
NH(CH2)$n$CO2Me,
N(R2)(CH2)$n$CO2Me,
R4 = OMe, NHR2, N(R2)R2,
NH(CH2)$m$CO2Me,
N(R2)(CH2)$m$CO2Me
n = 1-5
m = 1-3

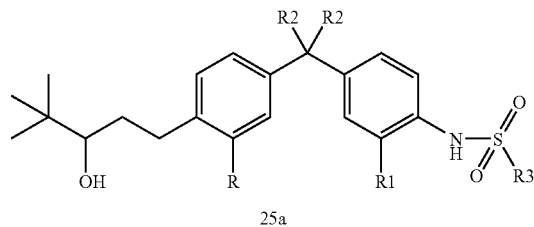
25a
R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1-5
m = 1-3
Scheme 5
Synthesis of Methylated Pinacolol Sidechain-Sulfonamides
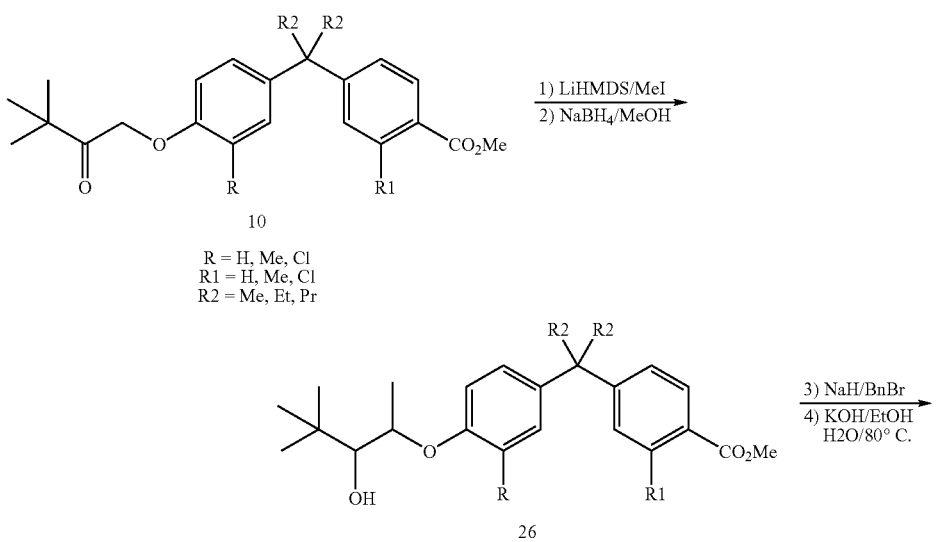
R = H, Me, Cl
R1 = H, Me, Cl
R2 = Me, Et, Pr
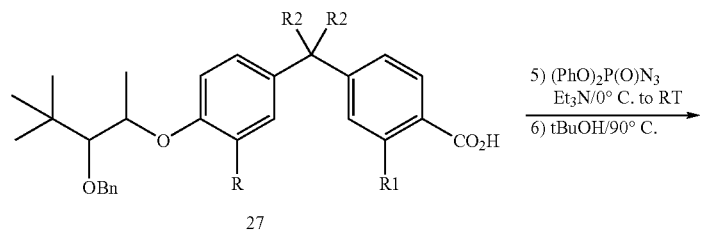
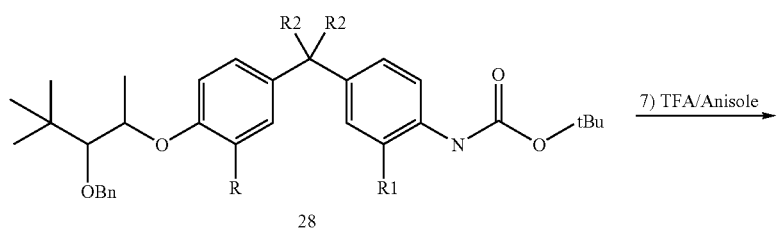

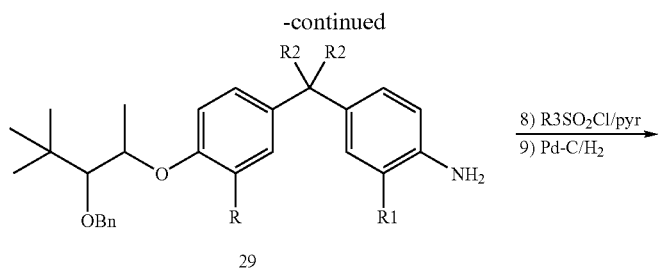
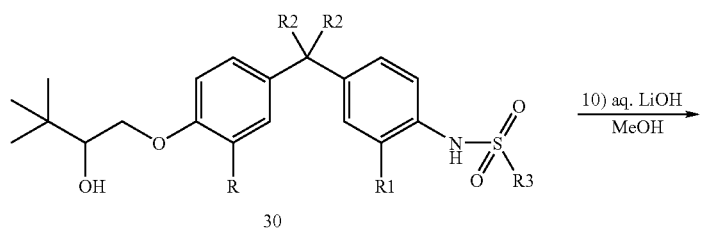
R = H, Me, Cl
R1 = H, Me, Cl
R2 = Me, Et, Pr
R3 = C1-C5, C3-C6 cycloalkyl,
(CH2)nC(O)R4, NH2, NHR2
N(R2)R2, NH(CH2)nCO2Me,
N(R2)(CH2)nCO2Me,
R4 = OMe, NHR2, N(R2)R2,
NH(CH2)mCO2Me,
N(R2)(CH2)mCO2Me
n = 1-5
m = 1-3
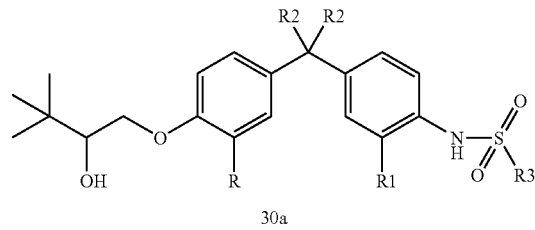
R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1-5
m = 1-3
Scheme 6
Synthesis of Unsymmetrical Central Linked Phenylalkyl-Phenyl Scaffold
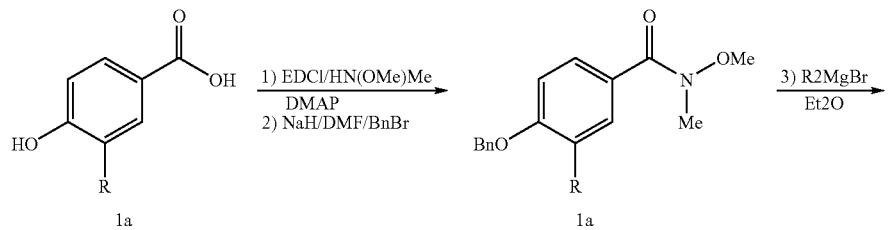
R = H, Me, Cl

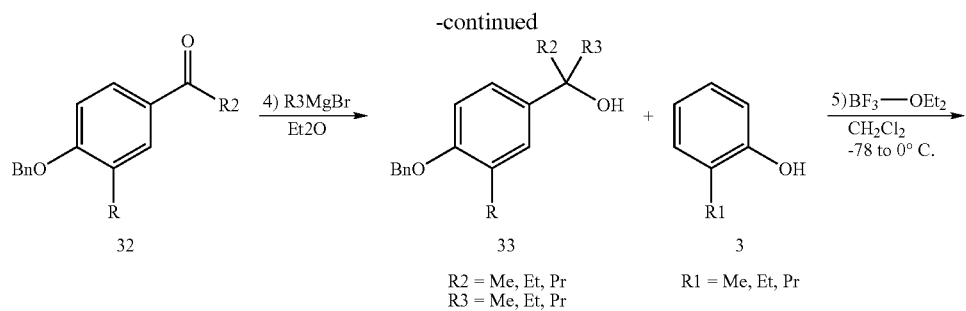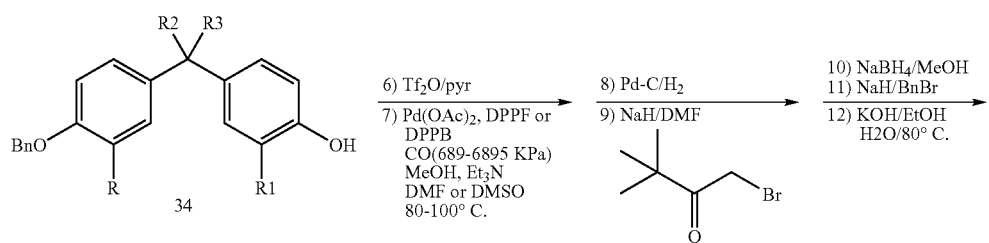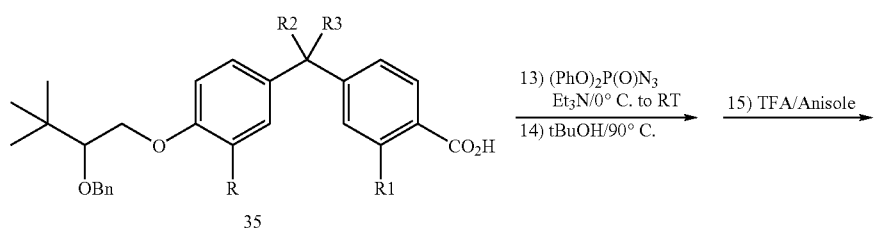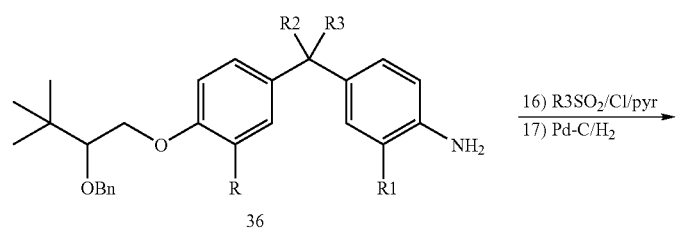

-continued

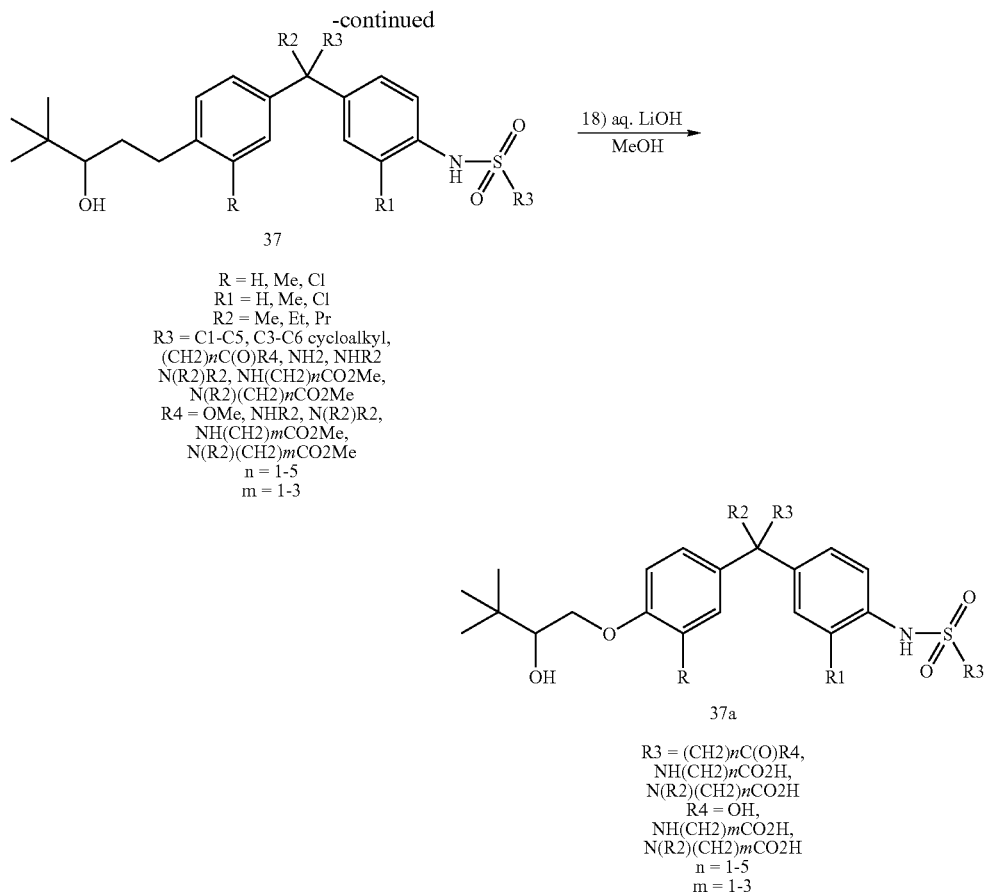

37

R = H, Me, Cl
R1 = H, Me, Cl
R2 = Me, Et, Pr
R3 = C1-C5, C3-C6 cycloalkyl,
(CH2)nC(O)R4, NH2, NHR2
N(R2)R2, NH(CH2)nCO2Me,
N(R2)(CH2)nCO2Me
R4 = OMe, NHR2, N(R2)R2,
NH(CH2)mCO2Me,
N(R2)(CH2)mCO2Me
n = 1-5
m = 1-3

37a

R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1-5
m = 1-3

-continued

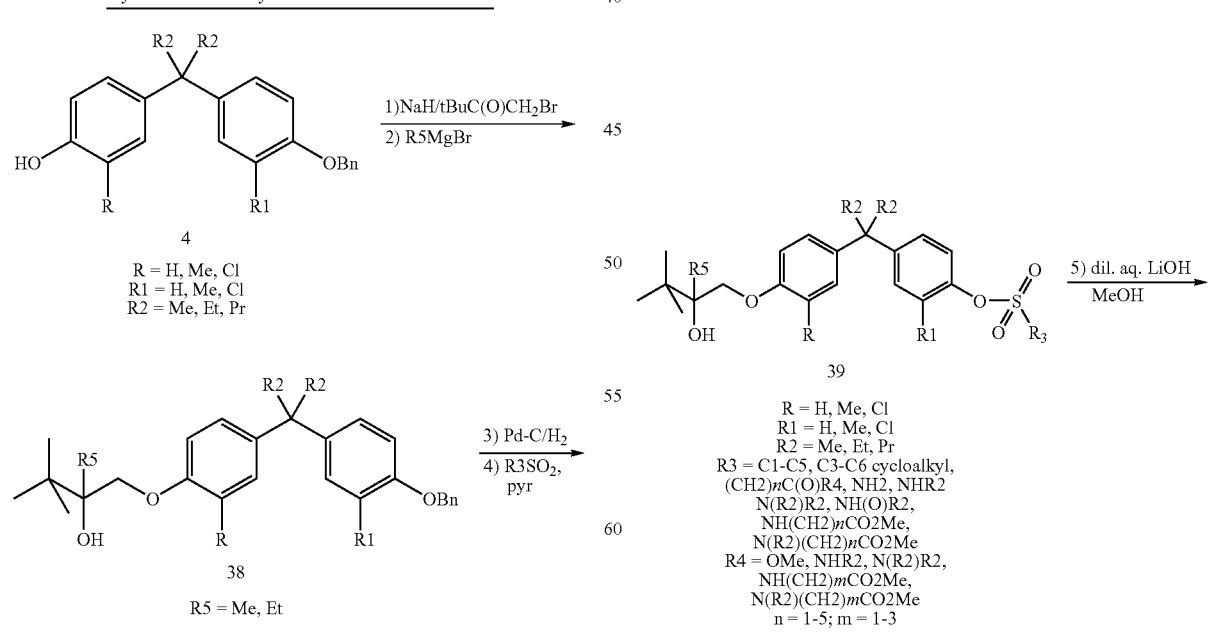

Scheme 7
Synthesis of Tertiary Alcohol-Sulfonate Sidechain

4

R = H, Me, Cl
R1 = H, Me, Cl
R2 = Me, Et, Pr

38

R5 = Me, Et

39

R = H, Me, Cl
R1 = H, Me, Cl
R2 = Me, Et, Pr
R3 = C1-C5, C3-C6 cycloalkyl,
(CH2)nC(O)R4, NH2, NHR2
N(R2)R2, NH(O)R2,
NH(CH2)nCO2Me,
N(R2)(CH2)nCO2Me
R4 = OMe, NHR2, N(R2)R2,
NH(CH2)mCO2Me,
N(R2)(CH2)mCO2Me
n = 1-5; m = 1-3

-continued
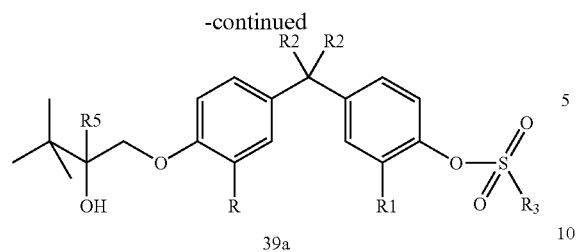
39a
R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1-5
m = 1-3
Scheme 8
Synthesis of Tertiary Alcohol-Sulfonamide Sidechain
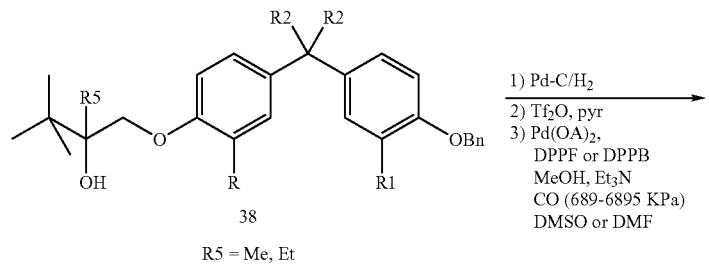
38
R5 = Me, Et
1) Pd-C/H$_2$
2) Tf$_2$O, pyr
3) Pd(OA)$_2$,
   DPPF or DPPB
   MeOH, Et$_3$N
   CO (689-6895 KPa)
   DMSO or DMF
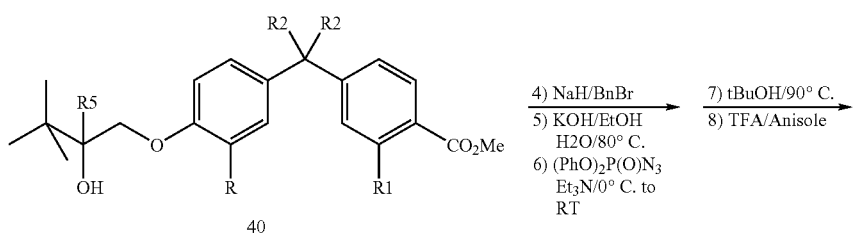
40
4) NaH/BnBr
5) KOH/EtOH
   H2O/80° C.
6) (PhO)$_2$P(O)N$_3$
   Et$_3$N/0° C. to RT
7) tBuOH/90° C.
8) TFA/Anisole
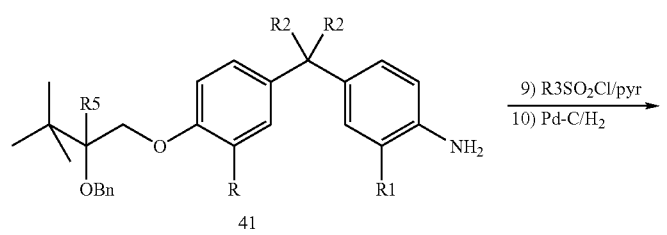
41
9) R3SO$_2$Cl/pyr
10) Pd-C/H$_2$

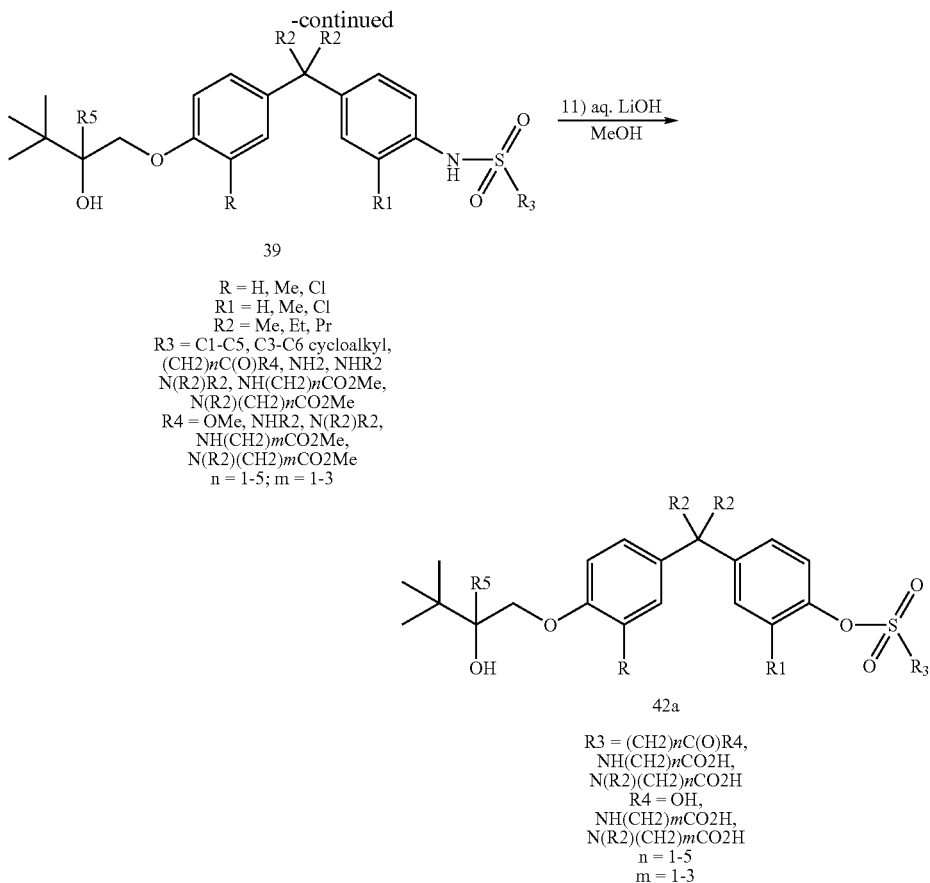
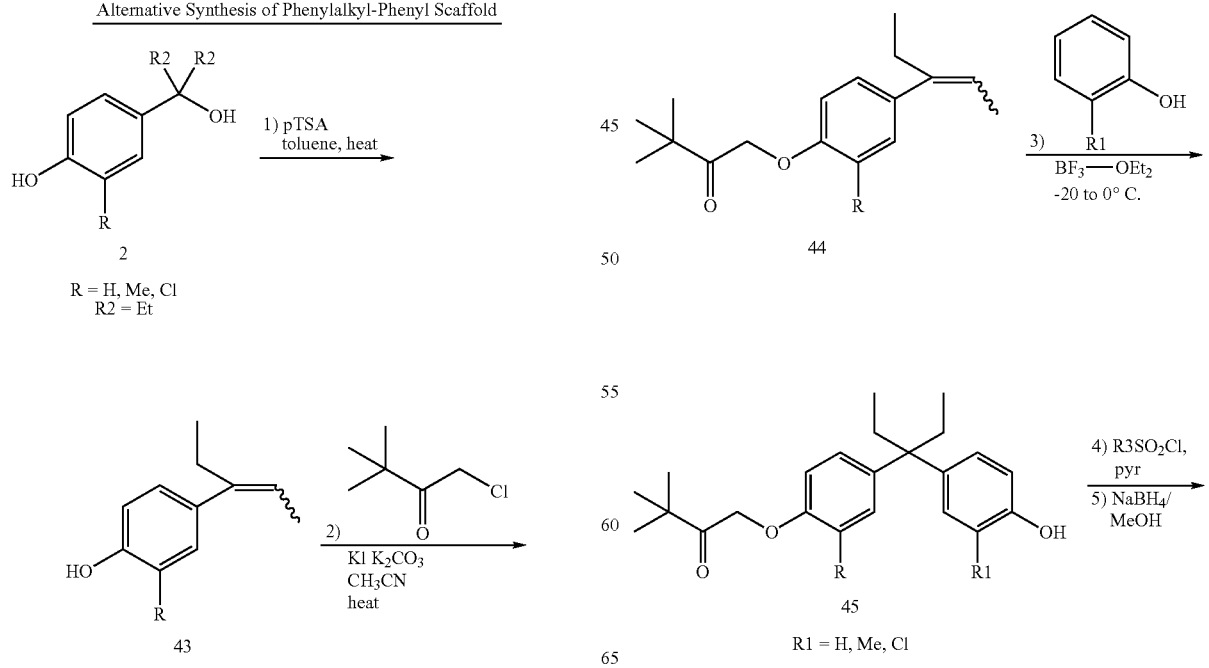
Scheme 9
Alternative Synthesis of Phenylalkyl-Phenyl Scaffold -continued

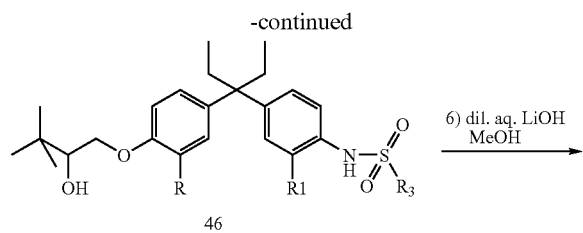

46

R = H, Me, Cl
R1 = H, Me, Cl
R2 = Me, Et, Pr
R3 = C1-C5, C3-C6 cycloalkyl,
(CH2)nC(O)R4, NH2, NHR2
N(R2)R2, NHC(O)R2,
NH(CH2)nCO2Me,
N(R2)(CH2)nCO2Me
R4 = OMe, NHR2, N(R2)R2,
NH(CH2)mCO2Me,
N(R2)(CH2)mCO2Me
n = 1-5
m = 1-3

6) dil. aq. LiOH
MeOH
→

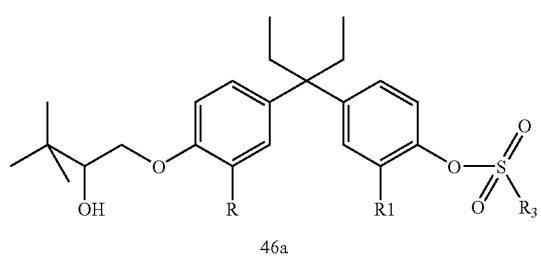

46a

R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1-5
m = 1-3

Scheme 10
Synthesis of Pentynol- Sulfonate Analogs

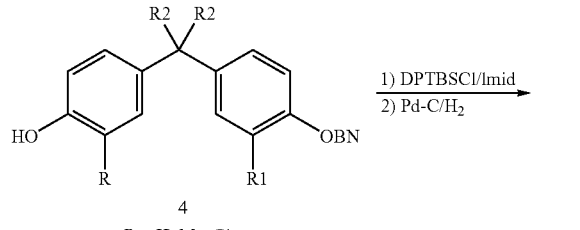

4

R = H, Me, Cl
R1 = H, Me, Cl
R2 = Me, Et, Pr

1) DPTBSCl/Imid
2) Pd-C/H2
→

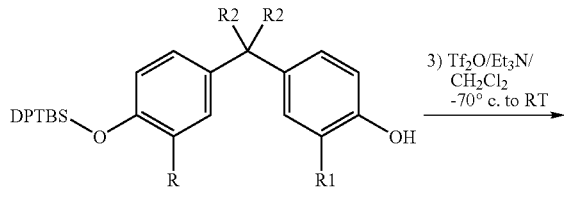

47

R = H, Me, Cl
R1 = H, Me, Cl
R2 = Me, Et, Pr

3) Tf2O/Et3N/
CH2Cl2
-70° c. to RT
→

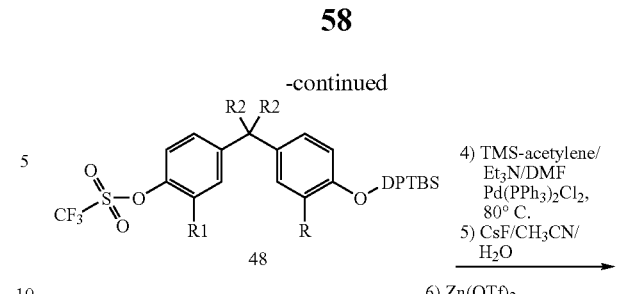

48

4) TMS-acetylene/
Et3N/DMF
Pd(PPh3)2Cl2,
80° C.
5) CsF/CH3CN/
H2O
→

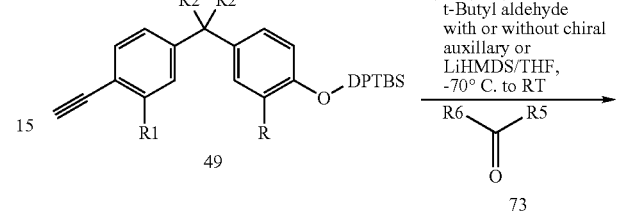

49

6) Zn(OTf)2,
t-Butyl aldehyde
with or without chiral
auxillary or
LiHMDS/THF,
-70° C. to RT

R6 R5
\\/
C
||
O

73
→

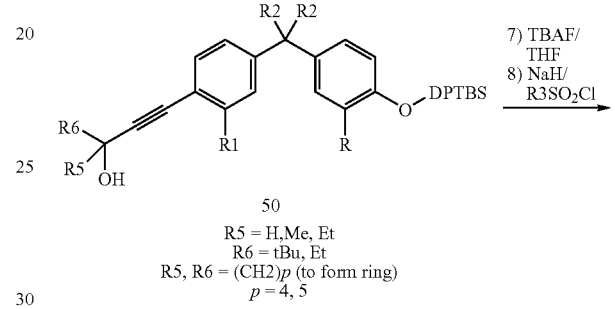

50

R5 = H, Me, Et
R6 = tBu, Et
R5, R6 = (CH2)p (to form ring)
p = 4, 5

7) TBAF/
THF
8) NaH/
R3SO2Cl
→

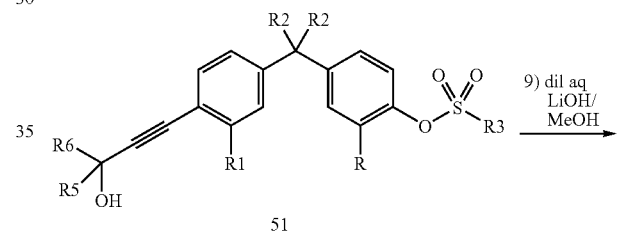

51

R = H, Me, Cl
R1 = H, Me, Cl
R2 = Me, Et, Pr
R3 = C1-C5, C3-C6
cycloalkyl,
(CH2)nC(O)R4, NH2,
NHR2,
N(R2)R2, NHC(O)R2,
NH(CH2)nCO2Me
R4 = OMe, NHR2,
N(R2)R2,
NH(CH2)mCO2Me
N(R2)(CH2)mCOD2Me
n = 1-5
m = 1-3

9) dil aq
LiOH/
MeOH
→

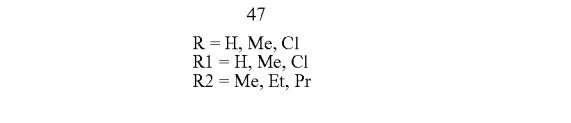

52

R3 =
(CH2)nC(O)R4,
NH(CH2)nCO2H,
N(R2)(CH2)nCO2H
R4 = OH,
NH(CH2)mCO2H,
N(R2)(CH2)mCO2H

Scheme 11
Synthesis of Cis-Pentenol-Sulfonate Analogs

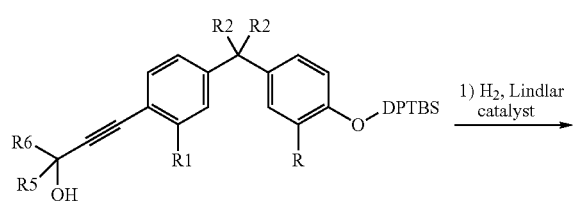

50
R5 = H, Me, Et
R6 = tBu, Et
R5, R6 = (CH2)p (to form ring)
p = 4, 5

1) H2, Lindlar catalyst

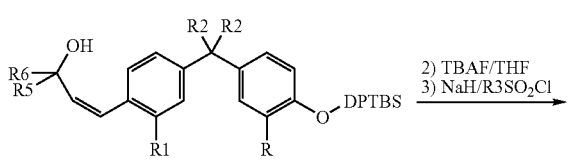

2) TBAF/THF
3) NaH/R3SO2Cl

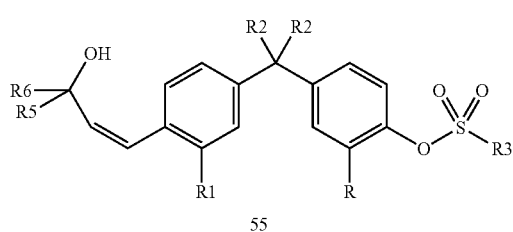

54
R = H, Me, Cl
R1 = H, Me, Cl
R2 = Me, Et, Pr
R3 = C1–C5, C3–C6 cycloalkyl,
(CH2)nC(O)R4, NH2, NHR2,
N(R2)R2, NHC(O)R2,
NH(CH2)nCO2Me,
N(R2)(CH2)nCO2Me
R4 = OMe, NHR2, N(R2)R2,
NH(CH2)mCO2Me,
N(R2)(CH2)mCO2Me 4) dil. aq. LiOH
MeOH 55
R3 = (CH2)nC(O)R4,
NH(CH2)nCO2H,
N(R2)(CH2)nCO2H,
R4 = OH,
NH(CH2)mCO2H,
N(R2)(CH2)mCO2H
n = 1–5
m = 1–3

Scheme 12
Synthesis of Trans-Pentenol-Sulfonate Analogs

50
R5 = H, Me, Et

1) LiAlH4 or Red-Al

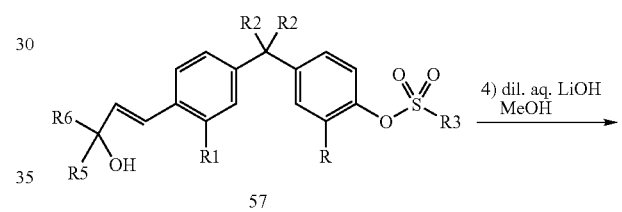

56

2) TBAF/THF
3) NaH/R3SO2Cl

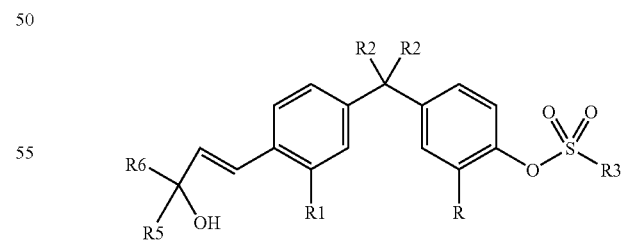

57
R = H, Me, Cl
R1 = H, Me, Cl
R2 = Me, Et, Pr
R3 = C1–C5, C3–C6 cycloalkyl,
(CH2)nC(O)R4, NH2, NHR2,
N(R2)R2, NHC(O)R2,
NH(CH2)nCO2Me,
N(R2)(CH2)nCO2Me
R4 = OMe, NHR2, N(R2)R2,
NH(CH2)mCO2Me,
N(R2)(CH2)mCO2Me 4) dil. aq. LiOH
MeOH 58
R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1–5

Scheme 13
Synthesis of Pentynol-Sulfonamide Analogs
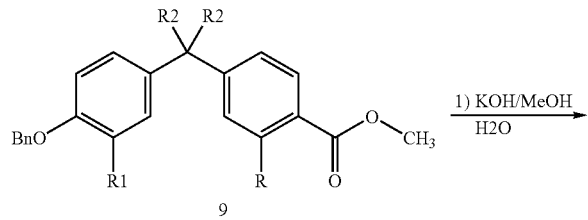
9
R = H, Me, Cl
R1 = H, Me, Cl
R2 = Me, Et, Pr
1) KOH/MeOH
H2O
→
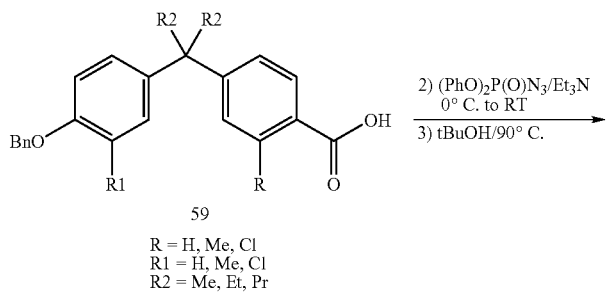
59
R = H, Me, Cl
R1 = H, Me, Cl
R2 = Me, Et, Pr
2) (PhO)₂P(O)N₃/Et₃N
0° C. to RT
3) tBuOH/90° C.
→
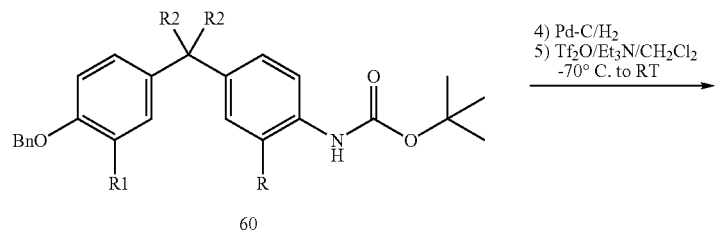
60
4) Pd-C/H₂
5) Tf₂O/Et₃N/CH₂Cl₂
−70° C. to RT
→
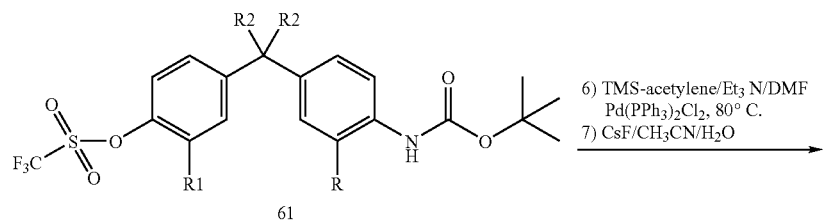
61
6) TMS-acetylene/Et₃N/DMF
Pd(PPh₃)₂Cl₂, 80° C.
7) CsF/CH₃CN/H₂O
→
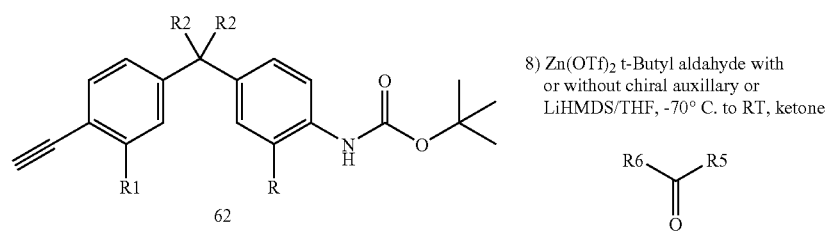
62
8) Zn(OTf)₂ t-Butyl aldahyde with
or without chiral auxillary or
LiHMDS/THF, −70° C. to RT, ketone -continued
73
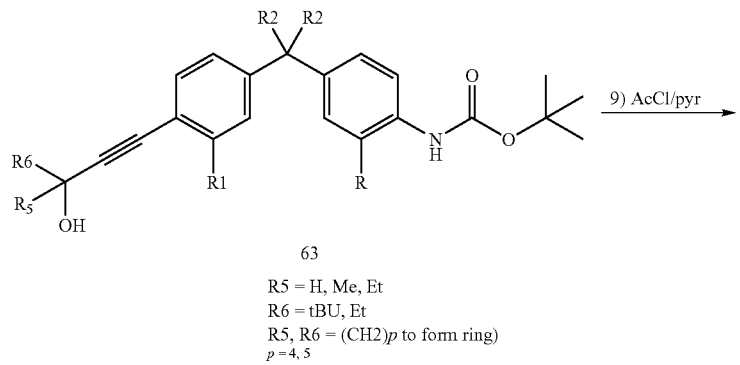
63
R5 = H, Me, Et
R6 = tBU, Et
R5, R6 = (CH2)p to form ring)
p = 4, 5
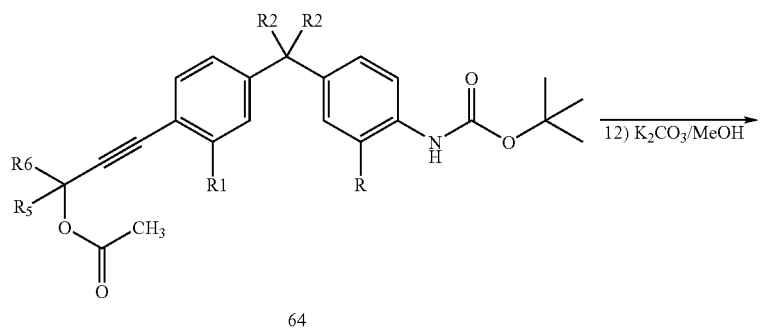
64
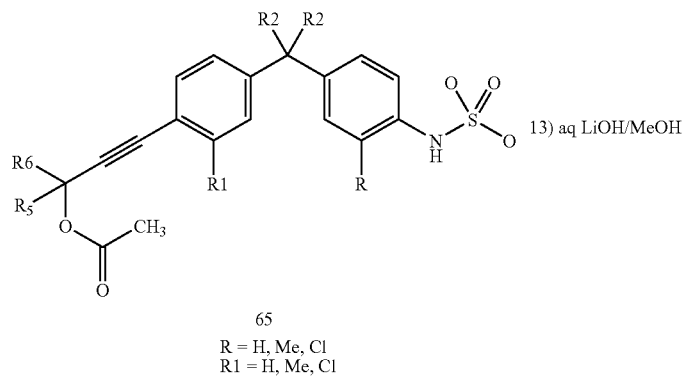
65
R = H, Me, Cl
R1 = H, Me, Cl
R2 = Me, Et, Pr
R3 = C1–C5, C3–C6 cycloalkyl,
(CH2)nC(O)R4, NH2, NHR2,
N(R2)R2, NHC(O)R2,
NH(CH2)nCO2Me,
N(R2)(CH2)nCO2Me
R4 = OMe, NHR2, N(R2)R2,
NH(CH2)mCO2Me,
N(R2)(CH2)mCO2Me
n = 1–5; m = 1–3

-continued
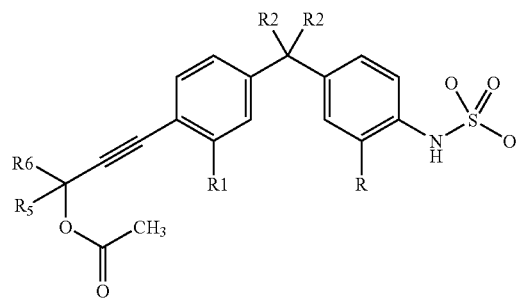
66
R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1–5
m = 1–3
Scheme 14
Synthesis of Cis-Pentenol_Sulfonamide Analogs
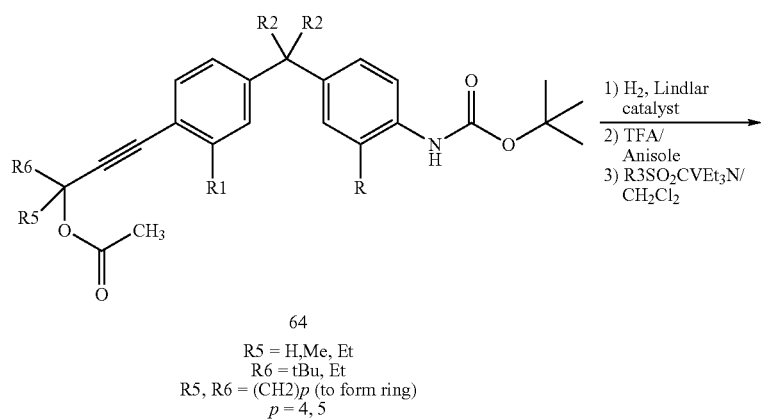
64
R5 = H, Me, Et
R6 = tBu, Et
R5, R6 = (CH2)p (to form ring)
p = 4, 5
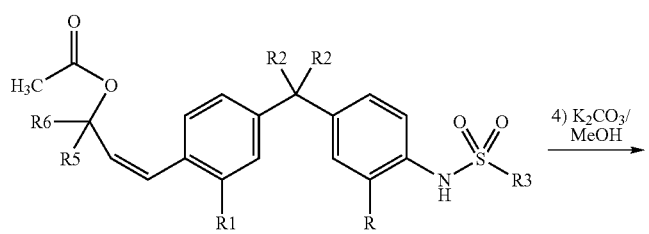
67

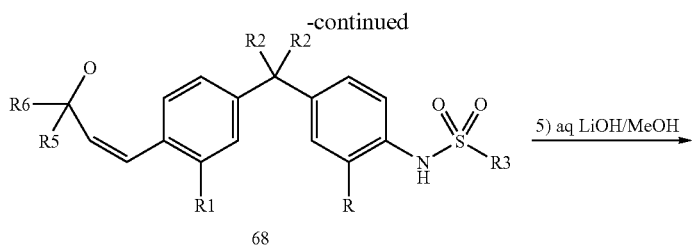

68
R = H, Me, Cl
R1 = H, Me, Cl
R2 = Me, Et, Pr
R3 = C1–C5, C3–C6 cycloalkyl,
(CH2)nC(O)R4,NH2, NHR2,
N(R2)R2, NHC(O)R2,
NH(CH2)nCO2Me,
N(R2)(CH2)nCO2Me
R4 = OMe, NHR2, N(R2)R2,
NH(CH2)mCO2Me,
N(R2)(CH2)mCO2Me
n = 1–5; m = 1–3

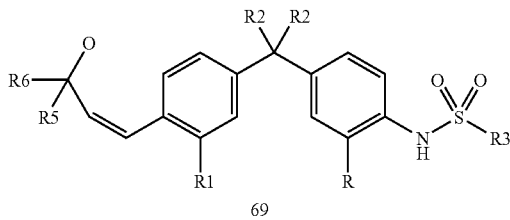

69
R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1–5
m = 1–3

Scheme 15
Synthesis of Trans-Pentenol-Sulfonamide Analogs

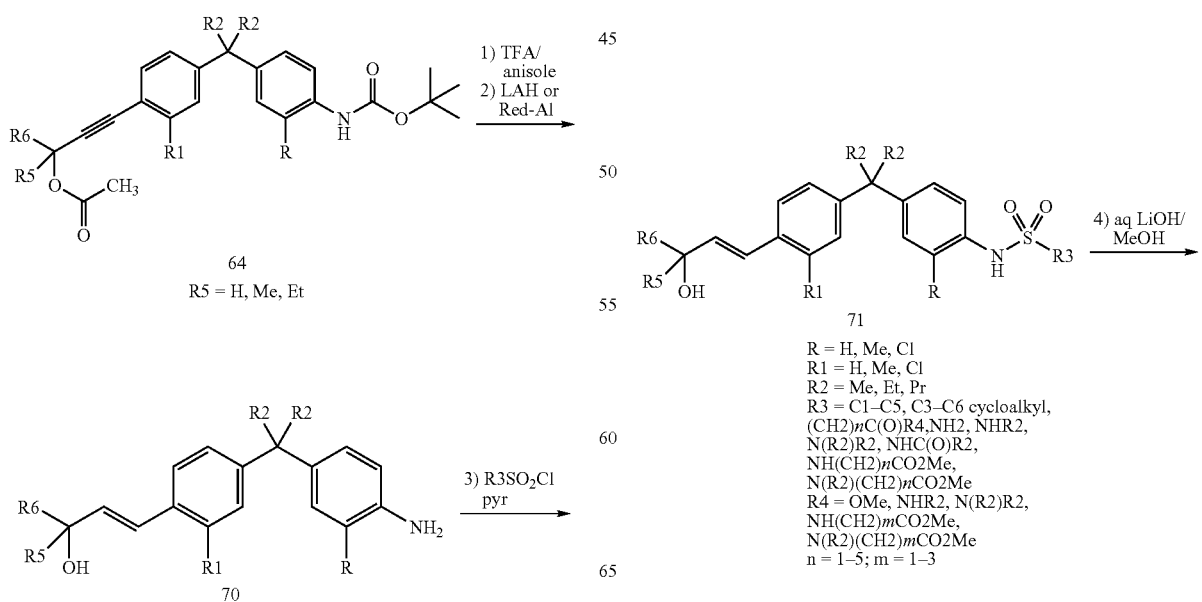

64
R5 = H, Me, Et

71
R = H, Me, Cl
R1 = H, Me, Cl
R2 = Me, Et, Pr
R3 = C1–C5, C3–C6 cycloalkyl,
(CH2)nC(O)R4,NH2, NHR2,
N(R2)R2, NHC(O)R2,
NH(CH2)nCO2Me,
N(R2)(CH2)nCO2Me
R4 = OMe, NHR2, N(R2)R2,
NH(CH2)mCO2Me,
N(R2)(CH2)mCO2Me
n = 1–5; m = 1–3

70

-continued

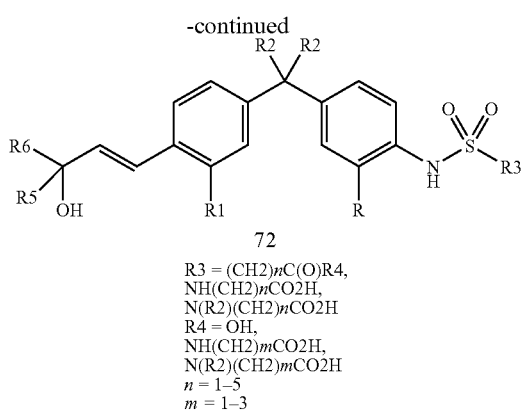

72

R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1–5
m = 1–3

Preparation of Phenylalkyl-Phenyl Sulfonates (Scheme 1).

A mixture of 3-substituted-4-hydroxy benzoic acid 1a and methanol is treated with HCl (gas) to yield methyl benzoate ester 1. Methyl benzoate ester 1 is reacted with excess alkyl magnesium bromide to produce tertiary alcohol 2. Tertiary alcohol 2 is converted to phenol 4 by reaction with O-benzyl-2-substituted phenol 3a and BF3-Et2O. O-benzyl-2-substituted phenol 3a is derived from reaction of 2-substituted phenol 3 with benzylbromide and NaH. Phenol 4 is reacted with NaH/1-bromopinacolone to give ketone 5. Ketone 5 is reduced with NaBH4 and hydrogenolyzed with Pd—C/H2 to give alcohol-phenol 6. Alcohol-phenol 6 is reacted with a sulfonyl chloride to give a sulfonyl derivative 7. Sulfonyl derivative 7 is hydrolyzed with aq. LiOH/MeOH to give sulfonyl-acid derivatives 7a.

Preparation of Phenylalkyl-Phenyl Sulfonamides (Scheme 2).

Phenol 4 is reacted with triflic anhydride/pyridine to give triflate 8 which is subjected to methoxycarbonylation with Pd(OAc)2, DPPF (or DPPB), CO (689-6895 KPa), methanol and triethylamine in either DMF or DMSO at 80-100° C. to yield methyl ester 2. Methyl ester 9 is subjected to palladium catalyzed hydrogenolysis and alkylated with NaH/1-bromopinacolone to give ketone 10. Ketone 10 is sequentially reacted with sodium borohydride/MeOH, NaH/BnBr, and potassium hydroxide/EtOH/H2O/80° C. to produce acid 11. Acid 11 is reacted with (PhO)2P(O)N3/Et3N and heated with t-BuOH at 90 C to give BOC-amine 12. Boc-amine 12 is reacted with TFA/anisole to give amine 13. Amine 13 is reacted with a sulfonyl chloride/pyridine and Pd—C/H2 to afford sulfonamide 14. Sulfonamide 14 is reacted with aq. LiOH/MeOH to give sulfonamide 14a.

Preparation of Pentanone Sidechain Analogs (Scheme 3).

Ester 9 is reduced with LAH to give benzyl alcohol 15. Benzyl alcohol 15 is converted to benzylic bromide 16 with PBr3 and alklylated with the lithium enolate of pinacolone to afford ketone 17. Ketone 17 is reacted with Pd—C/H2 to afford alcohol 18. Alcohol 18 is sulfonated with an alkyl sulfonyl chloride/pyridine and reduced with NaBH4/MeOH to give sulfonate 19. Sulfonate 19 is reacted with aq. LiOH/MeOH to produce sulfonamide 19a.

Preparation of Pentanone/Sulfonamide Analogs (Scheme 4).

Ketone phenol 18 is reacted with triflic anhydride/pyridine and NaBH4/MeOH to give triflate 20. Triflate 20 is subjected to methoxycarbonylation with Pd(OAc)2, DPPF (or DPPB), CO (689-6895 KPa), methanol and triethylamine in either DMF or DMSO at 80-100° C. to yield methyl ester 21. Methyl ester 21 is reacted with NaH/BnBr and potassium hydroxide/EtOH/H2O/80° C. to produce acid 22. Acid 22 is reacted with (PhO)2P(O)N3/Et3N and heated with t-BuOH at 90° C. to give BOC-amine 23. BOC-amine 23 is reacted with TFA/anisole to give amine 24. Amine 24 is reacted with a sulfonyl chloride/pyridine and Pd—C/H2 to give sulfonamide 25. Sulfonamide 25 is reacted with aq. LiOH/MeOH to give sulfonamide 25a.

Preparation of Methylated Pinacolol Sidechain-Sulfonamides (Scheme 5).

Ketone 10 is reacted with LiHMDS/MeI and NaBH4/MeOH to give ester 26. Ester 26 is reacted with KOH/EtOH/H2O/80° C., (PhO)2P(O)N3/Et3N and heated with t-BuOH at 90° C. to give BOC-amine 28. BOC-amine 28 is reacted with TFA/anisole to give amine 29. Amine 29 is reacted with a sulfonyl chloride/pyridine and Pd—C/H2 to give sulfonamide 30. Sulfonamide 30 is reacted with aq. LiOH/MeOH to afford sulfonamide 30a.

Preparation of Unsymmetrical Central Link Phenylalkyl-Phenyl Scaffold (Scheme 6).

3-Substituted-4-hydroxy benzoic acid 1a is reacted with EDCI/HN(OMe)Me/DMAP and NaH/BnBr to give amide 31. Amide 31 is reacted sequentially with a R2MgBr and R3MgBr to give alcohol 33. Alcohol 33 is treated with phenol 3 and BF3-OEt2 to give phenol 34. Phenol 34 is sequentially reacted with: 1) triflic anhydride/pyridine; 2) Pd(OAc)2, DPPF (or DPPB), CO (689-6895 KPa), methanol and triethylamine in either DMF or DMSO at 80-100° C.; 3) Pd—C/H2; 4) NaH/1-bromopinacolone; 5) NaBH4/MeOH; 6) NaH/BnBr; and 7) KOH/EtOH/H2O/80° C. to give acid 35. Acid 35 is reacted with (PhO)2P(O)N3/Et3N, heated with t-BuOH at 90° C., and TFA/anisole to give amine 36. Amine 36 is reacted with a sulfonyl chloride/pyridine and Pd—C/H2 to afford sulfonamide 37. Sulfonamide 37 is reacted with aq. LiOH/MeOH to give sulfonamide 37a.

Preparation of Tertiary Alcohol-Sulfonate Sidechain (Scheme 7).

Phenol 4 is reacted with NaH/1-bromopinacolone and R5MgBr to give alcohol 38 Alcohol 38 is treated with Pd—C/H2 and a sulfonyl chloride/pyridine to give sulfonate 39 Sulfonamide 39 is reacted with aq. LiOH/MeOH to give sulfonamide 39a.

Preparation of Tertiary Alcohol-Sulfonamide Sidechain (Scheme 8).

Alcohol 38 is reacted with Pd—C/H2, triflic anhydride/pyridine and Pd(OAc)2, DPPF (or DPPB), CO (689-6895 KPa), methanol and triethylamine in either DMF or DMSO at 80-100° C. to give ester 40. Ester 40 is reacted sequentially with: 1) NaH/BnBr; 2) KOH/EtOH/H2O; 3) (PhO)2P(O)N3/Et3N; 4) heated with t-BuOH at 90° C.; and 5) TFA/anisole to give amine 41. Amine 41 is reacted with a sulfonyl chloride/pyridine and Pd—C/H2 to afford sulfonamide 42. Sulfonamide 42 is treated with aq. LiOH/MeOH to give sulfonamide-acids 42a.

Alternative Preparation of Phenylalkyl-Phenyl Scaffold (Scheme 9).

Phenol 2 is reacted with pTSA/heat to give a mixture of e/z olefin 43. Olefin 43 is reacted with 1-chloropinacolone/KI/K2CO3 to give ketone 44. Ketone 44 is reacted with a substituted phenol 3 and BF3-OEt3 to give phenol 45. Phenol 45 is reacted with a sulfonyl chloride/pyridine and NaBH4/MeOH to give sulfonate 46. Sulfonate 46 is reacted with aq. LiOH/MeOH to give sulfonate-acids 46a.

Preparation of Pentynol-Sulfonate Analogs (Scheme 10).

Phenol 4 is reacted with DPTBSCl/mid and Pd—C/H2 to give silyl ether-phenol 47. Silyl ether-phenol 47 is reacted with triflic anhydride/pyridine to give triflate 48. Triflate 48 is reacted with TMS-acetylene/Et3N/Pd(PPh3)2Cl2 at 80° C. and CsF/H2O to give acetylene 49. Acetylene 49 is treated with Zn(OTf)2/t-butyl aldehyde/chiral auxiliary (with or without) to give alcohol 50. Alternatively, acetylene 49 is reacted with LiHMDS/ketone 73 to give alcohol 50. Alcohol 50 is reacted with TBAF and NaH/R3SO2Cl to give sulfonate 51. Sulfonate 51 is reacted with aq. LiOH/MeOH to give sulfonate-acids 52.

Preparation of Cis-Pentenol-Sulfonate Analogs (Scheme 11).

Alcohol 50 is reacted with Lindlar catalyst/H2 to give cis-olefin 53. Cis-olefin 53 is reacted with TBAF and NaH/R3SO2Cl to give sulfonate 54. Sulfonate 54 is reacted with dilute aq. LiOH/MeOH to give sulfonate-acids 55.

Preparation of Trans-Pentenol-Sulfonate Analogs (Scheme 12).

Alcohol 50 is reacted with LAH or Red-Al to give trans-olefin 56. Trans-olefin 56 is reacted with TBAF and NaH/a sulfonyl chloride to give sulfonate 57. Sulfonate 57 is reacted with dilute aq LiOH/MeOH to give sulfonate-acids 58.

Preparation of Pentynol-Sulfonamide Analogs (Scheme 13).

Ester 9 is reacted with KOH/MeOH to give acid 59. Acid 59 is treated with (PhO)2P(O)N3/Et3N and heated with t-BuOH at 90° C. to give Boc-amine 60. Boc-amine 60 is reacted with Pd—C/H2 and triflic anhydride/Et3N to give triflate 61. Triflate 61 is reacted with TMS-acetylene/Et3N/Pd(PPh3)2Cl2 at 80° C. and CsF/H2O to give acetylene 62. Acetylene 62 is treated with Zn(OTf)2/t-butyl aldehyde/chiral auxiliary (with or without) to give alcohol 63. Alternatively, acetylene 62 is reacted with LiHMDS/ketone 73 to give alcohol 63. Alcohol 63 is reacted with acetyl chloride to give acetate 64. Acetate 64 is reacted with TFA/anisole, a sulfonyl chloride/Et3N, and K2CO3/MeOH to give amine 65. Amine 65 is reacted with aq LiOH/MeOH to give a sulfonamide 66.

Preparation of Cis-Pentenol-Sulfonamide Analogs (Scheme 14).

Acetate 64 is reacted with Lindlar's catalyst/H2, TFA/anisole, and a sulfonyl chloride/Et3N to give sulfonamide 67. Sulfonamide 67 is reacted with K2CO3/MeOH to give alcohol 68. Alcohol 68 is reacted with aq. LiOH/MeOH to give sulfonamide 69.

Preparation of Trans-Pentenol-Sulfonamide Analogs (Scheme 15).

Acetate 64 is reacted with TFA/anisole and LAH to give trans-pentenol 70. Trans-pentenol is reacted with a sulfonyl chloride/Et3N to give sulfonamide 71. Sulfonamide 71 is reacted with aq. LiOH/MeOH to give sulfonamide 72.

EXAMPLES

General Experimental Conditions

The starting material/intermediate is the compound from the immediate preceding experimental unless otherwise indicated.

All reactions are performed under nitrogen/argon atmosphere, in a stirred reaction vessel, and at room temperature unless indicated otherwise.

Concentration is performed from RT to about 70° C. under vacuum (0.05 to 1 mm Hg).

Unless otherwise indicated, the organic layer is MgSO4/Na2SO4 dried is defined as stirring the solution with a desiccant for 5-15 m and filtering off the dessicant to give an anhydrous filtrate.

For analogous multi-step reaction procedures, the yield is given either for the ultimate step or overall multi-steps as indicated.

Solutions are "concentrated" at a range of 25-75° C. with reduced pressure. in-vacuo −25-75° C.; 0.05 to 1 mm Unless otherwise indicated, "the residue is chromatographed" is defined as silica gel chromatography of residue with moderate nitrogen pressure (flash chromatography) or a medium pressure chromatography systems using a silica gel to crude product ratio of ~10-100.

Thin layer chromatography is performed with silica gel plates with UV and/or appropriate staining solution.

NMR spectra are obtained with either 300 or 400 mHz spectrometer.

NMR—denotes NMR spectrum is consistent with assigned structure.

HRMS—high resolution mass spectrum

ES-MS—electrospray mass spectrum

Abbreviations:
- Aq—aqueous
- d—day
- eq—equivalent
- h—hour
- m—minute
- satd—saturated
- disp—dispersion
- quant—quantitative
- rt for retention time (both small caps to minimize confusion with RT)
- RT—room temperature Chemical Definitions:
- BBr3—boron tribromide
- BF3-OEt2—boron trifluoride etherate
- BnBr—benzyl bromide
- CH2Cl2—dichloromethane
- CH3CN—acetonitrile
- CO-carbon monoxide
- Dess-Martin reagent—1,1,1-tris(acetyloxy)-1,1-dihydro-1,2-benziodoxol-3-(1H)-one
- DIBAlH—Diisobutyl Aluminum Hydride
- DMAP—4-(dimethylamino)pyridine
- DMF—N,N-dimethylformamide
- DMSO—dimethylsulfoxide
- DPPB—1,4-bis(diphenylphosphino)butane
- DPPF—dichloro[1,1'-bis(diphenylphosphino)ferrocene
- EDCI—3-Ethyl-1-[3-(dimethylamino)propyl]carbodiimide hydrochloride
- Et3N—triethylamine
- EtMgBr—ethyl magnesium bromide
- EtOAc—ethyl acetate
- EtOH—ethanol
- H2NCH2CO2Me—methyl glycinate
- Hept—heptane
- Hex—hexanes
- HN(OMe)Me—N-methyl-O-methyl hydroxylamine
- HNMe2—dimethyl amine
- HATU—O-(7-azabenzotriazol-1-yl)-N,N,N',N'-tetramethyluronium hexafluorophosphate
- HOAT—7-aza-1-hydroxybenzotriazole
- HOBT—1-hydroxybenzotriazole
- K2CO3—potassium carbonate
- KOH—potassium hydroxide LAH—lithium aluminum hydride
LiHMDS—lithium hexamethyldisilazide
mCPBA—meta-chloroperbenzoic acid
MeI—methyl iodide
MeOH—methanol
NaBH4—sodium borohydride
MgSO4—magnesium sulfate
NaH—sodium hydride
NaHCO3—sodium bicarbonate
NaI—sodium iodide
Na2SO4—sodium sulfate
NH4Cl—ammonium chloride
NMO—4-methylmorpholine N-oxide
NMP—N-methylpyrrolidin-2-one
Na—S—R3—sodium alkylmercaptide
PBr3—phosphorus tribromide
Pd(DPPF)—palladium dichloro[1,1'-bis(diphenylphosphino)ferrocene
Pd(OAc)2—palladium (II) acetate
Pd(TPP)4—palladium tetrakistriphenylphosphine
Pd—C—palladium on carbon
(PhO)2P(O)N3—diphenyl phosphorus azide
pTSA—para-toluenesulfonic acid
Pyr—pyridine
Red-Al—sodium bis(2-methoxyethoxy)aluminum hydride
R2MgBr—alkyl magnesium bromide
R3MgBr—alkyl magnesium bromide
R5MgBr—alkyl magnesium bromide
R2S(O)2NH2—alkylsulfonamide
TBAF—tetrabutylammonium fluoride
TBSCl—tert-butyldimethylsilyl chloride
tBuC(O)CH2Br—1-bromopinacolone
Tf2O—triflic anhydride
TFA—trifluoroacetic acid
THF—tetrahydrofuran
TPAP—tetrapropylammonium perruthenate
Zn(OTf)2—zinc trifluoromethane sulfonate.

Example 1

Preparation of 3'-[4-(2-hydroxy-3,3-dimethylbutoxy)-3-methylphenyl]-3'-[4-(methanesulfonyloxy)-3-methylphenyl]pentane

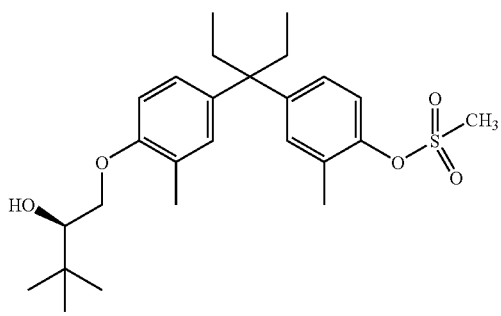

A. 3',3'-Bis[4-hydroxy-3-methylphenyl]pentane

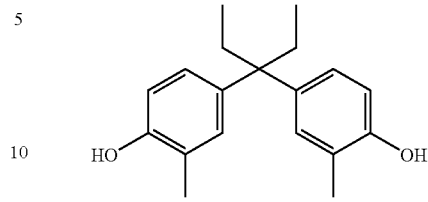

To a mixture of o-cresol (196 g, 1.81 mol) and 3-pentanone (60 ml, 0.57 mol) is added MeSO3H (45 ml, 0.69 mol) and stirred for 3 d. The reaction is carefully basified to pH 8 with satd Na2CO3 and extracted with EtOAc. The organic layer is washed with water (6×500 ml), Na2SO4 dried, concentrated, chromatographed (2 kg SiO2, Hex to 80% EtOAc/Hex), and triturated with Hex to give the title compound as a white solid (100 g, 61%).

NMR 400 mHz(DMSO): δ 0.49 (t, J=7.3 Hz, 6H), 1.91 (q, J=7.3 Hz, 4H), 2.02 (s, 6H), 6.61 (d, J=8.3 Hz, 2H), 6.73 (d, J=8.3 Hz, 2H), 6.76 (s, 2H), 8.94 (s, 2H).

High Res. EI-MS: 284.1794; calc. for $C_{19}H_{24}O_2$: 284.1776

B. 3'-[4-(2-Oxo-3,3-dimethylbutoxy)-3-methylphenyl)]-3'-[4-hydroxy-3-methylphenyl]pentane

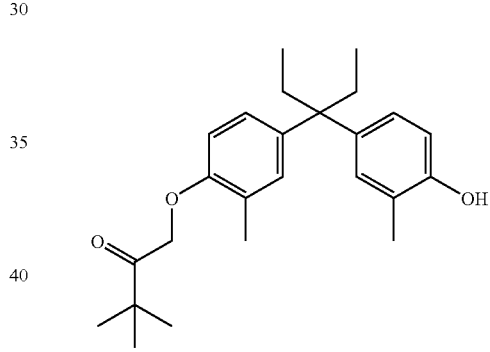

To a mixture of 60% NaH disp (8.0 g, 200 mmol) and DMF (600 ml) is added 3,3-bis[4-hydroxy-3-methylphenyl]pentane (56.88 g, 200 mmol) and stirred for 2 h. The reaction is added 3,3-dimethyl-1-bromo-2-butanone (26.93 ml, 200 mmol) dropwise and stirred overnight. The solvent is removed in-vacuo. The resulting residue is added EtOAc/water (800 ml/200 ml), acidified to pH 3 with 5N HCl, and partitioned. The organic layer is washed with water (2×), brine, Na2SO4 dried, concentrated, and chromatographed (3 kg SiO2, Hex to 15% EtOAc/Hex) to give the title compound as a white solid (35 g, 46%).

NMR (300 mHz, DMSO): δ 0.52 (t, J=7.3 Hz, 6H), 1.16 (s, 9H), 1.95 (q, J=7.3 Hz, 4H), 2.04 (s, 3H), 2.12 (s, 3H), 5.05 (s, 2H), 6.57 (d, J=9.1 Hz, 1H), 6.63 (d, J=8.1 Hz, 1H), 6.81 (m, 2H), 8.97 (s, 1H).

ES-MS: 400(M+NH4).

C. 3'-[4-(2-Hydroxy-3,3-dimethylbutoxy)-3-methylphenyl]-3'-[4-hydroxy-3-methylphenyl]pentane To a 0° C. mixture of 3'-[4-(2-oxo-3,3-dimethylbutoxy)-3-methylphenyl)]-3'-[4-hydroxy-3-methylphenyl]pentane (7.3 g, 19.1 mmol) and methanol (75 ml) is added NaBH4 (1.58 g, 42.6 mmol) in portions. After 2 h, the reaction is warmed to RT and stirred overnight. The reaction is quenched with 1N HCl and then concentrated in-vacuo. The mixture is partitioned between Et$_2$O/water. The organic layer is washed with water, Na$_2$SO$_4$ dried, and concentrated to give the title compound as a glassy solid (7.2 g, 98%).

NMR

High Res. ES-MS: 402.3010; calc. for C$_{25}$H$_{40}$NO$_3$: 402.3008

D. 3'-[4-(2-Hydroxy-3,3-dimethylbutoxy)-3-methylphenyl]-3'-[4-methanesulfonyloxy-3-methylphenyl]pentane To a mixture of 3'-[4-(2-hydroxy-3,3-dimethylbutoxy)-3-methylphenyl]-3'-[4-hydroxy-3-methylphenyl]pentane (150 mg, 0.39 mmol) and DMF (1.5 ml) is added 60% NaH disp (16.4 mg, 0.41 mmol). After stirring for 5 m, the reaction is added mesyl chloride (33 ul, 0.43 mmol) and heated to 80° C. for 5 h. The reaction is concentrated in-vacuo and partitioned between Et$_2$O/water. The organic layer is Na$_2$SO$_4$ dried, concentrated, and chromatographed (MeCl$_2$ to 5% EtOAc/MeCl$_2$) to give the title compound as a glassy solid (100 mg, 55%).

NMR

High Res. ES-MS: 480.2799; calc. for C$_{26}$H$_{38}$O$_5$S+(NH$_4$): 480.2784

Examples 2 & 3

Preparation of enantiomers of isomers of 3'-[4-(2-hydroxy-3,3-dimethylbutoxy)-3-methylphenyl]-3'-[4-(methanesulfonyloxy)-3-methylphenyl]pentane

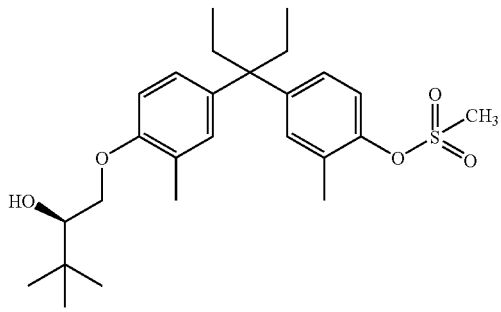

A racemate mixture of 3'-[4-(2-hydroxy-3,3-dimethylbutoxy)-3-methylphenyl]-3'-[4-(methanesulfonyloxy)-3-methylphenyl]pentane is chromatographed on (Chiralpak AD) to give isomer 1 (Example 2) of the title compound as an oil (22 mg, 36%) and isomer 2 (Example 3) of the title compound as an oil (20 mg, 34%).

Isomer 1 rt: 5.97 m (40% EPA/heptane)

NMR equivalent to Example 1.

High Res. ES-MS: 480.2765; calc. for C$_{26}$H$_{38}$O$_5$S+(NH$_4$): 480.2784

Isomer 2 rt: 8.20 m (40% IPA/heptane)

NMR equivalent to Example 1.

High Res. ES-MS: 480.2773; calc. for C$_{26}$H$_{38}$O$_5$S+(NH$_4$): 480.2784

Example 4

Preparation of 3'-[4-(2-oxo-3,3-dimethylbutoxy)-3-methylphenyl]-3'-[4-(methanesulfonyloxy)-3-methylphenyl]pentane

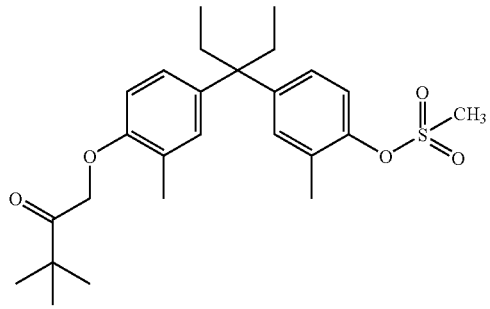

Using a procedure analogous to Example 1D, 3'-[4-(2-oxo-3,3-dimethylbutoxy)-3-methylphenyl]-3'-[4-(hydroxy)-3-methylphenyl]pentane (Example 1B) gives the title compound (1.68 g, 61%).

NMR

FAB-MS: 460.4(M+).

Example 5

Preparation of 3'-[4-(2-oxo-3,3-dimethylbutoxy)-3-methylphenyl]-3'-[4-(trifluoromethanesulfonyloxy)-3-methylphenyl]pentane

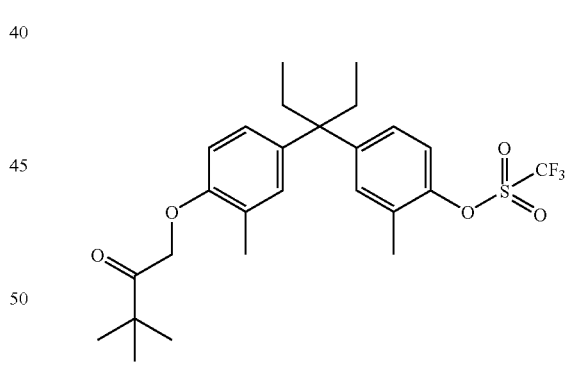

To a mixture of 3'-[4-(2-oxo-3,3-dimethylbutoxy)-3-methylphenyl]-3'-[4-hydroxy-3-methylphenyl]pentane (20 g, 52 mmol) and pyridine (30 ml) at 0° C. is added triflic anhydride (9.7 ml, 57 mmol). The reaction is warmed to RT and stirred overnight. The mixture is partitioned between Et$_2$O/1N HCl. The organic layer is washed with brine, Na$_2$SO$_4$ dried, concentrated, and chromatographed (hex to 10% EtOAc/hex) to give the title compound as an oil (26.3 g, 98%).

NMR

ES-MS: 532.5 (M+NH4).

Example 6

Preparation of 3'-[4-(2-hydroxy-3,3-dimethylbutoxy)-3-methylphenyl]-3'-[4-(trifluoromethanesulfonyloxy)-3-methylphenyl]pentane

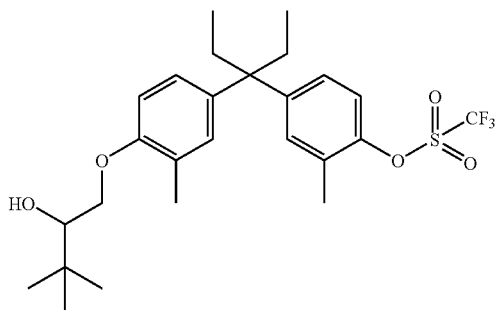

To a 0° C. mixture of 3'-[4-(2-oxo-3,3-dimethylbutoxy)-3-methylphenyl]-3'-[4-(trifluoromethanesulfonyloxy)-3-methylphenyl]pentane (25.5 g, 49.5 mmol) and MeOH (200 ml) is added NaBH$_4$ (2.63 g, 69.3 mmol) in portions. The reaction is warmed to RT, stirred overnight, and concentrated. The mixture is partitioned between Et$_2$O/1N HCl. The organic layer is washed with water, Na$_2$SO$_4$ dried, and concentrated to give the title compound as an oil (26 g, quant).

NMR

High Res. EI-MS, m/e: 516.2171; calc. for C$_{26}$H$_{35}$F$_3$O$_5$S: 516.2157

Example 7

Preparation of 3'-[4-(2-hydroxy-3,3-dimethylbutoxy)-3-methylphenyl]-3'-[4-(trifluoromethanesulfonyloxy)-3-methylphenyl]pentane

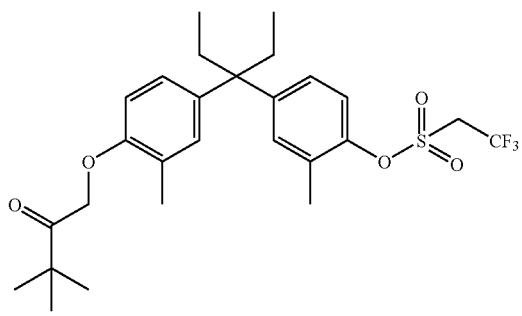

Using a procedure analogous to Example 1D, 3'-[4-(2-hydroxy-3,3-dimethylbutoxy)-3-methylphenyl]-3'-[4-(hydroxy)-3-methylphenyl]pentane gives the title compound (290 mg, 21%).

NMR

High Res. ES-MS: 551.2048; calc. for C$_{27}$H$_{35}$F$_3$O$_5$S+(Na): 551.2055

Example 8

Preparation of 3'-[4-(2-oxo-3,3-dimethylbutoxy)-3-methylphenyl]-3'-[4-(ethanesulfonyloxy)-3-methylphenyl]pentane

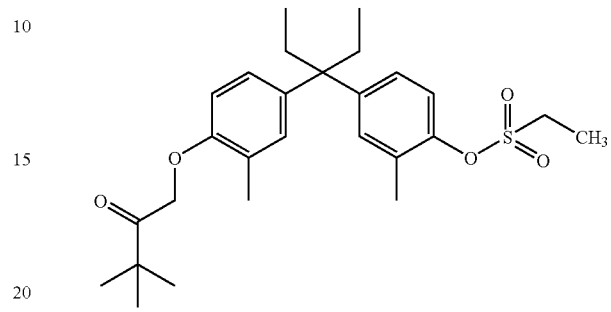

Using a procedure analogous to Example 1D, 3'-[4-(2-oxo-3,3-dimethylbutoxy)-3-methylphenyl]-3'-[4-(hydroxy)-3-methylphenyl]pentane gives the title compound (1.0 g, 81%).

NMR

High Res. ES-MS: 497.2334; calc. for C$_{27}$H$_{38}$O$_5$S+Na: 497.2338.

Example 9

Preparation of 3'-[4-(2-hydroxy-3,3-dimethylbutoxy)-3-methylphenyl]-3'-[4-(ethanesulfonyloxy)-3-methylphenyl]pentane

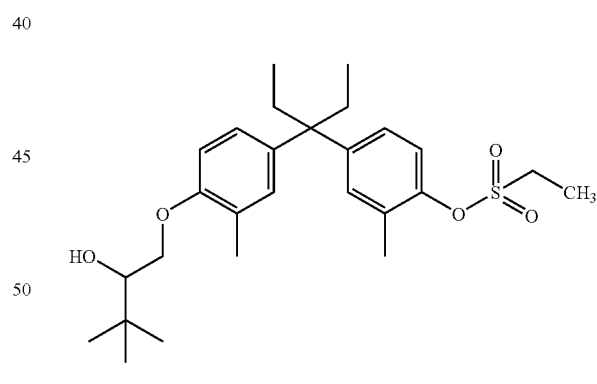

Using a procedure analogous to Example 1C, 3'-[4-(2-hydroxy-3,3-dimethylbutoxy)-3-methylphenyl]-3'-[4-(hydroxy)-3-methylphenyl]pentane gives the title compound (550 mg, quant).

NMR

High Res. ES-MS: 499.2508; calc. for C$_{27}$H$_{40}$O$_5$S+Na: 499.2494.

Example 10

Preparation of 3'-[4-(2-hydroxy-2-methyl-3,3-dimethylbutoxy)-3-methylphenyl]-3'-[4-(ethanesulfonyloxy)-3-methylphenyl]pentane

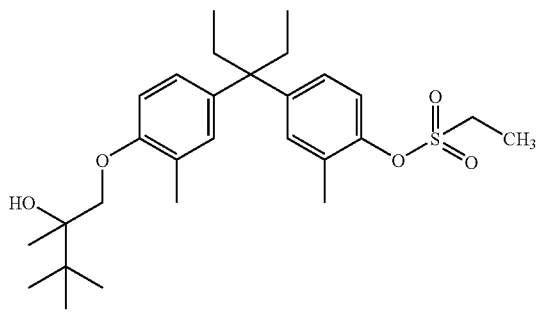

To a 0 C mixture of 3'-[4-(2-oxo-3,3-dimethylbutoxy)-3-methylphenyl]-3'-[4-(ethanesulfonyloxy)-3-methylphenyl]pentane (200 mg, 0.42 mmol) in THF (1 ml) is added 3 M MeMgBr/THF (150 ul, 0.46 mmol), warmed to RT, and stirred overnight. The reaction is diluted with Et$_2$O, washed with 1 N HCl, water, brine, Na$_2$SO$_4$ dried, and chromatographed (CHCl$_3$ to 10% EtOAc/CHCl$_3$) to give the title compound (150 mg, 75%).

ES-MS: 489.1 (M−1).

Example 11

Preparation of 3'-[4-(2-oxo-3,3-dimethylbutoxy)-3-methylphenyl]-3'-[4-(methanesulfonyloxy)-3-methylphenyl]pentane

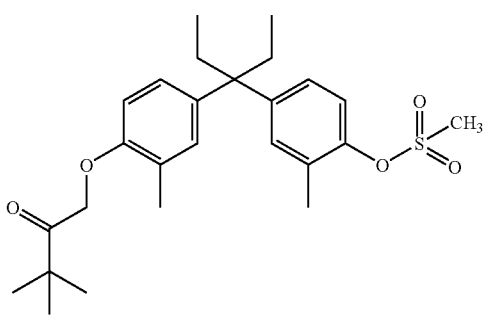

Using a procedure analogous to Example 1D, 3'-[4-(2-oxo-3,3-dimethylbutoxy)-3-methylphenyl]-3'-[4-(hydroxy)-3-methylphenyl]pentane gives the title compound (1.68 g, 61%).

NMR

FAB-MS: 460.4 (M+).

Example 12

Preparation of 3'-[4-(2-hydroxy-2-methyl-3,3-dimethylbutoxy)-3-methylphenyl]-3'-[4-(methanesulfonylamino)-3-methylphenyl]pentane

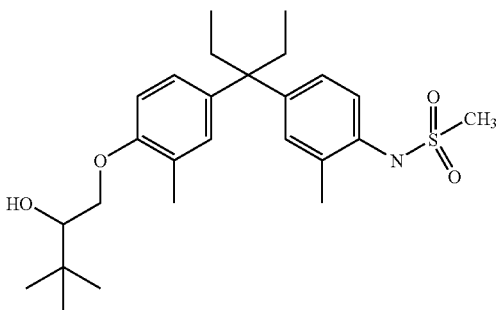

A. 3'-[4-(2-benzyloxy)-3-methylphenyl]-3'-[4-hydroxy-3-methylphenyl]pentane

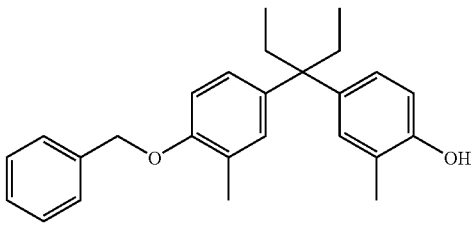

To a mixture of 3'-[4-(2-hydroxy)-3-methylphenyl]-3'-[4-hydroxy-3-methylphenyl]pentane (70 g, 246 mmol)/DMF (800 ml) is added 60% disp NaH (9.9 g, 246 mmol). After stirring for 90 m, benzyl bromide (4.2 ml, 35.2 mmol) is added dropwise. The reaction is stirred for 18 h and concentrated (vacuum at 50 C). The residue is added Et$_2$O/1 N HCl and partitioned. The organic layer is washed with water (2×), Na$_2$SO$_4$ dried, and concentrated. The residue is chromatographed (Hex to 20% EtOAc/Hex) to give the title compound (44 g, 48%, Rf=0.15; 10% EtAOc/Hex).

B. 3'-[4-(2-benzyloxy)-3-methylphenyl]-3'-[4-trifluoromethylsulfonyloxy-3-methylphenyl]pentane

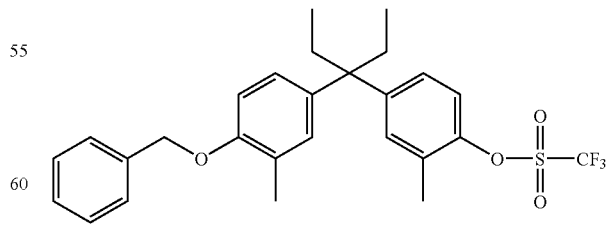

Using a procedure analogous to Example 5, 3'-[4-(2-benzyloxy)-3-methylphenyl]-3'-[4-hydroxy-3-methylphenyl]pentane gives the title compound (27 g, 95%).

NMR

C. 3'-[4-(Benzyloxy)-3-methylphenyl]-3'-[4-(methoxycarbonyl)-3-methylphenyl]pentane

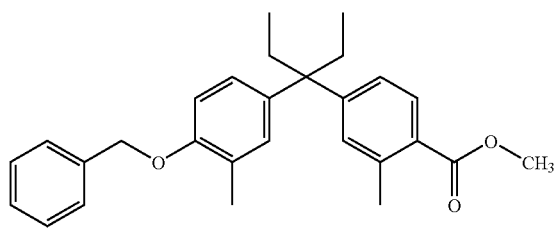

A mixture of 3'-[4-(2-benzyloxy)-3-methylphenyl]-3'-[4-trifluoromethylsulfonyloxy-3-methylphenyl]pentane (35.5 g, 70 mmol), Pd(OAc)$_2$ (1.6 g, 7.0 mmol), DPPF (7.8 g, 14.0 mmol), MeOH (30 ml, 700 mmol), Et$_3$N (30 ml, 210 mmol), and DMF (133 ml) is pressurized with carbon monoxide (1000 psi) and heated to 110° C. for 48 h. After cooling, the reaction is filtered through diatomaceous earth with EtOAc wash. The filtrate is diluted with Et$_2$O, washed with 1N HCl, and filtered through diatomaceous earth. The filtrate is washed with water, Na$_2$SO$_4$ dried, concentrated, and chromatographed (Hex to 10% EtOAc/Hex) to give the title compound (26 g, 89%).

D. 3'-[4-(Benzyloxy)-3-methylphenyl]-3'-[4-carboxyl-3-methylphenyl]pentane

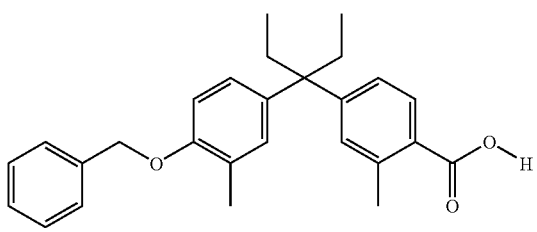

A mixture of 3'-[4-benzyloxy-3-methylphenyl]-3'-[4-methoxycarbonyl-3-methylphenyl]pentane (26 g, 62 mmol), EtOH (200 ml), water (100 ml) is added KOH (17 g, 300 mmol) and heated to 65° C. for 24 h. The reaction is concentrated and the residue was partitioned between Et$_2$O and 1N HCl. The organic layer is washed with water, Na$_2$SO$_4$ dried, concentrated, and chromatographed (CHCl$_3$ to 5% MeOH/CHCl$_3$) to give the title compound (23 g, 92%).

NMR

High Res. ES-MS (negative ion): 401.2099; calc. for C$_{27}$H$_{30}$O$_3$—H, 401.2117.

E. 3'-[4-(Benzyloxy)-3-methylphenyl]-3'-[4-(t-butoxycarbonylamino)-3-methylphenyl]pentane

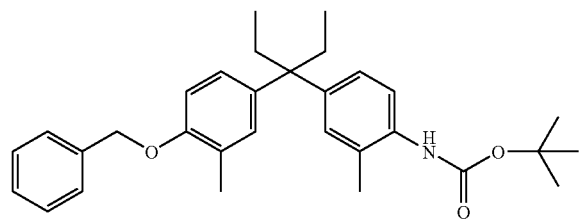

To a 0 C mixture of 3'-[4-(benzyloxy)-3-methylphenyl]-3'-[4-(carboxy)-3-methylphenyl]pentane (3.2 g, 7.9 mmol), Et3N (1.2 ml, 8.3 mmol), and CH$_2$Cl$_2$ (15 ml) is added (PhO)$_2$PO(N$_3$) (1.8 ml, 8.2 mmol) and stirred for 1 h. The reaction is concentrated to a small volume. This concentrate is added to a 90 C solution of t-BuOH and heated with an open stream of nitrogen for 1.75 h. The reaction is cooled to RT, dissolved in a minimal of 1:1 CH$_2$Cl$_2$:10% EtOAc/Hex, and chromatographed (10% EtOAc/Hex) to give the title compound as a white glassy solid (2.6 g, 69%).

F. 3'-[4-(Hydroxy)-3-methylphenyl]-3'-[4-(t-butoxycarbonylamino)-3-methylphenyl]pentane

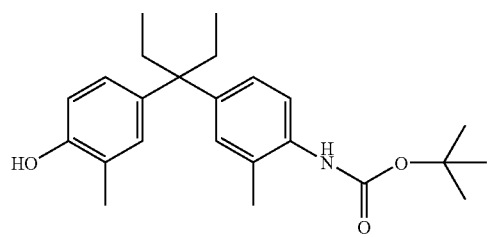

A mixture of 3'-[4-(benzyloxy)-3-methylphenyl]-3'-[4-(t-butoxycarbonylamino)-3-methylphenyl]pentane (2.45 g, 5.2 mmol), 10% Pd—C (250 mg), and EtOH (15 ml) is hydrogenated at 1 atmosphere pressure for 48 h. the reaction is filtered through diatomaceous earth with CH$_2$Cl$_2$ washes. The filtrate is concentrated and chromatograpghed (CH$_2$Cl$_2$ to 5% EtOAc/CH$_2$Cl$_2$) to give the title compound as a white glassy solid (2.0 g, quant).

NMR

ES-MS: 384.2 (M+H).

G. 3'-[4-(2-Oxo-3,3-dimethylbutoxy)-3-methylphenyl]-3'-[4-(t-butoxycarbonylamino)-3-methylphenyl]pentane

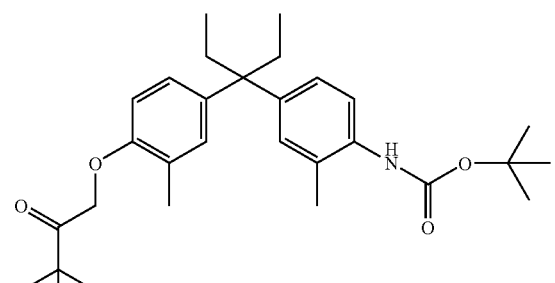

Using a procedure analogous to Example 1B, 3'-[4-(hydroxy)-3-methylphenyl]-3'-[4-(t-butoxycarbonylamino)-3-methylphenyl]pentane gives the compound as a white glassy solid (2.3 g, 96%).

H. 3'-[4-(2-Hydroxy-3,3-dimethylbutoxy)-3-methylphenyl]-3'-[4-(t-butoxycarbonylamino)-3-methylphenyl]pentane

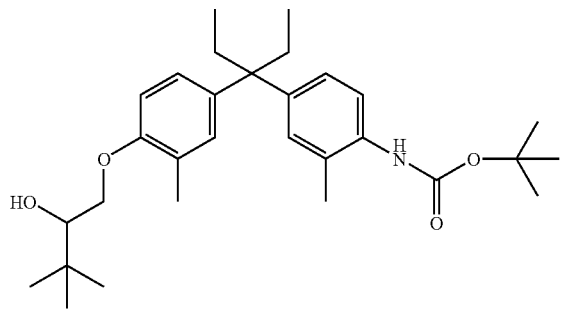

Using a procedure analogous to Example 1C, 3'-[4-(2-oxo-3,3-dimethylbutoxy)-3-methylphenyl]-3'-[4-(t-butoxycarbonylamino)-3-methylphenyl]pentane gives the title compound as a white glassy solid (2.1 g, quant).

NMR

High Res. ES-MS: 501.3693; calc. for $C_{30}H_{45}NO_4$+ ($NH_4$): 501.3692.

I. 3'-[4-(2-Hydroxy-3,3-dimethylbutoxy)-3-methylphenyl]-3'-[4-amino-3-methylphenyl]pentane

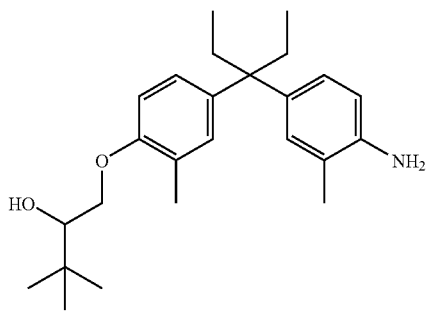

To a mixture of 3'-[4-(2-hydroxy-3,3-dimethylbutoxy)-3-methylphenyl]-3'-[4-(t-butoxycarbonylamino)-3-methylphenyl]pentane (2.2 g, 4.5 mmol), anisole (9.9 ml, 90.9 mmol), and $CH_2Cl_2$ (5 ml) is added TFA (7.0 ml, 90.9 mmol). The reaction is stirred for 2 h, concentrated, and partitioned between EtOAc/satd $Na_2CO_3$. The organic layer is washed with water, $Na_2SO_4$ dried, concentrated, and chromatographed (50% $CHCl_3$/Hex to $CHCl_3$) to give the title compound (250 mg, 92%).

NMR

High Res. ES-MS: 384.2915; calc. for $C_{25}H_{38}NO_2$: 384.2903.

J. 3'-[4-(2-Hydroxy-3,3-dimethylbutoxy)-3-methylphenyl]-3'-[4-(methanesulfonylamino)-3-methylphenyl]pentane Using a procedure analogous to Example 5, 3'-[4-(2-hydroxy-3,3-dimethylbutoxy)-3-methylphenyl]-3'-[4-(amino)-3-methylphenyl]pentane gives the title compound as a glassy white solid (240 mg, 80%).

NMR

High Res. FAB-MS: 461.2613; calc. for $C_{26}H_{39}NO_4S$: 461.2600.

Example 13 & 14

Preparation of enantiomers of 3'-[4-(2-Hydroxy-3,3-dimethylbutoxy)-3-methylphenyl]-3'-[4-(methanesulfonylamino)-3-methylphenyl]pentane

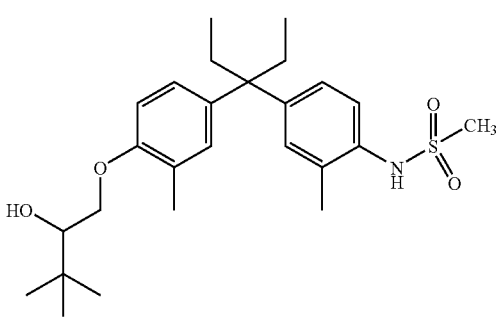

A racemic mixture of 3'-[4-(2-hydroxy-3,3-dimethylbutoxy)-3-methylphenyl]-3'-[4-(methanesulfonylamino)-3-methylphenyl]pentane is chromatographed (Chiralpak AD) to give enantiomer 1 (Example 13) of the title compound (82 mg, 41%) and enantiomer 2 (Example 14) of the title compound (73 mg, 37%).

Enantiomer 1
rt: 5.43 m (40% IPA/Hept); 225 nm.
NMR equivalent to Example 12.
High Res. ES-MS: 479.2966; calc. for $C_{26}H_{39}NO_4S$+ ($NH_4$): 479.2944

Enantiomer 2
rt: 7.14 m (40% IPA/Hept); 225 nm.
NMR equivalent to Example 12.
High Res. ES-MS: 479.2932; calc. for $C_{26}H_{39}NO_4S$+ ($NH_4$): 479.2944

Example 15 & 16

Preparation of enantiomers of 3'-[4-(2-hydroxy-3,3-dimethylbutoxy)-3-methylphenyl]-3'-[4-(ethanesulfonyloxy)-3-methylphenyl]pentane

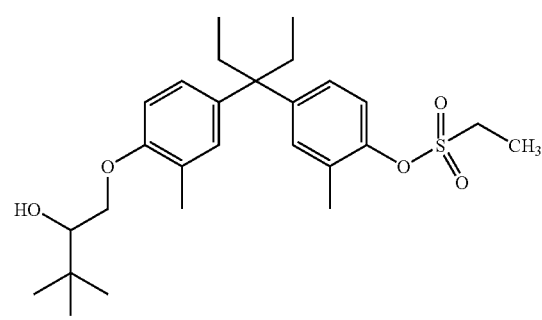

A racemic mixture of 3'-[4-(2-hydroxy-3,3-dimethylbutoxy)-3-methylphenyl]-3'-[4-(ethanesulfonyloxy)-3-methylphenyl]pentane is chromatographed on (Chiralpak AD) to give enantiomer 1 (Example 15) of the title compound (209 mg, quant) and enantiomer 2 (Example 16) of the title compound (199 mg, quant).

Enantiomer 1, Example 15
rt: 7.8 m (20% IPA/Hept); 220 nm.
NMR equivalent to Example 9.
High Res. ES-MS: 494.2943; calc. for $C_{27}H_{40}O_5S+(NH_4)$: 494.2940

Enantiomer 2, Example 16
rt: 11.0 m (20% IPA/Hept); 220 nm.
NMR equivalent to Example 9.
High Res. ES-MS: 494.2960; calc. for $C_{27}H_4OO_5S+(NH_4)$: 494.2940

Example 17

Preparation of N-(4-{1-[4-(3,3-Dimethyl-2-oxo-butoxy)-3-methyl-phenyl]-1-ethyl-propyl}-2-methyl-phenyl)-methanesulfonamide

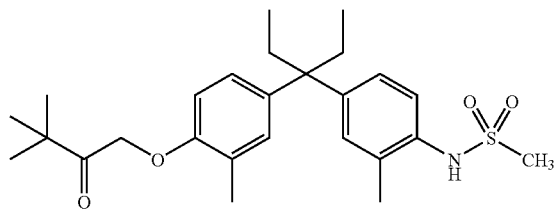

To a 0° C. mixture of 1-{4-[1-(4-amino-3-methyl-phenyl)-1-ethyl-propyl]-2-methyl-phenoxy}-3,3-dimethyl-butan-2-one (763 mg, 2 mmol), triethylamine (0.42 mL, 3 mmol) and $CH_2Cl_2$ (7 mL) is added methanesulfonyl chloride (0.155 mL, 2 mmol). The reaction is warmed to RT and stirred for 3 h. The reaction is diluted with $CH_2Cl_2$ dichloromethane and washed with 0.2 N HCl. The organic phase is Na2SO4 dried, concentrated, and chromatogrpahed (0% to 25% EtOAc/Hex) to give the title compound (800 mg, 87%).

$^1$H NMR (CDCl$_3$) δ 7.29 (d, 1H, J=8.3 Hz), 7.03 (d, 1H, J=8.3 Hz), 6.99 (s, 1H), 6.89 (s, 1H), 6.88 (d, 1H, J=8.3 Hz), 6.49 (d, 1H, J=8.3 Hz), 6.02 (s, 1H), 4.84 (s, 2H), 3.01 (s, 3H), 2.26 (s, 3H), 2.24 (s, 3H), 2.03 (q, 4H), 1.25 (s, 9H), 0.58 (t, 6H).

HRMS: calcd. for C26H41N2O4S (M+18), 477.2787, found, 477.2801.

Example 18

Preparation of N-(4-{1-[4-(3,3-Dimethyl-2-oxo-butoxy)-3-methyl-phenyl]-1-ethyl-propyl}-2-methyl-phenyl)-N-methyl-methanesulfonamide

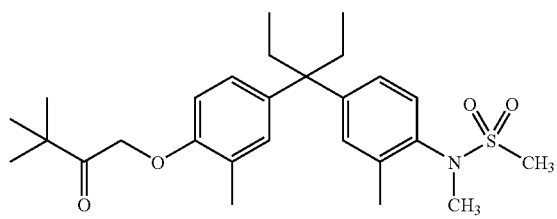

To a mixture of N-(4-{1-[4-(3,3-dimethyl-2-oxo-butoxy)-3-methyl-phenyl]-1-ethyl-propyl}-2-methyl-phenyl)-methanesulfonamide (230 mg, 0.5 mmol), triphenyl phosphine (197 mg, 0.75 mmol), MeOH (0.03 mL, 0.75 mmol), and THF (10 mL) is added diethylazodicarboxylate (0.12 mL, 0.75 mmol) and stirred overnight. The reaction is concentrated and chromatographed (0% to 25% EtOAc/Hex) to give the title compound (180 mg, 76%).

$^1$H NMR (CDCl$_3$) δ 7.09 (s, 1H), 7.07 (d, 1H, J=8.4 Hz), 6.97 (dd, 1H, J=2.2, 8.4 Hz), 6.92 (s, 1H), 6.88 (dd, 1H, J=2.2, 8.4 Hz), 6.49 (d, 1H, J=8.4 Hz), 4.85 (s, 2H), 3.21 (s, 3H), 2.95 (s, 3H), 2.35 (s, 3H), 2.25 (s, 3H), 2.03 (q, 4H), 1.25 (s, 9H), 0.58 (t, 6H).

HRMS: calcd. for C27H43N2O4S (M+18), 491.2944, found, 491.2939.

Example 19

Preparation of N-(4-{1-Ethyl-1-[4-(2-hydroxy-3,3-dimethyl-butoxy)-3-methyl-phenyl]-propyl}-2-methyl-phenyl)-N-methyl-methanesulfonamide

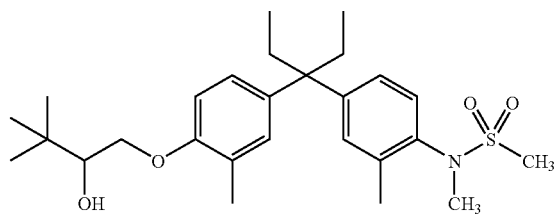

To a 0° C. mixture of N-(4-{1-[4-(3,3-dimethyl-2-oxo-butoxy)-3-methyl-phenyl]-1-ethyl-propyl}-2-methyl-phenyl)-N-methyl-methanesulfonamide (100 mg, 0.21 mmol), MeOH (5 mL), and THF (10 mL) is added NaBH$_4$ (12 mg, 0.32 mmol). The reaction is warmed to RT and stirred for 5 h and concentrated. The residue is partitioned between EtOAc and 0.2 N HCl. The organic phase is Na$_2$SO$_4$ dried, concentrated, and chromatographed (0% to 25% EtOAc/Hex) to give the title compound (60 mg, 60%).

$^1$H NMR (CDCl$_3$) δ 7.09 (s, 1H), 7.08 (d, 1H, J=8.3 Hz), 6.97 (dd, 1H, J=2.0, 8.3 Hz), 6.93 (dd, 1H, J=2.0, 8.3 Hz), 6.92 (s, 1H), 6.71 (d, 1H, J=8.3 Hz), 4.10 (dd, 1H, J=2.7, 8.7 Hz), 3.87 (dd, 1H, J=8.7, 8.8 Hz), 3.72 (dd, 1H, J=2.4, 8.8 Hz), 3.22 (s, 3H), 2.96 (s, 3H), 2.36 (s, 3H), 2.20 (s, 3H), 2.05 (q, 4H), 1.03 (s, 9H), 0.62 (t, 6H).

HRMS: calcd. for C27H41NO4NaS (M+23), 498.2654, found, 498.2657.

Example 20 and Example 21

Preparation of enantiomers of N-(4-{1-ethyl-1-[4-(2-hydroxy-3,3-dimethyl-butoxy)-3-methyl-phenyl]-propyl}-2-methyl-phenyl)-N-methyl-methanesulfonamide

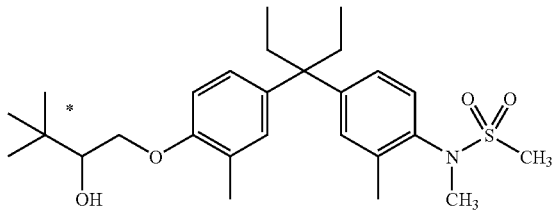

A racemic mixture of N-(4-{1-ethyl-1-[4-(2-hydroxy-3,3-dimethyl-butoxy)-3-methyl-phenyl]-propyl}-2-methyl-phenyl)-N-methyl-methanesulfonamide (48 mg) is chromatographed (Chiralpak AD column) to give enantiomer 1, Example 20 (13 mg, 27%) and enantiomer 2, Example 21 (12 mg, 25%).

HPLC: Chiralpak AD (4.6×150 mm); 60% heptane, 40% 2-propanol; flow rate: 1.0 ml/m; UV: 225 nm Enantiomer 1, Example 20: rt=4.98 m;
$^1$H NMR (CDCl$_3$): equivalent to Example 19

Enantiomer 2, Example 21: rt=5.97 m.
$^1$H NMR (CDCl$_3$): equivalent to Example 19

Example 22 and Example 23

Preparation of N-(4-{1'-[4-(3,3-Dimethyl-2-oxo-butoxy)-3-methyl-phenyl]-1-ethyl-propyl}-2-methyl-phenyl)-N,N-bis-ethanesulfonamide

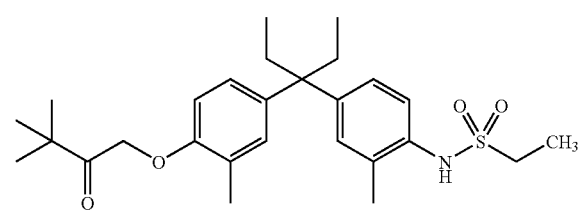

and N-(4-{1-[4-(3,3-Dimethyl-2-oxo-butoxy)-3-methyl-phenyl]-1-ethyl-propyl}-2-methyl-phenyl)-ethanesulfonamide Using a procedure analogous to Example 17, 1-{4-[1-(4-amino-3-methyl-phenyl)-1-ethyl-propyl]-2-methyl-phenoxy}-3,3-dimethyl-butan-2-one (229 mg, 0.6 mmol), ethanesulfonyl chloride (0.080 mL, 0.9 mmol) gives N-(4-{1-[4-(3,3-dimethyl-2-oxo-butoxy)-3-methyl-phenyl]-1-ethyl-propyl}-2-methyl-phenyl)-N,N-bis-ethanesulfonamide (Example 22) (120 mg, 35%), and N-(4-{1-[4-(3,3-Dimethyl-2-oxo-butoxy)-3-methyl-phenyl]-1-ethyl-propyl}-2-methyl-phenyl)-ethanesulfonamide (Example 23) (130 mg, 46%).

for Example 22
$^1$H NMR (CDCl$_3$) δ 7.15 (d, 1H, J=8.3 Hz), 7.10 (s, 1H), 7.01 (d, 1H, J=8.8 Hz), 6.94 (s, 1H), 6.86 (d, 1H, J=8.8 Hz), 6.49 (d, 1H, J=8.3 Hz), 4.85 (s, 2H), 3.55, 3.72 (m, 4H), 2.40 (s, 3H), 2.27 (s, 3H), 2.04 (q, 4H), 1.54 (m, 6H), 1.27 (s, 9H), 0.59 (t, 6H);

LC-MS: 583 (M+18).

for Example 23
$^1$H NMR (CDCl$_3$) δ 7.28 (d, 1H, J=8.3 Hz), 7.01 (dd, 1H, J=2.0, 8.3 Hz), 6.97 (s, 1H), 6.89 (s, 1H), 6.86 (d, 1H, J=8.3 Hz), 6.49 (d, 1H, J=8.3 Hz), 5.97 (s, 1H), 4.85 (s, 2H), 3.16 (q, 2H), 2.27 (s, 3H), 2.25 (s, 3H), 2.04 (q, 4H), 1.41 (t, 3H), 1.27 (s, 9H), 0.59 (t, 6H).

LC-MS: 491 (M+18).

Example 24

Preparation of N-(4-{1-[4-(3,3-Dimethyl-2-oxo-butoxy)-3-methyl-phenyl]-1-ethyl-propyl}-2-methyl-phenyl)-N-methyl-ethanesulfonamide

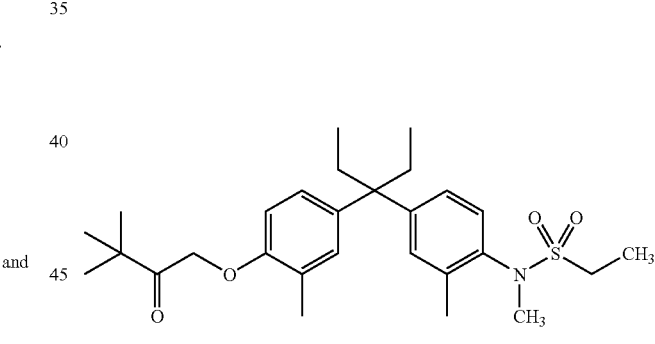

The title compound is prepared from N-(4-{1-[4-(3,3-dimethyl-2-oxo-butoxy)-3-methyl-phenyl]-1-ethyl-propyl}-2-methyl-phenyl)-ethanesulfonamide and methanol using a procedure analogous to Example 18 (78%).

$^1$H NMR (CDCl$_3$) δ 7.09 (d, 1H, J=8.4 Hz), 7.08 (s, 1H), 6.96 (dd, 1H, J=2.0, 8.4 Hz), 6.92 (d, 1H, J=2.2 Hz), 6.88 (dd, 1H, J=2.2, 8.4 Hz), 6.49 (d, 1H, J=8.4 Hz), 4.85 (s, 2H), 3.22 (s, 3H), 3.12 (q, 2H), 2.35 (s, 3H), 2.25 (s, 3H), 2.03 (q, 4H), 1.43 (t, 3H), 1.25 (s, 9H), 0.60 (t, 6H).

HRMS: calcd. for C28H41NO4NaS (M+23), 510.2654, found, 510.2666.

Example 25 and Example 26

N-(4-{1-[4-(3,3-Dimethyl-2-oxo-butoxy)-3-methyl-phenyl]-1-ethyl-propyl}-2-methyl-phenyl)-N,N-bis-1-propanesulfonamide

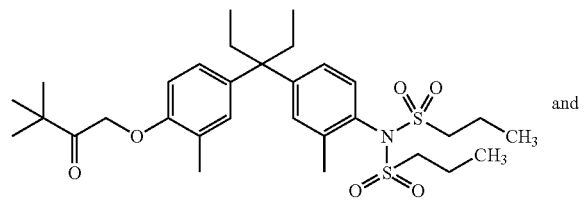
and

N-(4-{1-[4-(3,3-Dimethyl-2-oxo-butoxy)-3-methyl-phenyl]-1-ethyl-propyl}-2-methyl-phenyl)-1-propanesulfonamide

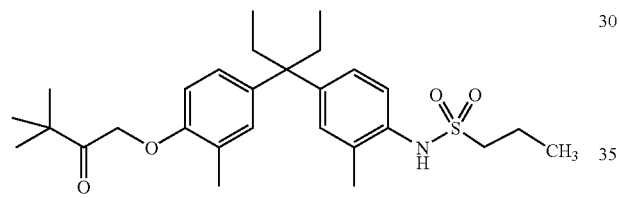

Using a procedure analogous to Example 22 and Example 23, 1-{4-[1-(4-amino-3-methyl-phenyl)-1-ethyl-propyl]-2-methyl-phenoxy}-3,3-dimethyl-butan-2-one and 1-propanesulfonyl chloride give the title compounds Example 25 (34%) and Example 26 (42%).

for Example 25:
$^1$H NMR (CDCl$_3$) δ 7.13 (d, 1H, J=8.3 Hz), 7.10 (s, 1H), 7.01 (d, 1H, J=8.3 Hz), 6.94 (s, 1H), 6.87 (d, 1H, J=8.8 Hz), 6.49 (d, 1H, J=8.8 Hz), 4.85 (s, 2H), 3.63 (m, 2H), 3.50 (m, 2H), 2.39 (s, 3H), 2.25 (s, 3H), 1.92, 2.06 (m, 8H), 1.26 (s, 9H), 1.09 (t, 6H), 0.59 (t, 6H);
HRMS: Calcd. for C$_{31}$H$_{47}$NO$_6$NaS$_2$ (M+23), 616.2743, found, 616.2769;

for Example 26:
$^1$H NMR (CDCl$_3$) δ 7.28 (d, 1H, J=8.8 Hz), 7.00 (dd, 1H, J=2.4, 8.3 Hz), 6.97 (s, 1H), 6.89 (s, 1H), 6.87 (d, 1H, J=8.8 Hz), 6.49 (d, 1H, J=8.3 Hz), 6.00 (s, 1H), 4.84 (s, 2H), 3.09 (q, 2H), 2.25 (s, 3H), 2.23 (s, 3H), 2.02 (q, 4H), 1.87 (q, 2H), 1.25 (s, 9H), 1.04 (t, 3H), 0.58 (t, 6H);
HRMS: Calcd. for C$_{28}$H$_{41}$NO$_4$NaS (M+23), 510.2654, found, 510.2664.

Example 27

N-(4-{1-[4-(3,3-Dimethyl-2-oxo-butoxy)-3-methyl-phenyl]-1-ethyl-propyl}-2-methyl-phenyl)-trifluoromethanesulfonamide

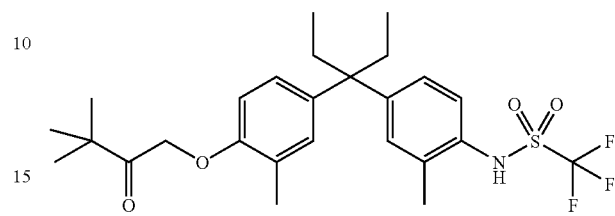

The title compound is prepared from 1-{4-[1-(4-amino-3-methyl-phenyl)-1-ethyl-propyl]-2-methyl-phenoxy}-3,3-dimethyl-butan-2-one and trifluoromethane sulfonyl chloride using a procedure analogoues to Example 17 (45%).
$^1$H NMR (CDCl$_3$) δ 6.94 (s, 1H), 6.92 (d, 1H, J=8.3 Hz), 6.83 (s, 1H), 6.81 (d, 1H, J=8.8 Hz), 6.58 (d, 1H, J=8.8 Hz), 6.49 (d, 1H, J=8.3 Hz), 4.84 (s, 2H), 2.25 (s, 3H), 2.13 (s, 3H), 2.01 (q, 4H), 1.27 (s, 9H), 0.59 (t, 6H).

Example 28 and Example 29

Preparation of N-(4-{1-[4-(3,3-Dimethyl-2-oxo-butoxy)-3-methyl-phenyl]-1-ethyl-propyl}-2-methyl-phenyl)-N,N-bis-2,2,2-trifluoro-ethanesulfonamide

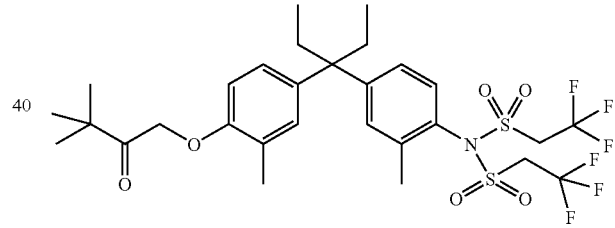

N-(4-{1-[4-(3,3-Dimethyl-2-oxo-butoxy)-3-methyl-phenyl]-1-ethyl-propyl}-2-methyl-phenyl)-2,2,2-trifluoro-ethanesulfonamide

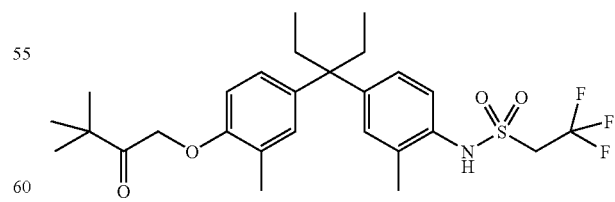

Using a procedure analogous to Example 22 and Example 23, 1-(4-[1-(4-amino-3-methyl-phenyl)-1-ethyl-propyl]-2-methyl-phenoxy)-3,3-dimethyl-butan-2-one and 1-propanesulfonyl chloride give the title compounds Example 28 (49%) and Example 29 (25%).

for Example 28:

$^1$H NMR (CDCl$_3$) δ 7.16 (s, 1H), 7.08 (s, 2H), 6.93 (s, 1H), 6.86 (d, 1H, J=8.3 Hz), 6.49 (d, 1H, J=8.8 Hz), 4.86 (s, 2H), 4.49 (m, 2H), 4.34 (m, 2H), 2.38 (s, 3H), 2.27 (s, 3H), 2.05 (q, 4H), 1.27 (s, 9H), 0.61 (t, 6H);

HRMS: Calcd. for C29H41N2O6F6S2 (M+18), 691.2310, found, 691.2337;

for Example 29:

$^1$H NMR (CDCl$_3$) δ 7.26 (d, 1H, J=8.8 Hz), 7.03 (m, 2H), 6.89 (s, 1H), 6.87 (d, 1H, J=8.3 Hz), 6.49 (d, 1H, J=8.8 Hz), 6.02 (s, 1H), 4.85 (s, 2H), 3.87 (m, 2H), 2.28 (s, 3H), 2.24 (s, 3H), 2.03 (q, 4H), 1.25 (s, 9H), 0.59 (t, 6H).

HRMS: calcd. for C27H40N2O4F3S (M+18), 545.2661, found, 545.2685.

Example 30

N-(4-{1-[4-(3,3-Dimethyl-2-oxo-butoxy)-3-methyl-phenyl]-1-ethyl-propyl}-2-methyl-phenyl)-N-(2-methylsulfanyl-ethyl)-methanesulfonamide

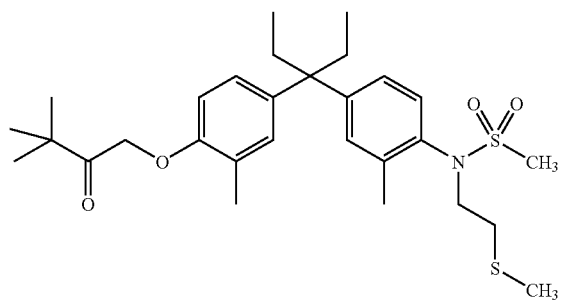

The title compound is prepared from N-(4-{(1-[4-(3,3-dimethyl-2-oxo-butoxy)-3-methyl-phenyl]-1-ethyl-propyl}-2-methyl-phenyl)-methanesulfonamide and 2-methylsulfanyl-ethanol using a procedure analogous to Example 18 (58%).

$^1$H NMR (CDCl$_3$) δ 7.10 (d, 1H, J=2.0 Hz), 7.08 (d, 1H, J=8.4 Hz), 6.97 (dd, 1H, J=2.0, 8.4 Hz), 6.92 (d, 1H, J=2.0 Hz), 6.88 (dd, 1H, J=2.4, 8.8 Hz), 6.49 (d, 1H, J=8.8 Hz), 4.85 (s, 2H), 3.75 (m, 2H), 2.99 (s, 3H), 2.35 (s, 3H), 2.25 (s, 3H), 2.10 (m, 2H), 2.02 (q, 4H), 1.73 (s, 3H), 1.25 (s, 9H), 0.59 (t, 6H).

HRMS: calcd. for C29H47N2O4S2 (M+18), 551.2977, found, 551.2984.

Example 31

N-(4-{1-[4-(3,3-Dimethyl-2-oxo-butoxy)-3-methyl-phenyl]-1-ethyl-propyl}-2-methyl-phenyl)-2-ethyl-sulfanyl-ethanesulfonamide

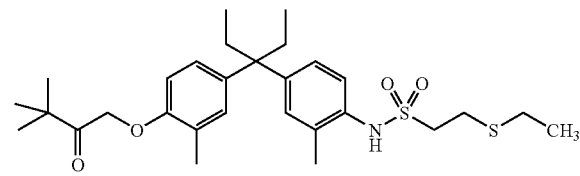

A. N-(4-{1-[4-(3,3-dimethyl-2-oxo-butoxy)-3-methyl-phenyl]-1-ethyl-propyl}-2-methyl-phenyl)-2-chloro-ethanesulfonamide

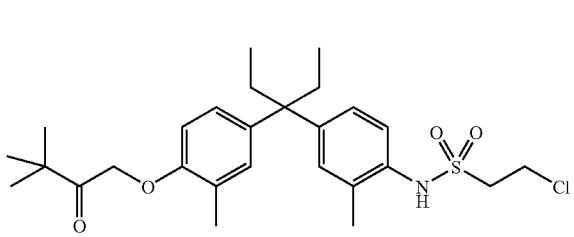

Using a procedure analogous to Example 17, 1-{4-[1-(4-amino-3-methyl-phenyl)-1-ethyl-propyl]-2-methyl-phenoxy}-3,3-dimethyl-butan-2-one (382 mg, 1 mmol), 2-chloro-ethanesulfonyl chloride (0.1 mL, 1 mmol) and triethylamine (0.14 mL, 1 mmol) give the title compound as a oil (500 mg, quant.)

ESMS$^-$: 470 (M−HCl);

B. N-(4-{1-[4-(3,3-Dimethyl-2-oxo-butoxy)-3-methyl-phenyl]-1-ethyl-propyl}-2-methyl-phenyl)-2-ethylsulfanyl-ethanesulfonamide A 0° C. solution of ethanethiol (0.1 mL, 1.35 mmol) in THF (5 mL) is treated with NaH (81 mg, 2 mmol, 60% in mineral oil) and stirred for 10 m. The mixture is added a solution of N-(4-{1-[4-(3,3-dimethyl-2-oxo-butoxy)-3-methyl-phenyl]-1-ethyl-propyl}-2-methyl-phenyl)-2-chloro-ethanesulfonamide (500 mg, 1 mmol) in THF (10 mL), warmed to RT, and stirred overnight. The reaction is concentrated, dissolved in CH$_2$Cl$_2$, and washed with 0.2 N HCl. The organic layer is concentrated and chromatographed (0%-20% EtOA/Hex) to give the title compound (270 mg, 51%).

$^1$H NMR (CDCl$_3$) δ 7.28 (d, 1H, J=8.3 Hz), 7.02 (d, 1H, J=8.3 Hz), 6.98 (s, 1H), 6.87, 6.89 (m, 2H), 6.49 (d, 1H, J=8.8 Hz), 6.27 (s, 1H), 4.85 (s, 2H), 3.36 (m, 2H), 3.30 (m, 2H), 2.51 (q, 2H), 2.28 (s, 3H), 2.25 (s, 3H), 2.03 (q, 4H), 1.27 (s, 9H), 1.22 (t, 3H), 0.60 (t, 6H);

HRMS: Calcd. for C29H44NO4S2 (M+1), 534.2712, found, 534.2736.

Example 32

N-(4-{1-[4-(3,3-Dimethyl-2-oxo-butoxy)-3-methyl-phenyl]-1-ethyl-propyl}-2-methyl-phenyl)-2-ethane-sulfonyl-ethanesulfonamide

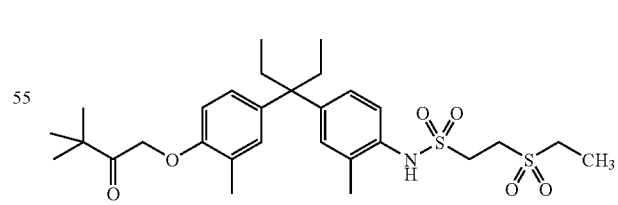

To a solution of N-(4-{1-[4-(3,3-dimethyl-2-oxo-butoxy)-3-methyl-phenyl]-1-ethyl-propyl}-2-methyl-phenyl)-2-ethylsulfanyl-ethanesulfonamide (220 mg, 0.41 mmol) in dichloromethane (10 mL) is added m-chloroperbenzoic acid (427 mg, 1.24 mmol, 50%) at RT. After stirring for 3 h, the reaction is concentrated and chromatographed (0%-33% EtOAc/Hex) to give the title compound (190 mg, 81%).

¹H NMR (CDCl₃) δ 7.27 (d, 1H, J=8.3 Hz), 7.03 (d, 1H, J=8.3 Hz), 7.02 (s, 1H), 6.86, 6.90 (m, 2H), 6.50 (d, 1H, J=8.3 Hz), 6.19 (s, 1H), 4.85 (s, 2H), 3.60 (m, 2H), 3.44 (m, 2H), 3.08 (q, 2H), 2.30 (s, 3H), 2.25 (s, 3H), 2.03 (q, 4H), 1.45 (t, 3H), 1.27 (s, 9H), 0.60 (t, 6H);

HRMS: Calcd. for C29H43NO6NaS2 (M+23), 588.2430, found, 588.2406.

Example 33

N-(4-{1-[4-(3,3-Dimethyl-2-oxo-butoxy)-3-methyl-phenyl]-1-ethyl-propyl}-2-methyl-phenyl)-2-isopropylsulfanyl-ethanesulfonamide

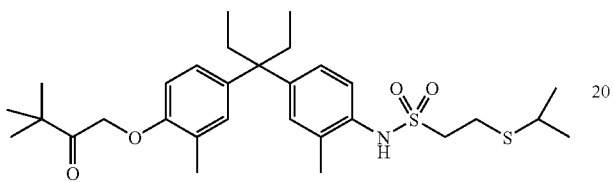

Using a procedure analogous to Example 31B, 4-{1-[4-(3,3-dimethyl-2-oxo-butoxy)-3-methyl-phenyl]-1-ethyl-propyl}-2-methyl-phenyl)-2-chloro-ethanesulfonamide (Example 31A) and propane-2-thiol give the title compound (44%).

¹H NMR (CDCl₃) δ 7.29 (d, 1H, J=8.3 Hz), 7.02 (d, 1H, J=8.8 Hz), 6.98 (s, 1H), 6.89 (s, 1H), 6.88 (d, 1H, J=8.3 Hz), 6.49 (d, 1H, J=8.8 Hz), 6.09 (s, 1H), 4.85 (s, 2H), 3.35 (t, 2H), 2.92 (m, 3H), 2.27 (s, 3H), 2.25 (s, 3H), 2.03 (q, 4H), 1.27 (s, 9H), 1.23 (d, 6H), 0.60 (t, 6H);

HRMS: Calcd. for C30H45NO4NaS2 (M+23), 570.2688, found, 570.2680.

Example 34

N-(4-{1-[4-(3,3-Dimethyl-2-oxo-butoxy)-3-methyl-phenyl]-1-ethyl-propyl}-2-methyl-phenyl)-2-(propane-2-sulfonyl)-ethanesulfonamide

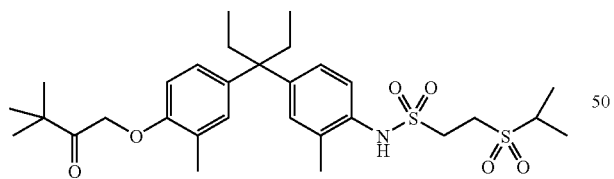

Using a procedure analogous to Example 32, 4-{1-[4-(3,3-dimethyl-2-oxo-butoxy)-3-methyl-phenyl]-1-ethyl-propyl}-2-methyl-phenyl)-2-(isopropylsulfanyl)ethanesulfonamide and m-chloroperbenzoic acid give the title compound (75%).

¹H NMR (CDCl₃) δ 7.28 (d, 1H, J=8.4 Hz), 7.03 (d, 1H, J=8.4 Hz), 7.01 (s, 1H), 6.90 (s, 1H), 6.87 (d, 1H, J=8.4 Hz), 6.50 (d, 1H, J=8.4 Hz), 6.24 (s, 1H), 4.84 (s, 2H), 3.59 (m, 2H), 3.39 (m, 2H), 3.16 (m, 1H), 2.29 (s, 3H), 2.24 (s, 3H), 2.02 (q, 4H), 1.41 (d, 6H), 1.25 (s, 9H), 0.59 (t, 6H);

HRMS: Calcd. for C30H46NO6S2 (M+1), 580.2767, found, 580.2779.

Example 35

Preparation of trifluoro-methanesulfonic acid 4-{1-ethyl-1-[4-(2-hydroxy-2,3,3-trimethyl-butoxy)-3-methyl-phenyl]-propyl}-2-methyl-phenyl ester

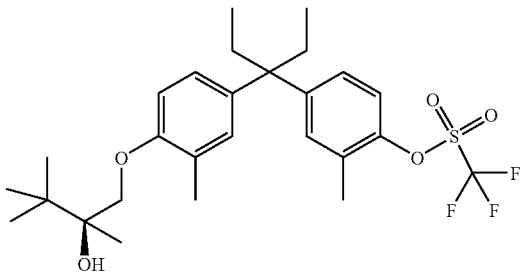

A. 1-(4-{1-[4-(tert-Butyl-dimethyl-silanyloxy)-3-methyl-phenyl]-1-ethyl-propyl}-2-methyl-phenoxy)-3,3-dimethyl-butan-2-one

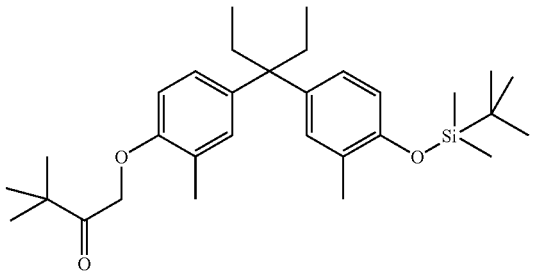

Using a procedure analogous to Example 13A, 1-{(4-[1-Ethyl-1-(4-hydroxy-3-methyl-phenyl)-propyl]-2-methyl-phenoxy}-3,3-dimethyl-butan-2-one (Example 1B) (4.91 g, 12.83 mmol) and TBSCl (1.93 g, 12.83 mmol) give the title compound (5.74 g, 11.57 mmol, 90%). ¹H NMR (CDCl₃), δ 0.21 (s, 6H), 0.60 (t, J=7.5 Hz, 6H), 1.01(s, 9H), 1.26 (s, 9H), 2.01 (q, J=7.5 Hz, 4H), 2.16 (s, 3H), 2.24 (s, 3H), 4.83 (s, 2H), 6.50 (d, J=8.4 Hz, 1H), 6.63 (d, J=8.4 Hz, 1H), 6.82 (dd, J=8.4, 2.3 Hz, 1H), 6.87-6.93 (m, 3H). LC/MS (m/z): calcd for C31H52NO3Si (M+NH4)⁺: 514.8; found: 514.5.

B. Trifluoro-methanesulfonic acid 4-{1-ethyl-1-[4-(2-hydroxy-2,3,3-trimethyl-butoxy)-3-methyl-phenyl]-propyl}-2-methyl-phenyl ester

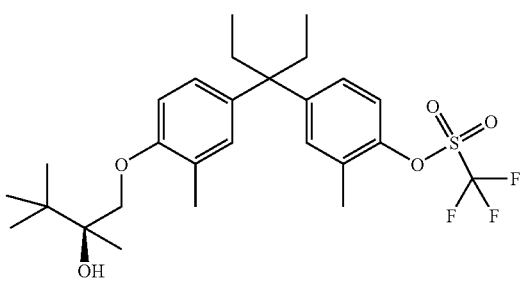

To a solution of 1-(4-{1-[4-(tert-Butyl-dimethyl-silanyloxy)-3-methyl-phenyl]-1-ethyl-propyl}-2-methyl-phenoxy)-3,3-dimethyl-butan-2-one (5.63 g, 11.40 mmol) in THF (100 mL) is treated with 3.0 M CH$_3$MgBr (5.7 mL, 17.24 mmol). The reaction is stirred for 1 h, quenched with satd NH$_4$Cl (50 mL) at 0° C., diluted with EtOAc (100 mL), washed with 0.1 M HCl (2×50 mL), MgSO$_4$ dried, and concentrated. The resulting residue is dissolved in THF (50 mL), and reacted with 1.0 M TBAF (12.6 mL, 12.6 mmol) for 1 h. The reaction is diluted with EtOAc (100 mL), washed with 0.1 M HCl (3×50 mL), brine (50 mL), MgSO$_4$ dried, and concentrated. The resulting residue is dissolved in CH$_2$Cl$_2$ (100 mL), cooled to 0° C., treated with Et$_3$N (1.7 mL, 12.38 mmol) and Tf$_2$O (1.9 mL, 11.35 mmol). After stirring 5 m, the reaction is washed with 0.1 M HCl (2×50 mL), MgSO$_4$ dried, concentrated, and chromatographed to give the title compound (5.30 g, 10.0 mmol, 87% for 3-steps). $^1$H NMR (CDCl$_3$), δ 0.61 (t, J=7.1 Hz, 6H), 1.05(s, 9H), 1.34 (s, 3H), 2.05(q, J=7.1 Hz, 4H), 2.21 (s, 3H), 2.33 (s, 3H), 3.84 (d, J=8.9 Hz, 1H), 4.01 (d, J=8.9 Hz, 1H), 6.71 (d, J=8.3 Hz, 1H), 6.87 (d, J=2.2 Hz, 1H), 6.93 (dd, J=8.8, 2.6 Hz, 1H), 7.02-7.11 (m, 3H). LC/MS (m/z): calcd for C$_{27}$H$_{41}$NF$_3$O$_5$S (M+NH$_4$)$^+$: 548.7; found: 548.2.

Example 36

Preparation of 3'-[4-(2-oxo-3,3-dimethylbutoxy)-phenyl]-3'-[4-methylsulfonyloxy-3-methylphenyl]pentane

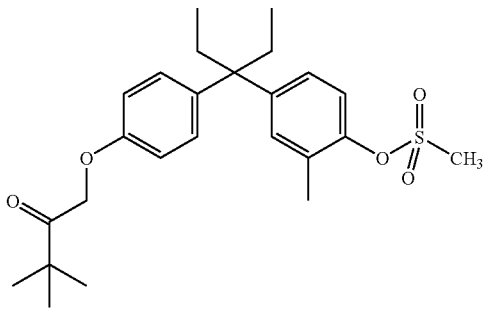

A. 3'-(4-Methoxyphenyl)-3'-(4-hydroxy-3-methylphenyl)pentane

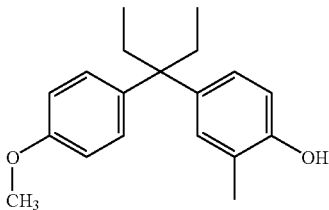

To a mixture of 3-(4-methoxyphenyl)-3-pentanol (ref. 1) (0.19 g, 1 mmol) and o-cresol (0.8 g, 7.4 mmol) is added BF3-ethereate (4 drops) and stirred for 16 h. The mixture is partitioned between diethylether and water, and the organic layer is Na$_2$SO$_4$ dried, and concentrated. The residue is vacuum dried (70-2° C./0.04 mm) for 16 h to give the title compound (0.19 g, 67%).

H-NMR (400 mHz, CDCl3): 7.06 (2H, d, J=8.8 Hz), 6.85 (2H, m), 6.77 (2H, d, 8.8 Hz), 6.64 (1H, d, J=8.0 Hz), 4.75 (1H, s), 3.77 (3H, s), 2.18 (3H, s), 2.01 (4H, q, J=7.4 Hz), 0.59 (6H, t, J=7.4 Hz).

ES/MS: 283.2 (M+1).

Ref. 1: Collins, David J.; Jacobs, Howard A. Steric and stereoelectronic effects in the hydrogenolysis and Birch reduction of some hindered tertiary-benzylic carbinols. Australian Journal of Chemistry (1987), 40(12), 1989-2004.

B. 3'-(4-Methoxyphenyl)-3'-(4-methylsulfonyloxy-3-methylphenyl)pentane

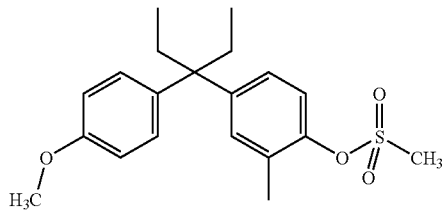

To a mixture of 3'-(4-methoxyphenyl)-3'-(4-hydroxy-3-methylphenyl)pentane (0.19 g, 0.67 mmol) and methanesulfonyl chloride (62 uL, 0.8 mmol) and of methylene chloride (10 mL) is added diisopropylethylamine (139 uL, 0.8 mmol). After stirring for 16 h, the reaction is quenched with saturated sodium bicarbonate. The organic layer is Na$_2$SO$_4$ dried, concentrated to give the title compound (0.19 g, 78%).

H-NMR (400 mHz, CDCl3): 7.12 (1H, d, J=8.4 Hz), 7.03 (4H, m), 6.78 (2H, d, J=8.8 Hz), 3.78 (3H, s), 3.16 (3H, s), 2.29 (3H, s), 2.03 (4H, q, J=7.2 Hz), 0.59 (6H, t, J=7.2 Hz).

ES/MS: 380.3 (M+NH4)

C. 3'-(4-Hydroxyphenyl)-3'-(4-methylsulfonyloxy-3-methylphenyl)pentane

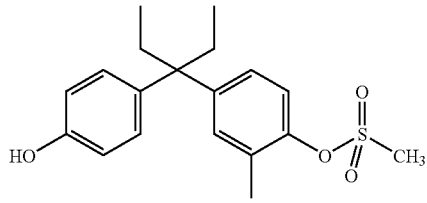

To a mixture of 3'-(4-methoxyphenyl)-3'-(4-methylsulfonyloxy-3-methylphenyl)pentane (0.19 g, 0.5 mmol) and methylene chloride (2 ml) is added 1.0 M boron tribromide (1.0 ml, 1.0 mmol). After stirring for 1 h, the mixture is quenched with satd NaHCO$_3$. The organic phase is Na$_2$SO$_4$ dried and concentrated to give the title compound (0.17 g, 99%).

H-NMR (400 mHz, CDCl3): 7.06 (1H, d, J=8.6 Hz), 7.01 (4H, m), 6.72 (2H, d, 8.4 Hz), 4.71 (1H, s), 3.15 (3H, s), 2.29 (3H, s), 2.02 (4H, q, J=7.4 Hz), 0.59 (6H, t, J=7.4 Hz).

ES/MS: 366.3 (M+NH4)

D. 3'-[4-(2-Oxo-3,3-dimethylbutoxy)-phenyl]-3'-[4-methylsulfonyloxy-3-methylphenyl]pentane

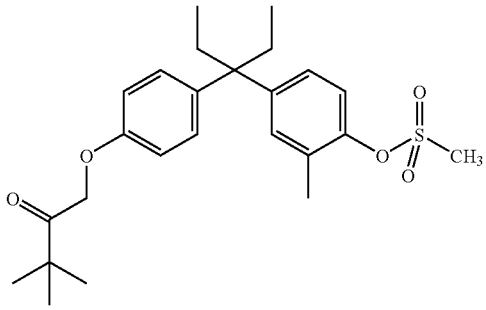

To a mixture of Hex washed NaH (15 mg 60% in mineral oil, 0.6 mmol) and DMF (2 mL) is added 3'-(4-hydroxyphenyl)-3'-(4-methylsulfonyloxy-3-methylphenyl)pentane (0.17 g, 0.5 mmol) and 1-chloropinacolone (81 mg, 0.6 mmol). After stirring for 16 h, the reaction is quenched with satd NaHCO$_3$ and extracted with diethyl ether. The organic layer is washed with water, Na$_2$SO$_4$ dried, concentrated, and chromatographed (7.5% EtOAc/Hex to 12% EtOAc/Hex) to give the title compound (0.12 g, 55%).

H-NMR (300 mHz, DMSO-d6): δ 7.20 (1H, d, J=8.2 Hz), 7.12 (1H, s), 7.04 (3H, m), 6.76 (2H, d, J=8.2 Hz), 5.05 (2H, s), 3.41 (3H, s), 2.24 (3H, s), 2.04 (4H, q, J=7.4 Hz), 1.15 (9H, s), 0.55 (6H, t, J=7.4 Hz).

ES/MS: 464.3 (m+NH4).

Example 37

Preparation of 3'-[4-(2-hydroxy-3,3-dimethylbutoxy)-phenyl]-3'-[4-methylsulfonyloxy-3-methylphenyl]pentane

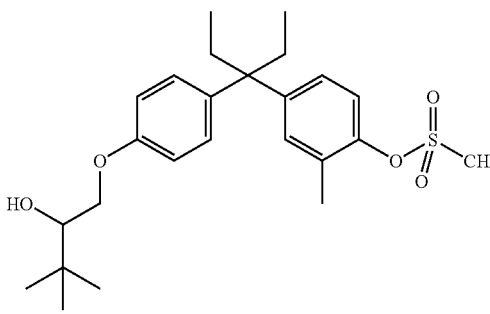

To a mixture of 3'-[4-(2-oxo-3,3-dimethylbutoxy)-phenyl]-3'-[4-methylsulfonyloxy-3-methylphenyl]pentane (84 mg, 0.19 mmol) and EtOH (2 ml) is added sodium borohydride (7 mg, 0.19 mmol). After stirring for 30 m, the mixture is quenched with satd NaHCO$_3$ and water and extracted with diethyl ether. The organic layer is Na$_2$SO$_4$ dried, concentrated, and chromatographed (7.5% EtOAc/Hex to 15% EtOAc/Hex) to give the title compound (59 mg, 69%).

H-NMR (400 mHz, CDCl3): δ 7.13 (1H, d, J=8.4 Hz), 7.04 (4H, m), 6.80 (2H, d, J=8.8 Hz), 4.09 (2H, d, J=10.0 Hz), 3.84 (1H, t, J=9.8 Hz), 3.67 (1H, d, J=10 Hz), 3.16 (3H, s), 2.29 (3H, s), 2.03 (4H, q, J=7.0 Hz), 0.99 (9H, s), 0.60 (6H, t, J=7.0 Hz).

FAB/MS: 448.2 (m+).

Example 38

Preparation of 3'-[4-(2-oxo-3,3-dimethylbutoxy)-3-methylphenyl]-3'-[4-methylsulfonyloxy-phenyl]pentane

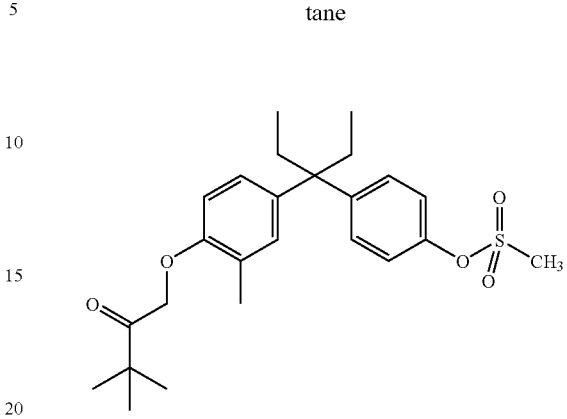

A. z/e-3-(4-Hydroxyphenyl)-3-pentene

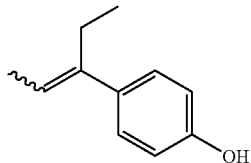

Using a procedure analogous to Example 36C, 3-(4-methoxyphenyl)-3-pentanol (0.4 g, 2 mmol) and 1M boron tribromide (4 ml, 4 mmol) give the title compound (0.28 g, 86%).

H-NMR (400 mHz, CDCl$_3$): 5.63 (0.6H, q, J=6.8 Hz), 5.48 (0.4H, q, J=6.8 Hz).

B. z/e-3'-(4-Methylsulfonyloxyphenyl)-3'-pentene

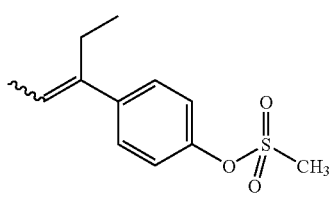

Using a procedure analogous to Example 36B, z/e-3-(4-hydroxyphenyl)-3-pentene (0.28 g, 1.7 mmol) gives the title compound (0.34 g, 84%).

H-NMR (400 mHz, CDCl3): 5.72 (0.6H, q, J=6.9 Hz), 5.54 (0.4H, q, J=6.9 Hz).

C. 3'-(4-Hydroxy-3-methylphenyl)-3'-(4-methylsulfonyloxy-phenyl)pentane

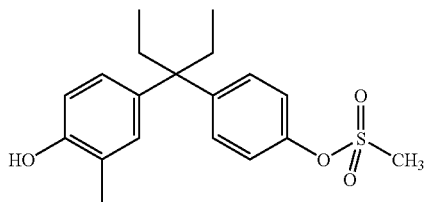

Using a procedure analogous to Example 36A, z/e-3'-(4-methylsulfonyloxyphenyl)-3'-pentene (0.34 g, 1.4 mmol) gives the title compound (0.33 g, 68%).

H-NMR (400 mHz, CDCl3): 7.19 (2H, d, J=8.0 Hz), 7.14 (2H, d, J=8.0 Hz), 6.85 (1H, s), 6.83 (1H, d, J=7.2 Hz), 6.64 (1H, d, J=7.2 Hz), 4.58 (1H, m), 3.11 (3H, s), 2.19 (3H, s), 2.03 (4H, q, J=7.4 Hz), 0.59 (6H, t, J=7.4 Hz).
ES/MS: 366.3 (M+NH4), 347.2 (m−1).

D. 3'-[4-(2-Oxo-3,3-dimethylbutoxy)-3-methylphenyl]-3'-[4-methylsulfonyloxy-phenyl]pentane

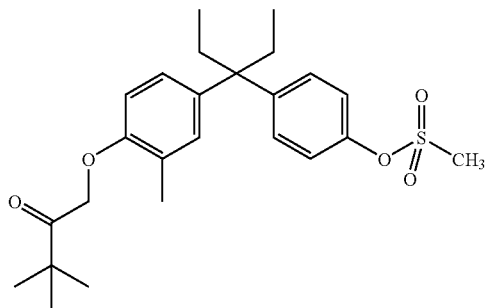

Using a procedure analogous to Example 36D, 3'-(4-hydroxy-3-methylphenyl)-3'-(4-methylsulfonyloxy-phenyl)pentane (0.17 g, 0.5 mmol) gives the title compound (0.14 g, 63%).

H-NMR (300 mHz, DMSO-d6): δ 7.25 (4H, s), 6.92 (1H, s), 6.88 (1H, d, J=8.2 Hz), 6.61 (1H, d, J=8.2 Hz), 5.06 (2H, s), 3.35 (3H, s), 2.14 (3H, s), 2.04 (4H, q, J=8.2 Hz), 1.16 (9H, s), 0.54 (6H, t, J=8.2 Hz).
FAB/MS: 446.2 (M+).

Example 39

Preparation of 3'-[4-(2-oxo-3,3-dimethylbutoxy)-3-ethylphenyl]-3'-[4-methylsulfonyloxy-phenyl]pentane

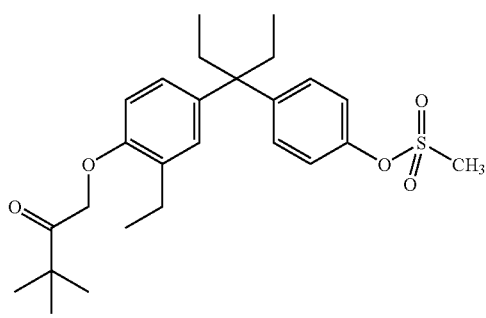

A. 3'-(4-Hydroxy-3-ethylphenyl)-3'-(4-methylsulfonyloxy-phenyl)pentane

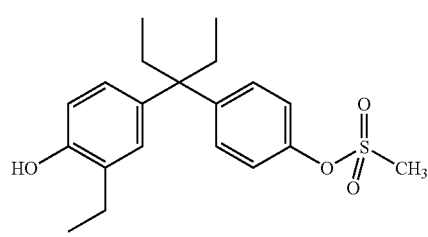

Using a procedure analogous to Example 36A, z/e-3'-(4-methylsulfonyloxyphenyl)-3'-pentene (0.2 g, 0.8 mmol) gives the title compound (0.135 g, 45%).

H-NMR (400 mHz, CDCl3): 7.20 (2H, d, J=8.8 Hz), 7.14 (2H, d, J=8.8 Hz), 6.88 (1H, s), 6.80(1H, d, J=8.4 Hz), 6.64 (1H, d, J=8.4 Hz), 4.60(1H, m), 3.11 (3H, s), 2.56 (2H, q, J=7.2 Hz), 2.03 (4H, m), 1.16(3H, t, J=7.2 Hz), 0.60(6H, t, J=7.4 Hz).
ES/MS: 380.2 (M+NH4), 361.1 (m−1).

B. 3'-[4-(2-Oxo-3,3-dimethylbutoxy)-3-ethylphenyl]-3'-[4-methylsulfonyloxy-phenyl]pentane

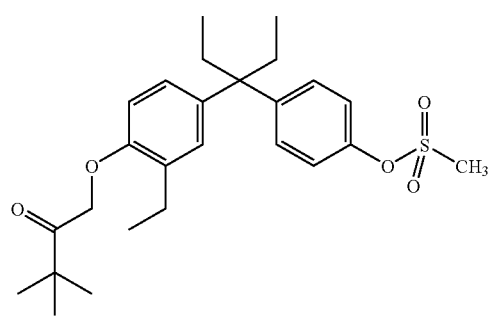

Using a procedure analogous to Example 36D, 3'-(4-hydroxy-3-ethylphenyl)-3'-(4-methylsulfonyloxy-phenyl)pentane (0.14 g, 0.4 mmol) gives the title compound (70 mg, 40%).

H-NMR (300 mHz, DMSO-d6): δ 7.25 (4H, s), 6.92 (1H, s), 6.88 (1H, d, J=8.2 Hz), 6.62 (1H, d, J=8.2 Hz), 5.06 (2H, s), 3.35 (3H, s), 2.55 (2H, q, J=6.8 Hz), 2.04 (4H, q, J=6.8 Hz), 1.16 (9H, s), 1.07 (3H, t, J=6.8 Hz), 0.54 (6H, t, J=6.8 Hz).

Example 40

Preparation of 3'-[4-(2-oxo-3,3-dimethylbutoxy)-3-methylphenyl]-3'-[3,5-dimethyl-4-methylsulfonyloxy-phenyl]pentane

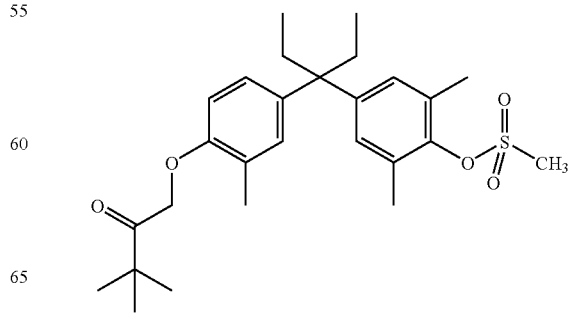

A. z/e-3'-(3,5-Dimethyl-4-methylsulfonyloxyphenyl)-3'-pentene

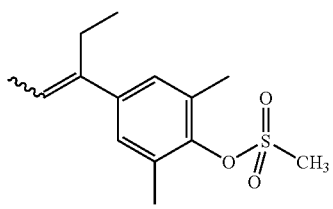

Using a procedure analogous to Example 36C, 3'-(3,5-dimethyl-4-methoxyphenyl)-3'-pentanol (2.2 g, 10 mmol) is reacted for 3 h to give crude z/e-3'-(3,5-dimethyl-4-hydroxyphenyl)-3'-pentene [ES/MS: 191.1 (M+1) 189.1 (M−1)]. Using a procedure analogous to Example 36B, crude z/e-3'-(3,5-dimethyl-4-hydroxyphenyl)-3'-pentene gives the title compound (2.12 g, 79% crude).

H-NMR (400 mHz, CDCl3): 5.68 (0.7H, q, J=6.6 Hz), 5.48 (0.3H, q, J=6.6 Hz).

ES/MS: 269.1 (M+1)

B. 3'-(4-Hydroxy-3-methylphenyl)-3'-(3,5-dimethyl-4-methylsulfonyloxy-phenyl)pentane

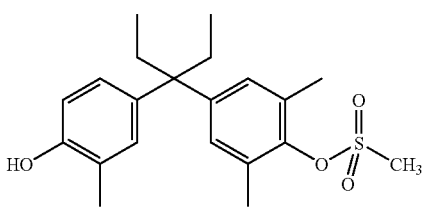

Using a procedure analogous to Example 36A, z/e-3'-(3,5-dimethyl-4-methylsulfonyloxyphenyl)-3'-pentene (0.27 g, 1 mmol) gives the title compound (0.29 g, 76%).

H-NMR (400 mHz, CDCl3): 6.8-6.9 (4H, m), 6.64 (2H, d, J=8.4 Hz), 4.60 (1H, m), 3.25 (3H, s), 2.30 (6H, s), 2.19 (3H, s), 1.99 (4H, q, J=7.2 Hz), 0.58 (6H, t, J=7.2 Hz).

ES/MS: 394.3 (M+NH4), 375.1 (m−1).

C. 3'-[4-(2-Oxo-3,3-dimethylbutoxy)-3-methylphenyl]-3'-[3,5-dimethyl-4-methylsulfonyloxy-phenyl]pentane

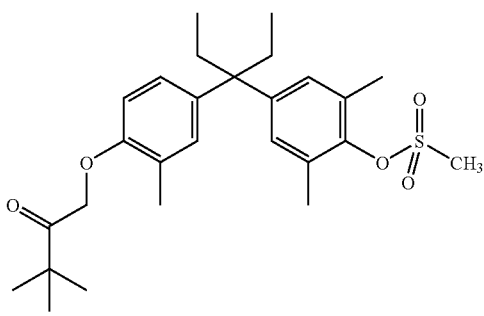

Using a procedure analogous to Example 36D, 3'-(4-hydroxy-3-methylphenyl)-3'-(3,5-dimethyl-4-methylsulfonyloxy-phenyl)pentane (0.29 g, 0.76 mmol) gives the title compound (176 mg, 49%).

H-NMR (300 mHz, DMSO-d6): δ 6.83-6.95 (4H, m), 6.61 (1H, d, J=7.5 Hz), 5.05 (2H, s), 3.26 (3H, s), 2.30 (6H, s), 2.24 (3H, s), 2.00 (4H, q, J=6.8 Hz), 1.15 (9H, s), 1.07 (3H, t, J=6.8 Hz), 0.51 (6H, t, J=6.8 Hz).

FAB/MS: 474.1 (M+).

Example 41

Preparation of 3'-[4-(2-oxo-3,3-dimethylbutoxy)-phenyl]-3'-[3,5-dimethyl-4-methylsulfonyloxy-phenyl]pentane

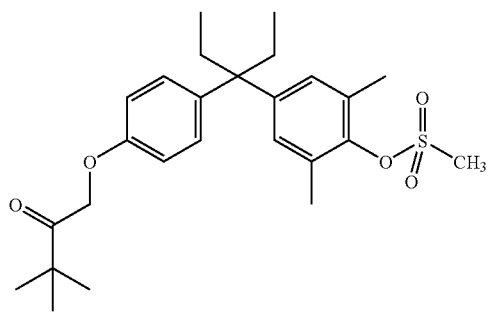

A. 3'-(4-Methoxyphenyl)-3'-(3,5-dimethyl-4-methylsulfonyloxy-phenyl)pentane

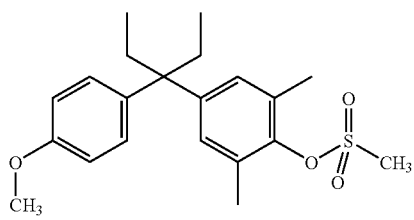

Using a procedure analogous to Example 36A, z/e-3'-(3,5-dimethyl-4-methylsulfonyloxyphenyl)-3'-pentene (0.27 g, 1 mmol) and anisole (0.54 g, 5 mmol) are reacted for 64 h to give the title compound (0.22 g, 58%).

H-NMR (400 mHz, CDCl3): 7.04 (2H, d, J=8.8 Hz), 6.84 (2H, s), 6.78 (2H, d, J=8.8 Hz), 3.78 (3H, s), 3.26 (3H, s), 2.30 (6H, s), 2.01 (4H, q, J=7.2 Hz), 0.59 (6H, t, J=7.2 Hz).

B. 3'-(4-Hydroxyphenyl)-3'-(3,5-dimethyl-4-methyl-sulfonyloxy-phenyl)pentane

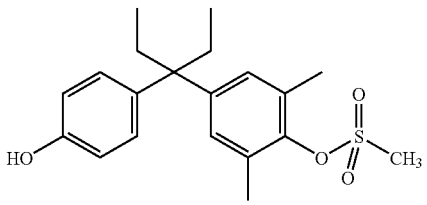

Using a procedure analogous to Example 36C, 3'-(4-methoxyphenyl)-3'-(3,5-dimethyl-4-methylsulfonyloxy-phenyl)pentane (0.22 g, 0.6 mmol) is reacted for 8 h to give the title compound (0.2 g, 95%).

H-NMR (400 mHz, CDCl3): 7.00 (2H, d, J=8.8 Hz), 6.84 (2H, s), 6.71 (2H, d, J=8.8 Hz), 4.60 (1H, s), 3.26 (3H, s), 2.30 (6H, s), 2.00 (4H, q, J=7.6 Hz), 0.58 (6H, t, J=7.6 Hz).

C. 3'-[4-(2-Oxo-3,3-dimethylbutoxy)-phenyl]-3'-[3,5-dimethyl-4-methylsulfonyloxy-phenyl]pentane

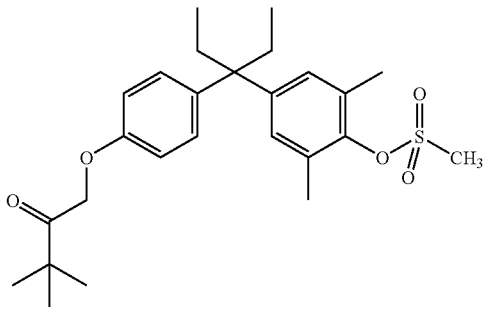

Using a procedure analogous to Example 36D, 3'-(4-hydroxyphenyl)-3'-(3,5-dimethyl-4-methylsulfonyloxy-phenyl)pentane (0.19 g, 0.54 mmol) gives the title compound (173 mg, 70%).

H-NMR (300 mHz, DMSO-d6): δ 7.04 (2H, d, J=8.2 Hz), 6.90 (2H, s), 6.75 (2H, d, J=8.2 Hz), 5.04 (2H, s), 3.26 (3H, s), 2.24 (6H, s), 2.02 (4H, q, J=7.0 Hz), 1.15 (9H, s), 0.53 (6H, t, J=7.0 Hz).

ES/MS: 478.3 (M+NH4).

Example 42

Preparation of 3'-[3-chloro-4-(2-oxo-3,3-dimethylbutoxy)phenyl]-3'-[4-(methylsulfonyloxy)phenyl]pentane

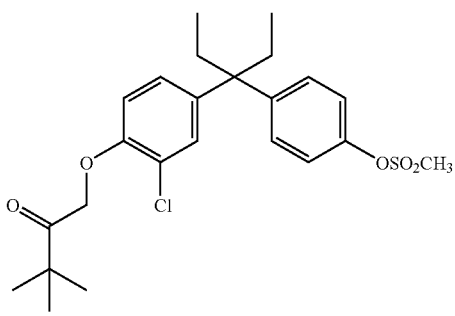

A. 3-(3-Chloro-4-hydroxyphenyl)-3-pentanol

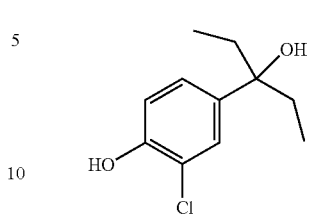

To a solution of methyl 3-chloro-4-hydroxybenzoate (25.0 g, 133 mmol) in THF (250 mL) is added dropwise 1.0 M ethylmagnesium bromide/THF (442 mL, 442 mmol) at a rate maintaining the temperature below 27° C. The brownish grey reaction is stirred for 72 h. The reaction mixture is cooled in an ice bath and quenched with satd ammonium chloride (1 ml portions) until evolution of ethane subsides. Additional satd NH4Cl solution is added (total of 50 mL) and the mixture is concentrated to remove most of the THF. The residue is added to water and ether, filtered through diatomaceous earth, and partitioned. The organic layer is washed with brine (3×), MgSO4 dried, and concentrated to give the title compound (28.6 g, 99%).

H-NMR (300 mHz, CDCl3): δ 7.38 (1H, d, J=1.6 Hz), 7.07 (1H, dd, J=8.4 Hz, J=1.6 Hz), 6.95 (1H, d, J=8.4 Hz), 5.53 (1H, br s), 1.80 (4H, m), 0.76 (6H, t, J=7.6 Hz).

IR (CHCl3): 3600 cm$^{-1}$, 3540 cm$^{-1}$ 1

TOF MS EI+ 214.076; Calc. m/z. 214.0761

B. [E, Z]-3-(3-Chloro-4-hydroxyphenyl)-3-pentene

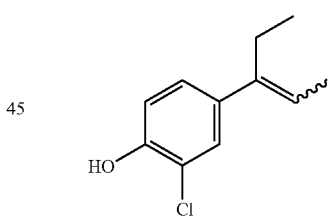

A mixture of 3-(3-chloro-4-hydroxyphenyl)-3-pentanol (10.0 g, 46.5 mmol), pTSA monohydrate (20 mg, catalytic amount), and toluene (300 mL) is heated on a steam bath for 3 h. The toluene solution is cooled to RT, washed with satd sodium carbonate solution (25 mL), MgSO4 dried, and concentrated to give the title compounds as a [E:Z] isomeric mixture of [85:15] (9.2 g, quant).

TLC (CHCl3): Rf ~0.7

H-NMR (300 mHz, DMSO-d6): δ 6.85-7.30 (3H, m), 5.65 (0.85H, q, J=6.8 Hz), 5.43 (0.15H, q, J=6.8 Hz), 2.43((1.7H, q, J=7.6 Hz), 2.28 (0.3H, q, J=7.6 Hz), 1.72 (2.55H, d, J=7.6 Hz), 1.52 (0.45H, d, J=7.6 Hz), 0.90 (2.55H, t, J=7.6 Hz)), 0.85 (0.45H, t, J=7.6 Hz).

C. [E,Z]-3-[3-Chloro-4-(2-oxo-3,3-dimethylbutoxy)phenyl]-3-pentene

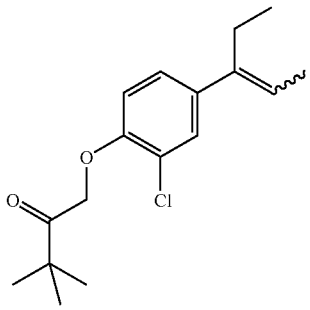

A mixture of [EZ]-3-(3-Chloro-4-hydroxyphenyl)-3-pentene (4.00 g, 20.3 mmol) and 1-chloropinacolone (2.73 g, 20.3 mmol), anhydrous KI (0.17 g, 1.0 mmol), K$_2$CO$_3$ (14.0 g, 102 mmol) and acetonitrile (80 mL) is refluxed for 3 h. The reaction is cooled to RT and concentrated. The residue is partitioned between methylene chloride (50 mL) and ice water (50 mL). The organic layer is MgSO$_4$ dried, concentrated, and chromatogrpahed (40% to 70% chloroform in hexane) to give the title compounds as an 85:15 [E. Z] mixture (5.07 g, 85%).

H-NMR (300 mHz, DMSO-d6): δ 7.37 (0.85H, d, J=2.1 Hz), 7.22 (0.85H, dd, J=2.1, J=8.6 Hz), 7.18 (0.15H, d, J=2.1 Hz), 7.03 (0.15H, dd, J=2.0 Hz, J=8.4 Hz), 6.88 (0.15H, d, J=8.4 Hz), 6.85 (0.85H, d, J=8.6 Hz), 5.71 (0.85H, m), 5.52 (0.15H, m), 5.25 (2H, s), 2.45 (1.70H, q, J=7.6 Hz), 2.30 (0.30H, q, J=7.6 Hz), 1.75 (2.55H, d, J=7.6 Hz), 1.53 (0.45H, d, J=7.6 Hz), 1.17 (9H, s), 0.91 (2.55H, t, J=7.6 Hz), 0.88 (0.45H, t, J=7.6 Hz).

TOF MS EI+: 294.139; Calc. m/z 294.1387.

D. 3'-[3-Chloro-4-(2-oxo-3,3-dimethylbutoxy)phenyl]-3'-(4-hydroxyphenyl)pentane

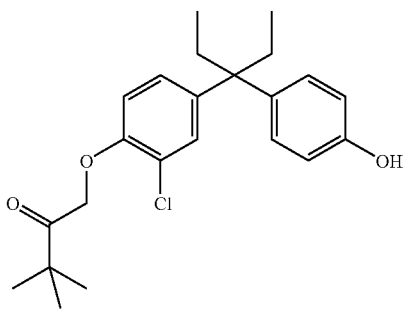

A −20° C. solution of [E,Z]-3-[3-chloro-4-(2-oxo-3,3-dimethylbutoxy)phenyl]-3-pentene (4.5 g, 15.2 mmol), phenol (17.2 g, 183 mmol) and methylene chloride (30 mL) is treated with BF3-etherate (0.863 g, 6.1 mmol) and stirred for 30 m while maintaining the temperature near −20° C. The resulting light reddish brown solution is allowed to warm to 0° C. and kept at that temperature for 16 h. The reaction is distilled at 45° C./0.04 mm to remove most of the excess phenol. The residue is treated with powderized NaHCO$_3$ (600 mg), ethylene glycol (15 ml), and distilled to remove the last of the phenol and almost all of the glycol. The resulting viscous tan oily residue is cooled to RT and distributed between sat NaHCO$_3$ (25 mL) and ethyl acetate (200 mL). The organic layer is separated, washed with water (5×50 mL), Na$_2$SO$_4$ dried, and concentrated to give the title compound as an oil (5.8 g, 98%).

H-NMR (300 mHz, CDCl3): 7.21 (1H, d, J=2.3 Hz), 6.99 (2H, d, J=8.7 Hz), 6.95 (1H, dd, J=2.3 Hz, J=8.6 Hz), 6.75 (2H, d, J=8.7 Hz), 6.62 (1H, d, J=8.6 Hz), 4.91 (2H, s), 4.86 (1H, s), 2.02 (4H, q, J=7.3 Hz), 1.28 (9H, s), 0.62 (6H, t, J=7.3 Hz).

ES(+) MS m/z: 389.3 (M+H); calc. m/z 389.1883 (M+H).

E. 3'-[3-Chloro-4-(2-Oxo-3,3-dimethylbutoxy)phenyl]-3'-(4-methylsulfonyloxyphenyl)pentane

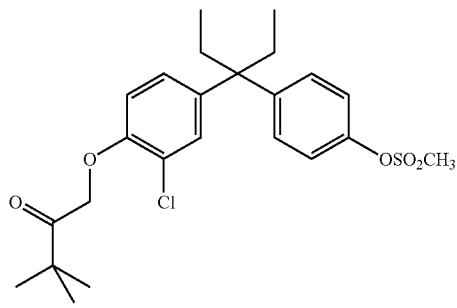

Using a procedure analogous to Example 17 with brine and satd NaHCO$_3$ washes, 3'-[3-chloro-4-(2-oxo-3,3-dimethylbutoxy)phenyl]-3'-(4-hydroxyphenyl)pentane gives the title compound as a colorless oil (1.16 g., 97%).

H-NMR (300 mHz, CDCl3): δ 7.15-7.20 (1H, m), 6.91 (2H, dd, J=2.3 Hz, J=8.7 Hz), 6.61 (1H, d, J=8.7 Hz), 4.91 (2H, s), 3.14 (3H, s), 2.04 (4H, q, J=7.4 Hz), 1.26 (9H, s), 0.62 (6H, t, J=7.4 Hz).

IR (CHCl3) 1727.91 cm$^{-1}$.

ES(+) MS m/z: 489.2 (M+Na); Calc. m/z 489.1478 (M+Na).

Example 43

Preparation of racemic 3'-[3-chloro-4-(2-hydroxy-3,3-dimethylbutoxy)phenyl]-3'-(4-methylsulfonyloxyphenyl)pentane

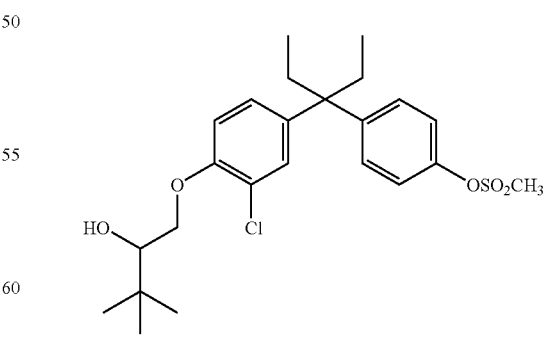

Using a procedure analogous to Example 1C with acetone quench, 3'-[3-chloro-4-(2-oxo-3,3-dimethylbutoxy)phenyl]-3'-(4-methylsulfony-oxyphenyl)pentane gives the title compound as an oil (646 mg, 99%).

H-NMR (300 mHz, DMSO-D6): δ 7.0-7.3 (7H, m), 4.74 (1H, d), 4.11 (1H, dd), 3.86 (1H, dd), 4.97 (1H, m), 3.36 (3H, s), 3.32 (1H, s), 2.06 (4H, q, J=7.3 Hz), 0.93 (9H, s), 0.57 (6H, t, J=7.3 Hz).

IR (CHCl$_3$): 3587.94 cm-1.

ES(+) MS m/z: 486.3 (M+NH4), 491.2 (M+Na); Calc. 486.2081 (M+NH4), 491.1713 (M+Na).

Example 44 and Example 45

Preparation of enantiomers of 3'-[3-chloro-4-(2-hydroxy-3,3-dimethylbutoxy)phenyl]-3'-(4-methylsulfonyloxyphenyl)pentane

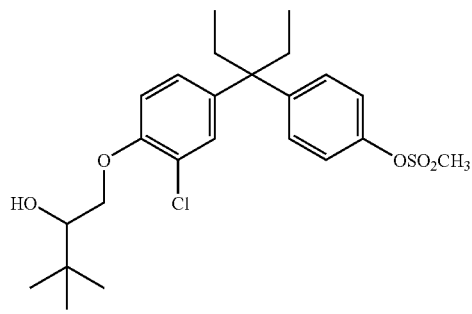

A racemic mixture 3'-[3-chloro-4-(2-hydroxy-3,3-dimethylbutoxy)phenyl]-3'-(4-methylsulfonyloxyphenyl)pentane (558 mg) is chromatographed with a Chiralcel AD column to give enantiomer 1, Example 44 (199 mg, 36%) and enantiomer 2, Example 45 (193 mg, 35%).

Enantiomer 1, Example 44

HPLC: Chiralpak AD (4.6×150 mm); 100% 3A Alcohol; 0.6 mL/m (flow rate); rt 6.1 m; 240 nm; ee 100% by HPLC.

H-NMR (300 mHz, CDCl3): δ7.1-7.3 (5H, m), 6.95 (1H, dd, J=2.1, J=8.6), 6.83 (1H, d, J=8.6), 4.17 (1H, dd), 3.88 (1H, t), 3.72 (1H, m), 3.17 (3H, s), 2.58 (1H, d), 2.05 (4H, q, J=7.3 Hz), 1.03 (9H, s), 0.62 (6H, t, J=7.3 Hz).

FAB(+) MS m/z [M]: 468.2; calc. m/z 468.1737.

Enantiomer 2, Example 45

HPLC: Chiralpak AD (4.6×150 mm); 100% 3A Alcohol; 0.6 mL/m (flow rate); rt=8.6 m; 240 nm; ee 98.4% by HPLC.

H-NMR (300 mHz, CDCl3): δ 7.1-7.3 (5H, m), 6.95 (1H, dd, J=2.1, J=8.6), 6.83 (1H, d, J=8.6), 4.17 (1H, dd), 3.88 (1H, t), 3.72 (1H, m), 3.17 (3H, s), 2.58 (1H, d), 2.05 (4H, q, J=7.3 Hz), 1.03 (9H, s), 0.62 (6H, t, J=7.3 Hz).

FAB(+) MS m/z [M]: 468.3; calc. m/z 468.1737.

Example 46

Preparation of 3'-[3-chloro-4-(2-Oxo-3,3-dimethylbutoxy)]-3'-(4-trifluoromethylsulfonyloxyphenyl)pentane

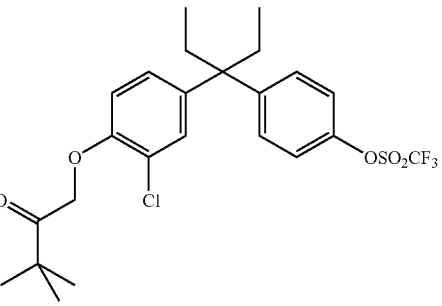

Using a procedure analogous to Example 17 at RT with potassium phosphate monobasic/sodium hydroxide buffer quench, 3'-[3-chloro-4-(2-oxo-3,3-dimethylbutoxy)phenyl]-3'-(4-hydroxyphenyl)pentane and triflic anhydride give the title compound as a colorless oil (3.7 g, 69%).

H-NMR (300 mHz, DMSO-D6): δ 7.40 (2H, d, J=8.7 Hz), 7.33 (2H, d, J=8.7 Hz), 7.15 (1H, d, J=2.1 Hz), 6.68 (1H, dd, J=2.1 Hz, J=8.6 Hz), 6.78 (2H, d, J=8.6 Hz), 5.22 (2H, s), 2.07 (4H, q, J=7.3 Hz), 1.17 (9H, s), 0.62 (6H, t, J=7.3 Hz).

FAB+MS: 521.0 (M+H); calc. 521.1376 (M+H).

ES MS: 521.3 (M+1), 538.3 (M+NH4), 543.2 (M+Na)

Example 47

Preparation of 3'-[3-chloro-4-(2-hydroxy-3,3-dimethylbutoxy)phenyl]-3'-(4-trifluoromethylsulfonyloxyphenyl)pentane

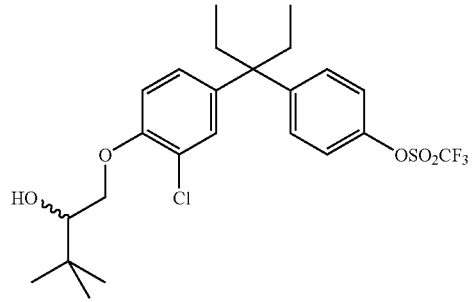

Using a procedure analogous to Example 1C, 3'-[3-chloro-4-(2-oxo-3,3-dimethylbutoxy)phenyl]-3'-(4-trifluoromethylsulfonyloxyphenyl)pentane gives the title compound as a colorless oil (495 mg, 99%).

H-NMR (300 mHz, CDCl3): δ 7.21 (2H, d, J=8.8 Hz), 7.16 (2H, d, J=8.8 Hz), 6.97 (1H, dd, J=2.3 Hz, J=8.6 Hz), 6.84 (1H, d, J=8.6 Hz), 4.18 (1H, dd, J=2.6 Hz, J=9.0 Hz), 3.89 (t, J=8.9 Hz,), 3.73 (1H, dt, J=2.6, J=8.9, J=3.0), 2.57, (1H, d, J=3.0 Hz), 2.06 (4H, q, J=7.3 Hz), 1.04 (9H, s), 0.62 (6H, t, J=7.3 Hz).

FAB(+) MS m/z [M]: 522.1; calc. 522.1455.

ES (+) MS m/z: 540.3 (M+NH4); calc 540.1798.

Example 48

Preparation of 3'-[3-chloro-4-(2-oxo-3.3-dimethylbutoxy)phenyl]-3'-[3-methyl-4-(trifluoromethylsulfonyloxy)phenyl]pentane

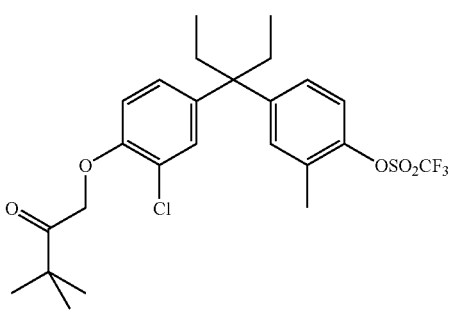

A. [E,Z]-3-[3-Chloro-4-(trifluoromethylsulfonyloxy)phenyl]-3-pentene

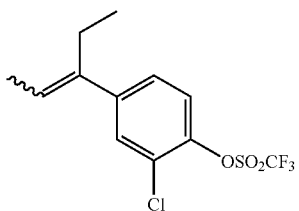

Using a procedure analogous to Example 17, [E,Z]-3-(3-chloro-4-hydroxyphenyl)-3-pentene, triflic anhydride, and diisopropylethylamine give the title compound as a brown oil in a [E:Z] ratio of 3:1 (8.7 g, quant).

H-NMR (300 mHz, CDCl3): δ 7.01-7.40 (3H, m), 5.67 (0.75H, q, J=6.9 Hz), 5.53 (0.25H, q, J=6.9 Hz), 2.41((1.5H, q, J=7.6 Hz), 2.24 (0.5H, q, J=7.6 Hz), 1.84 (2.25H, d, J=7.6 Hz), 1.48 (0.75H, d, J=7.6 Hz), 0.91 (2.25H, t, J=7.6 Hz)), 0.86 (0.75H, t, J=7.6 Hz).

TOF MS EI+:328.015; calc. 328.0226.

B. 3'-(4-hydroxy-3-methylphenyl)-3'-[3-chloro-4-(methylsulfonyloxy)-phenyl]pentane

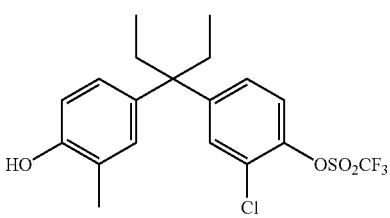

Using a procedure analogous to Example 42D, [E,Z]-3-[3-chloro-4-(trifluoromethylsulfonyloxy)phenyl]-3-pentene and o-cresol give the title compound as a pale tan oil (4.29 g, 38%).

H-NMR (300 mHz, CDCl3): 6.5 to 7.3 (6H, m) 4.57 (1H, s), 2.21 (3H, s), 2.05 (4H, q, J=7.3 Hz), 0.62 (6H, t, J=7.3 Hz).

ES(−) MS m/z: 435.1 (M−H); calc. 435.0645.

C. Preparation of 3'-[3-chloro-4-(2-oxo-3.3-dimethylbutoxy)-phenyl]-3'-[3-methyl-4-(trifluoromethylsulfonyloxy)phenyl]pentane NOTE: Triflate Rearrangement Procedure

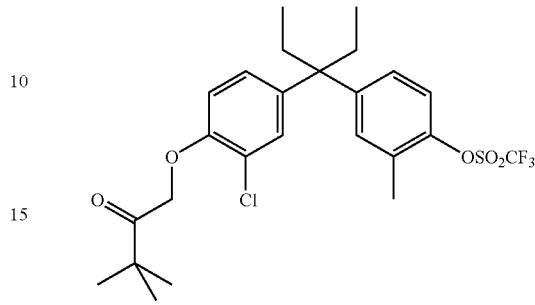

Using a procedure analogous to Example 42C, 3'-(3-chloro-4-hydroxyphenyl)-3'-[3-methyl-4-(methylsulfonyloxy)phenyl]pentane and chromatographies (30% to 50% chloroform/Hex; Hex to 10% EtOAc/Hex) to give the title compound (2.61 g, 53%).

H-NMR (300 mHz, CDCl3): δ 7.15 (1H, d, J=2.3 Hz), 7.11 (1H, d, J=8.4 Hz), 7.04 (1H, d, J=2.3 Hz), 7.02 (1H, dd, J=2.3 Hz, J=8.4 Hz), 6.89 (1H, dd, J=8.6 Hz, J=2.3 Hz), 6.62 (1H, d, J=8.6 Hz), 4.91 (2H, s), 2.32 (3H, s), 2.03 (4H, q, J=7.2 Hz), 1.26 (9H, s), 0.60 (6H, t, J=7.2 Hz).

ES(+) MS m/z: 552.2 (M+NH4); calc. 552.1798

FAB(+) MS m/z [M]: 534.9; calc. 534.

Example 49

Preparation of 3'-[3-chloro-4-(2-hydroxy-3.3-dimethylbutoxy)phenyl]-3'-[3-methyl-4-(trifluoromethylsulfonyloxy)phenyl]pentane

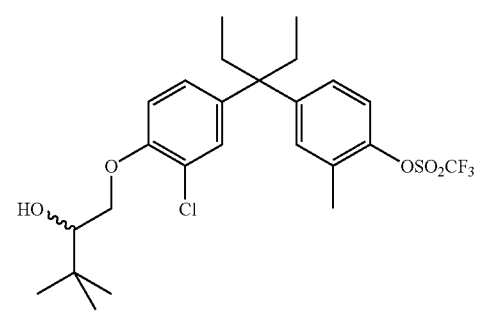

Using a procedure analogous to Example 1C, 3'-[3-chloro-4-(2-oxo-3,3-dimethylbutoxy)phenyl]-3'-[3-methyl-4-(methylsulfonyloxy)phenyl]pentane gives the title compound (719 mg, 98%).

H-NMR (300 mHz, CDCl3): δ7.15 (1H, d, J=2.3 Hz), 7.13 (1H, d, J=8.4 Hz), 7.05 (1H, d, J=2.0 Hz), 7.03 (1H, dd, J=2.3 Hz, J=8.4 Hz), 6.96 (1H, dd, J=8.6 Hz, J=2.3 Hz), 6.86 (1H, d, J=8.6 Hz), 4.20 (1H, dd, J=8.9, 2.5 Hz), 3.906 (1H, t, J=8.9 Hz), 3.75 (1H, dd, J=8.9, 2.5 Hz), 2.59 (1H, br s), 2.34 (3H, s), 2.06 (4H, q, J=7.3 Hz), 1.03 (9H, s), 0.63 (6H, t, J=7.3 Hz).

ES(+) MS m/z: 554.2 (M+NH4); calc. 554.1954.

FAB(+) MS m/z [M]: 536.1; calc. 536.1661

Example 50

Preparation of 3'-[3-chloro-4-(2-oxo-3,3-dimethylbutoxy)phenyl]-3'-[4-(methylsulfonyloxy)phenyl]pentane

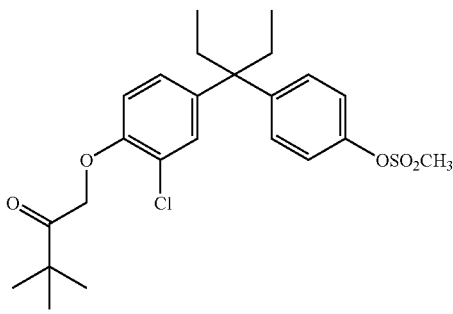

A. 3-(3-Chloro-4-hydroxyphenyl)-3-pentanol

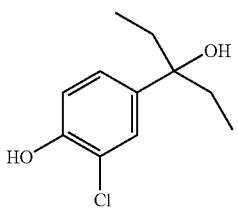

To a solution of methyl 3-chloro-4-hydroxybenzoate (25.0 g, 133 mmol) in THF (250 mL) is added dropwise 1.0 M ethylmagnesium bromide in THF (442 mL, 442 mmol) so as to maintain the temperature below 27° C. The resulting brownish grey solution is allowed to stir for 72 h during which time a cream-colored gelatinous precipitate is formed. The reaction mixture is cooled in an ice bath and quenched with 1 mL portions of sat. ammonium chloride solution until evolution of ethane subsides. Additional NH$_4$Cl solution is added (to a total of 50 mL) and the resulting mixture is concentrated to remove most of the THF. The resulting residue is distributed into water and ether and filtered through diatomaceous earth to break the partial emulsion that forms. The organic layer is washed 3 times with sat. NaCl, dried over anhydrous magnesium sulfate and concentrated under vacuum to give the title compound (28.6 g, 99%).

H-NMR (300 mHz, CDCl3): δ 7.38 (1H, d, J=1.6 Hz), 7.07 (1H, dd, J=8.4 Hz, J=1.6 Hz), 6.95 (1H, d, J=8.4 Hz), 5.53 (1H, br s), 1.80 (4H, m), 0.76 (6H, t, J=7.6 Hz).

IR (CHCl$_3$): 3600 cm$^{-1}$, 3540 cm$^{-1}$ 1

TOF MS EI+ 214.076; Calc. m/z. 214.0761

B. [E, Z]-3-(3-Chloro-4-hydroxyphenyl)-3-pentene

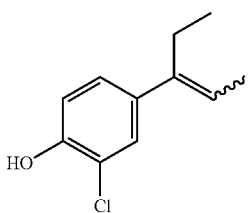

A mixture of 3-(3-chloro-4-hydroxyphenyl)-3-pentanol (10.0 g, 46.5 mmol), p toluene sulfonic acid monohydrate (20 mg, catalytic amount), and toluene (300 mL) heated on a steam bath for 3 h. Analysis by TLC (silica gel, CHCL$_3$) shows loss of the starting material and formation of a more mobile spot at Rf ~0.7. The toluene solution is allowed to cool to RT and is washed with sat. sodium carbonate solution (25 mL) and dried over anhydrous magnesium sulfate. Concentration under reduced pressure gives the title mixture of [E, Z]-isomeric compounds in a ratio of approximately 85:15, respectively (9.2 g, 100%). The product can be used without further purification.

H-NMR (300 mHz, DMSO-d6): δ 6.85-7.30 (3H, m), 5.65 (0.85H, q, J=6.8 Hz), 5.43 (0.15H, q, J=6.8 Hz), 2.43((1.7H, q, J=7.6 Hz), 2.28 (0.3H, q, J=7.6 Hz), 1.72 (2.55H, d, J=7.6 Hz), 1.52 (0.45H, d, =7.6 Hz), 0.90 (2.55H, t, J=7.6 Hz)), 0.85 (0.45H, t, J=7.6 Hz).

C. [E,Z]-3-[3-Chloro-4-(2-oxo-3,3-dimethylbutoxy)phenyl]-3-pentene

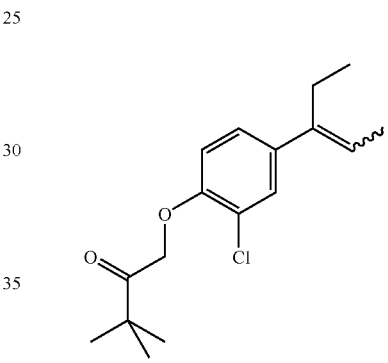

[E,Z]-3-(3-Chloro-4-hydroxyphenyl)-3-pentene (4.00 g, 20.3 mmol) and 1-chloropinacolone (2.73 g, 20.3 mmol), anhydrous KI (0.17 g, 1.0 mmol), K2CO3 (14.0 g, 102 mmol) and acetonitrile (80 mL) are combined and heated at reflux for 3 h. The reaction mixture is allowed to cool to RT and most of the solvent is removed by concentration under reduced pressure. The resulting solid residue is distributed between methylene chloride (50 mL) and ice water (50 mL) and the layers are separated. The organic layer is dried over anhydrous magnesium sulfate and concentrated to provide an oil, ~6.0 g. The crude product is purified by silica gel chromatography using a gradient of 40% to 70% chloroform in hexane. Concentration of fractions containing either or both of the desired isomers provides the title compounds as an 85:15 [E. Z] mixture, respectively (5.07 g, 85%).

H-NMR (300 mHz, DMSO-d6): δ 7.37 (0.85H, d, J=2.1 Hz), 7.22 (0.85H, dd, J=2.1, J=8.6 Hz), 7.18 (0.15H, d, J=2.1 Hz), 7.03 (0.15H, dd, J=2.0 Hz, J=8.4 Hz), 6.88 (0.15H, d, J=8.4 Hz), 6.85 (0.85H, d, J=8.6 Hz), 5.71 (0.85H, m), 5.52 (0.15H, m), 5.25 (2H, s), 2.45 (1.70H, q, J=7.6 Hz), 2.30 (0.30H, q, J=7.6 Hz), 1.75 (2.55H, d, J=7.6 Hz), 1.53 (0.45H, d, J=7.6 Hz), 1.17 (9H, s), 0.91 (2.55H, t, J=7.6 Hz), 0.88 (0.45H, t, J=7.6 Hz).

TOF MS EI+: 294.139; Calc. m/z 294.1387.

D. 3'-[3-Chloro-4-(2-oxo-3.3-dimethylbutoxy)phenyl]-3'-(4-hydroxyphenyl)pentane

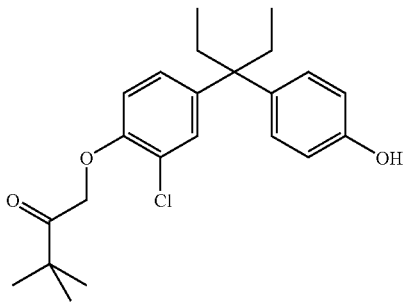

A solution of [E,Z]-3-[3-chloro-4-(2-oxo-3,3-dimethylbutoxy)phenyl]-3-pentene (4.5 g, 15.2 mmol) and phenol (17.2 g, 183 mmol) in methylene chloride (30 mL) is carefully cooled to −20° C. so as not to cause crystallization of the phenol. The cold solution is treated with BF$_3$-etherate (0.863 g, 6.1 mmol) and the resulting mixture is stirred for 30 m while the temperature is maintained near −20° C. The resulting light reddish brown solution is then allowed to warm to 0° C. and kept at that temperature for 16 h. The reaction mixture is placed under vacuum (0.04 mm, 45° C. oil bath) and distilled to remove most of the excess phenol. When the distillation slows, the residue is treated with powdered NaHCO$_3$ (600 mg) and ethylene glycol (15 ml) and the distillation is resumed to remove the last of the phenol and almost all of the glycol. The resulting viscous tan oily residue is cooled to RT and distributed between sat NaHCO$_3$ (25 mL) and ethyl acetate (200 mL). The organic layer is separated and washed with water (5×50 mL), dried over anhydrous sodium sulfate and concentrated to give the title product as a nearly colorless oil (5.8 g, 98%) which requires no further purification.

H-NMR (300 mHz, CDCl3): 7.21 (1H, d, J=2.3 Hz), 6.99 (2H, d, J=8.7 Hz), 6.95 (1H, dd, J=2.3 Hz, J=8.6 Hz), 6.75 (2H, d, J=8.7 Hz), 6.62 (1H, d, J=8.6 Hz), 4.91 (2H, s), 4.86 (1H, s), 2.02 (4H, q, J=7.3 Hz), 1.28 (9H, s), 0.62 (6H, t, J=7.3 Hz).

ES(+) MS m/z: 389.3 (M+H); calc. m/z 389.1883 (M+H).

E. 3'-[3-Chloro-4-(2-Oxo-3.3-dimethylbutoxy)phenyl]-3'-(4-methylsulfonyloxyphenyl)pentane

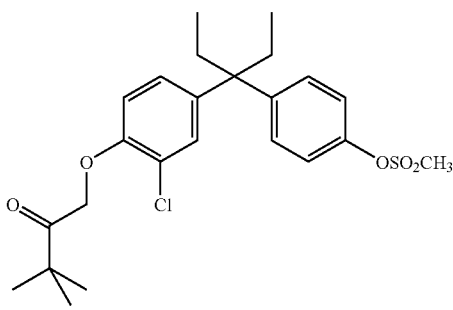

To 3'-[3-chloro-4-(2-oxo-3.3-dimethylbutoxy)phenyl]-3'-(4-hydroxyphenyl)pentane (1.00 g, 2.57 mmol) in methylene chloride (100 mL) is added successively by syringe triethyl amine (0.390 g, 3.85 mmol) and methanesulfonyl chloride (0.368, 0.25 mL, 3.21 mmol). After stirring the reaction mixture for 2 h, it is concentrated to near dryness and the residue is distributed between EtOAc (125 mL) and 0.1 N HCl (50 mL). The organic layer is separated and washed with sat. NaCl and with sat. NaHCO$_3$, dried over anhydrous magnesium sulfate and, concentrated. Drying of the residue under high vacuum provides the title compound as a colorless oil (1.16 g., 97%).

H-NMR (300 mHz, CDCl3): δ 7.15-7.20 (1H, m), 6.91 (2H, dd, J=2.3 Hz, J=8.7 Hz), 6.61 (1H, d, J=8.7 Hz), 4.91 (2H, s), 3.14 (3H, s), 2.04 (4H, q, J=7.4 Hz), 1.26 (9H, s), 0.62 (6H, t, J=7.4 Hz).

IR (CHCl$_3$) 1727.91 cm-1.

ES(+) MS m/z: 489.2 (M+Na); Calc. m/z 489.1478 (M+Na).

Example 51

Preparation of racemic 3'-[3-chloro-4-(2-hydroxy-3,3-dimethylbutoxy)phenyl]-3'-(4-methylsulfonyloxyphenyl)pentane

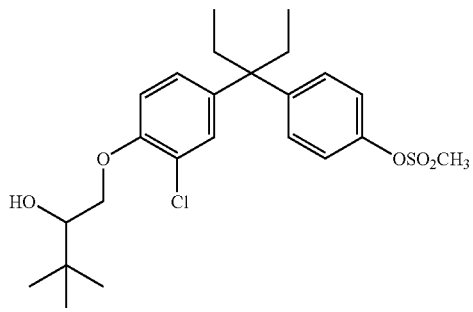

To 3'-[3-chloro-4-(2-oxo-3.3-dimethylbutoxy)phenyl]-3'-(4-methylsulfony-oxyphenyl)pentane (650 mg, 1.39 mmol) in 45 mL of MeOH at 0° C. is added sodium borohydride (55.4 mg, 1.46 mmol). The reaction mixture is allowed to warm to RT and after 16 h the excess reagent is destroyed by the addition of acetone (1 ml.). The resulting solution is concentrated to near dryness under reduced pressure and the residue is distributed between methylene chloride (20 mL) and water (20 mL). The organic layer is separated and the aqueous layer is extracted with additional methylene chloride (10 mL). The combined organic extracts are dried over anhydrous sodium sulfate and concentrated to an oil which is the title compound (646 mg, 99%).

H-NMR (300 mHz, DMSO-D6): δ 7.0-7.3 (7H, m), 4.74 (1H, d), 4.11 (1H, dd), 3.86 (1H, dd), 4.97 (1H, m), 3.36 (3H, s), 3.32 (1H, s), 2.06 (4H, q, J=7.3 Hz), 0.93 (9H, s), 0.57 (6H, t, J=7.3 Hz).

IR (CHCl$_3$): 3587.94 cm-1.

ES(+) MS m/z: 486.3 (M+NH4), 491.2 (M+Na); Calc. 486,2081 (M+NH4), 491.1713 (M+Na).

for Example 51A and Example 51B

Preparation of enantiomers of 3'-[3-chloro-4-(2-hydroxy-3,3-dimethylbutoxy)phenyl]-3'-(4-methylsulfonyloxyphenyl)pentane

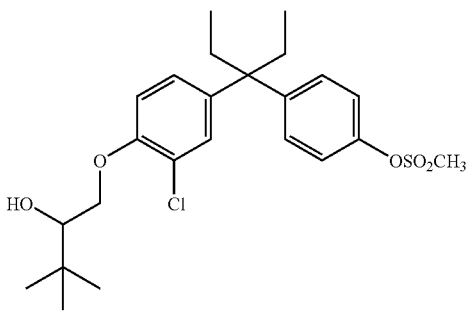

A racemic mixture 3'-[3-chloro-4-(2-hydroxy-3,3-dimethylbutoxy)phenyl]-3'-(4-methylsulfonyloxyphenyl)pentane (558 mg) is chromatographed with a Chiralcel AD column to give enantiomer 1, Example 2A (199 mg, 36%) and enantiomer 2, Example 2B (193 mg, 35%).

for Enantiomer 1, Example 51A

HPLC: Chiralpak AD (4.6×150 mm); 100% 3A Alcohol; 0.6 mL/m (flow rate); rt=6.1 m; 240 nm; ee 100% by HPLC.

H-NMR (300 mHz, CDCl3): δ 7.1-7.3 (5H, m), 6.95 (1H, dd, J=2.1, J=8.6), 6.83 (1H, d, J=8.6), 4.17 (1H, dd), 3.88 (1H, t), 3.72 (1H, m), 3.17 (3H, s), 2.58 (1H, d), 2.05 (4H, q, J=7.3 Hz), 1.03 (9H, s), 0.62 (6H, t, J=7.3 Hz).

FAB(+) MS m/z [M]: 468.2; calc. m/z 468.1737.

for Enantiomer 2, Example 51B

HPLC: Chiralpak AD (4.6×150 mm); 100% 3A Alcohol; 0.6 mL/m (flow rate); rt=8.6 m; 240 nm; ee 98.4% by HPLC.

H-NMR (300 mHz, CDCl3): δ 7.1-7.3 (5H, m), 6.95 (1H, dd, J=2.1, J=8.6), 6.83 (1H, d, J=8.6), 4.17 (1H, dd), 3.88 (1H, t), 3.72 (1H, m), 3.17 (3H, s), 2.58 (1H, d), 2.05 (4H, q, J=7.3 Hz), 1.03 (9H, s), 0.62 (6H, t, J=7.3 Hz).

FAB(+) MS m/z [M]: 468.3; calc. m/z 468.1737.

Example 52

Preparation of 3'-[3-chloro-4-(2-Oxo-3.3-dimethylbutoxy)]-3'-(4-trifluoromethylsulfonyloxyphenyl)pentane

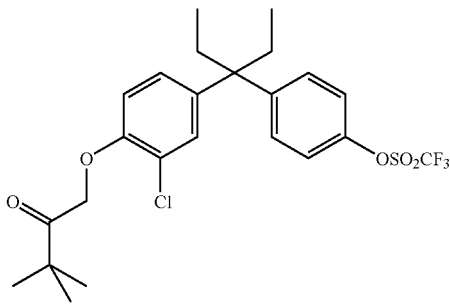

To 3'-[3-chloro-4-(2-oxo-3.3-dimethylbutoxy)phenyl]-3'-(4-hydroxyphenyl)pentane. (4.00 g, 10.3 mmol) and diisopropylethylamine (1.40 g, 1.88 mL, 10.8 mmol) in 160 mL of methylene chloride is added by syringe trifluoromethanesulfonic anhydride (3.05 g, 1.82 mL, 10.8 mmol) at RT. After stirring the mixture for 16 h, the resulting brown solution is poured over pH=7.00 potassium phosphate monobasic/sodium hydroxide buffer (150 mL) and ice (150 g). The organic layer is separated and washed with additional buffer (2×150 mL), dried over anhydrous magnesium sulfate, and concentrated to an almost colorless viscous oil (5.2 g). The oil was purified by chromatography over silica gel with a gradient of 25% to 75% of chloroform-hexane. Appropriate fractions are combined and concentrated to provide the title compound as a clear, colorless oil (3.7 g, 69%).

H-NMR (300 mHz, DMSO-D6): δ 7.40 (2H, d, J=8.7 Hz), 7.33 (2H, d, J=8.7 Hz), 7.15 (1H, d, J=2.1 Hz), 6.68 (1H, dd, J=2.1 Hz, J=8.6 Hz), 6.78 (2H, d, J=8.6 Hz), 5.22 (2H, s), 2.07 (4H, q, J=7.3 Hz), 1.17 (9H, s), 0.62 (6H, t, J=7.3 Hz).

FAB+MS: 521.0 (M+H); calc. 521.1376 (M+H).

ES MS: 521.3 (M+1), 538.3 (M+NH4), 543.2 (M+Na)

Example 53

Preparation of racemic 3'-[3-chloro-4-(2-hydroxy-3.3-dimethylbutoxy)phenyl]-3'-(4-trifluoromethylsulfonyloxyphenyl)pentane

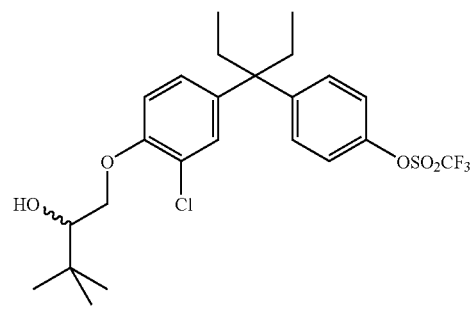

To 3'-[3-chloro-4-(2-oxo-3.3-dimethylbutoxy)phenyl]-3'-(4-trifluoromethylsulfonyloxyphenyl)pentane (500 mg, 0.96 mmol) in 40 mL of MeOH at 0° C. is added sodium borohydride (38 mg, 1.0 mmol). After 30 min at 0° C. the excess reagent is destroyed by the addition of acetone (1 mL.) and pH=7.00 potassium phosphate monobasic/sodium hydroxide buffer (10 mL). The resulting mixture is concentrated to near dryness under reduced pressure and the residue is distributed between methylene chloride (20 mL) and water (20 mL). The organic layer is separated and the aqueous layer is extracted with additional methylene chloride (10 mL). The combined organic extracts are dried over anhydrous magnesium sulfate and concentrated to a colorless oil which is the title compound (495 mg, 99%).

H-NMR (300 mHz, CDCl3): δ7.21 (2H, d, J=8.8 Hz), 7.16 (2H, d, J=8.8 Hz), 6.97 (1H, dd, J=2.3 Hz, J=8.6 Hz), 6.84 (1H, d, J=8.6 Hz), 4.18 (1H, dd, J=2.6 Hz, J=9.0 Hz), 3.89 (t, J=8.9 Hz,), 3.73 (1H, dt, J=2.6, J=8.9, J=3.0), 2.57, (1H, d, J=3.0 Hz), 2.06 (4H, q, J=7.3 Hz), 1.04 (9H, s), 0.62 (6H, t, J=7.3 Hz).

FAB(+) MS m/z [M]: 522.1; calc. 522.1455.

ES (+) MS m/z: 540.3 (M+NH4); calc 540.1798.

Example 54

Preparation of 3'-[3-chloro-4-(2-oxo-3,3-dimethylbutoxy)phenyl]-3'-[3-methyl-4-(trifluoromethylsulfonyloxy)phenyl]pentane

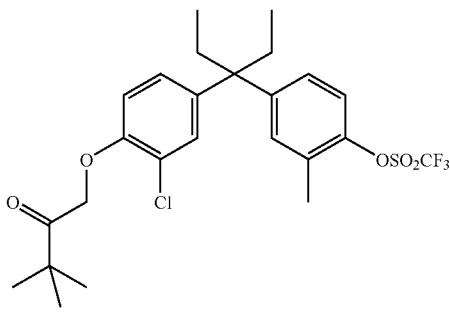

A. [E,Z]-3-[3-Chloro-4-(trifluoromethylsulfonyloxy)phenyl]-3-pentene

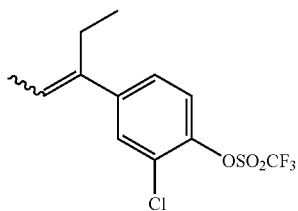

In a procedure analogous to Example 52, [E,Z]-3-(3-chloro-4-hydroxyphenyl)-3-pentene (5.15 g, 26 mmol), trifluoromethanesulfonic anhydride (8.13 g, 28 mmol), and diisopropylethylamine (3.7 g, 5.0 mL, 28 mmol) are reacted in 200 mL of methylene chloride to give the title compound as a brown oil (8.7 g, approx. 100%) which is used without further purification. The [E, Z] olefin isomers are present in a ratio of about 3 to 1, respectively.

H-NMR (300 mHz, CDCl3): δ 7.01-7.40 (3H, m), 5.67 (0.75H, q, J=6.9 Hz), 5.53 (0.25H, q, J=6.9 Hz), 2.41((1.5H, q, J=7.6 Hz), 2.24 (0.5H, q, J=7.6 Hz), 1.84 (2.25H, d, J=7.6 Hz), 1.48 (0.75H, d, J=7.6 Hz), 0.91 (2.25H, t, J=7.6 Hz)), 0.86 (0.75H, t, J=7.6 Hz).

TOF MS EI+:328.015; calc. 328.0226.

In an alternative preparation, a solution of [E,Z]-3-(3-chloro-4-hydroxyphenyl)-3-pentene (9.85 g, 50 mmol), and triethyl amine (5.32 g, 7.29 mL, 52 mmol) in 400 mL of methylene chloride at −35 deg C. is treated slowly with trifluoromethanesulfonic anhydride (8.13 g, 28 mmol) added by syringe, so as to keep the temperature below minus 30° C. The resulting pale yellow solution is stirred for 3 h while it is allowed to warm to RT. The reaction mixture is then poured over pH=7.00 potassium phosphate monobasic/sodium hydroxide buffer (150 mL) and ice (150 g). The organic layer is separated and washed with additional buffer (4×150 mL), dried over anhydrous magnesium sulfate, and concentrated to a pale yellow oil (16.7 g, 98%). Final purification was accomplished by chromatography over silica gel using 10% chloroform in hexane as the eluent. Fractions containing only the title olefins as determined by TLC (silica gel; hexane) are combined to provide 11.7 g (71%) of the purified [E,Z] mixture of olefins in a ratio of 9 to 1, respectively.

H-NMR (300 mHz, CDCl3): δ 7.01-7.40 (3H, m), 5.67 (0.9H, q, J=6.9 Hz), 5.53 (0.1H, q, J=6.9 Hz), 2.41((1.8H, q, J=7.6 Hz), 2.24 (0.2H, q, J=7.6 Hz), 1.84 (2.7H, d, J=7.6 Hz), 1.48 (0.3H, d, J=7.6 Hz), 0.91 (2.7H, t, J=7.6 Hz)), 0.86 (0.3H, t, J=7.6 Hz).

B. 3'-(4-hydroxy-3-methylphenyl)-3'-[3-chloro-4-(methylsulfonyloxy)-phenyl]pentane

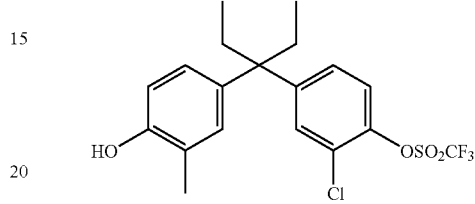

In a procedure analogous to Example 50D, [E,Z]-3-[3-chloro-4-(trifluoromethylsulfonyloxy)phenyl]-3-pentene (8.7 g, 26 mmol) and o-cresol (17.2 g, 159 mmol) in 200 mL methylene chloride are treated at RT with BF3-etherate (1.47 g, 10.4 mmol) and the resulting mixture is stirred for 30 m at ambient temperature. The resulting light reddish brown solution is then worked up by the distillation and extraction procedure analogous to that used in the aforementioned example. The crude product was obtained as a tan oil which is purified by chromatography over silica gel with a gradient of 50% to 60% chloroform in hexane. Fractions that contained the desired product were combined and concentrated to provide the title compound as a pale tan oil (4.29 g, 38%).

H-NMR (300 mHz, CDCl3): 6.5 to 7.3 (6H, m) 4.57 (1H, s), 2.21 (3H, s), 2.05 (4H, q, J=7.3 Hz), 0.62 (6H, t, J=7.3 Hz).

ES(−) MS m/z: 435.1 (M−H); calc. 435.0645.

C. Preparation of 3'-[3-chloro-4-(2-oxo-3,3-dimethylbutoxy)-phenyl]-3'-[3-methyl-4-(trifluoromethylsulfonyloxy)phenyl]pentane Note: (A Triflate Rearrangement Procedure)

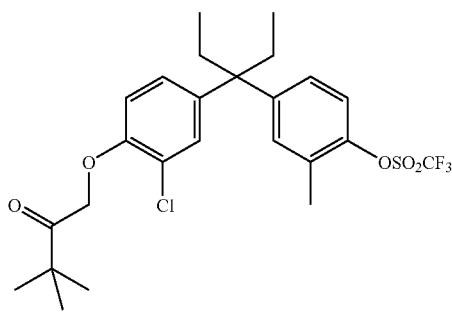

In a procedure analogous to Example 50C, 3'-(3-chloro-4-hydroxyphenyl)-3'-[3-methyl-4-(methylsulfonyloxy)phenyl]pentane(4.00 g, 9.17 mmol), 1-chloropinacolone (1.30 g, 9.62 mmol), anhydrous KI (76 mg, 0.46 mmol), and anhydrous K2CO3 (6.32 g, 45.9 mmol) are reacted in 125 mL acetonitrile. The title product is isolated and purified by silica gel chromatography using a gradient of 30% to 50% chloroform in hexane. Further chromatography of mixed fractions with a hexane to 10% EtOAc gradient provides additional pure compound (total amount 2.61 g, 53%).

H-NMR (300 mHz, CDCl3): δ7.15 (1H, d, J=2.3 Hz), 7.11 (1H, d, J=8.4 Hz), 7.04 (1H, d, J=2.3 Hz), 7.02 (1H, dd, J=2.3 Hz, J=8.4 Hz), 6.89 (1H, dd, J=8.6 Hz, J=2.3 Hz), 6.62 (1H, d, J=8.6 Hz), 4.91 (2H, s), 2.32 (3H, s), 2.03 (4H, q, J=7.2 Hz), 1.26 (9H, s), 0.60 (6H, t, J=7.2 Hz).

ES(+) MS m/z: 552.2 (M+NH4); calc. 552.1798

FAB(+) MS m/z [M]: 534.9; calc. 534.

Further NMR data: COSY data allowed the spin systems of the two aromatic rings to be grouped together. When the OCH2 was selectively excited, a NOE is observed with a resonance at 6.62 δ which is ortho only coupled. When the aromatic methyl (at 2.32 δ) was excited, a NOE is observed to a meta coupled proton at 7.04 δ. These resonances are not part of the same spin system, requiring the OCH2 and aromatic methyl to be on different rings. Therefore the triflate has migtated during the reaction and the isolated product has the structure shown above. (HMBC data also supports this conclusion.)

Example 55

Preparation of racemic 3'-[3-chloro-4-(2-hydroxy-3.3-dimethylbutoxy)phenyl]-3'-[3-methyl-4-(trifluoromethylsulfonyloxy)phenyl]pentane

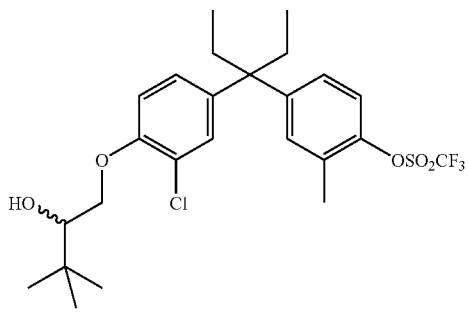

In a procedure analogous to Example 51, 3'-[3-chloro-4-(2-oxo-3,3-dimethylbutoxy)phenyl]-3'-[3-methyl-4-(methylsulfonyloxy)phenyl]pentane (730 mg, 1.36 mmol) in 60 mL of MEOH is reduced by sodium borohydride (76 mg, 2.0 mmol). After 30 min, the mixture is quenched and worked up to provide the crude product which was purified by chromatography over silica gel with a gradient of hexane to 5% EtOAc in hexane to provide the title compound (719 mg, 98%).

H-NMR (300 mHz, CDCl3): δ 7.15 (1H, d, J=2.3 Hz), 7.13 (1H, d, J=8.4 Hz), 7.05 (1H, d, J=2.0 Hz), 7.03 (1H, dd, J=2.3 Hz, J=8.4 Hz), 6.96 (1H, dd, J=8.6 Hz, J=2.3 Hz), 6.86 (1H, d, J=8.6 Hz), 4.20 (1H, dd, J=8.9, 2.5 Hz), 3.906 (1H, t, J=8.9 Hz), 3.75 (1H, dd, J=8.9, 2.5 Hz), 2.59 (1H, br s), 2.34 (3H, s), 2.06 (4H, q, J=7.3 Hz), 1.03 (9H, s), 0.63 (6H, t, J=7.3 Hz).

ES(+) MS m/z: 554.2 (M+NH4); calc. 554.1954.

FAB(+) MS m/z [M]: 536.1; calc. 536.1661

Compounds of the Invention—Salts, Stereoisomers, & Prodrugs:

Salts of the compounds represented by formulae I are an additional aspect of the invention. The skilled artisan will also appreciate that the family of compounds of formulae I include acidic and basic members and that the present invention includes pharmaceutically acceptable salts thereof.

In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, ammonium, calcium, magnesium, aluminum, zinc, and the like. Sodium and potassium saltgs are particularly preferred. Salts are conveniently prepared from the free acid by treating the acid in solution with a base or by exposing the acid to an ion exchange resin. For example, a carboxylic acid substituent on the compound of Formula I may be selected as —CO2H and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, choline, clavulanate, citrate, chloride, chloroprocaine, choline, diethanolamine, dihydrochloride, diphosphate, edetate, edisylate, estolate, esylate, ethylenediamine, fluoride, fumarate, gluceptate, gluconate, glutamate, glycolylarsanilate, hexylresorcinate, hydrabamine, bromide, chloride, hydrobromide, hydrochloride, hydroxynaphthoate, iodide, isothionate, lactate, lactobionate, laurate, malate, maleate, malseate, mandelate, meglumine, mesylate, mesviate, methylbromide, methylnitrate, methylsulfate, mucate, napsylate, nitrate, oleate, oxalate, palmitate, pamoate, pantothenate, phosphate, polygalacturonate, procane, salicylate, stearate, subacetate, succinate, sulfate, tannate, tartrate, teoclate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a chiral column may be used such as those sold by Daicel Chemical Industries identified by the trademarks:

CHIRALPAK AD, CHIRALPAK AS, CHIRALPAK OD, CHIRALPAK OJ, CHIRALPAK OA, CHIRALPAK OB, CHIRALPAK OC, CHIRALPAK OF, CHIRALPAK OG, CHIRALPAK OK, and

CHIRALPAK CA-1.

By another conventional method, a racemic mixture may be reacted with a single enantiomer of some other compound. This changes the racemic form into a mixture of diastereomers. These diastereomers, because they have different melting points, different boiling points, and different solubilities can be separated by conventional means, such as crystallization.

The present invention is also embodied in mixtures of compounds of formulae I.

Prodrugs are derivatives of the compounds of the invention which have chemically or metabolically cleavable groups and become by solvolysis or under physiological conditions the compounds of the invention which are pharmaceutically active in vivo.

Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs, pp.* 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters to use as prodrugs are; methyl, ethyl, propyl, isopropyl, n-butyl, isobutyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula I (in a medium such as dimethylformamide) 4-(2-chloroethyl)morpholine hydrochloride (available from Aldrich Chemical Co., Milwaukee, Wis. USA, Item No. C5,220-3). For example, prodrugs may be prepared by reaction of the sodium salt for a compound of Formula I with;

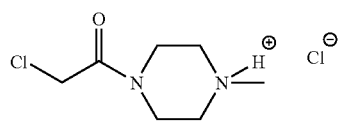

and sodium iodide to provide tthe ester prodrug pendent group

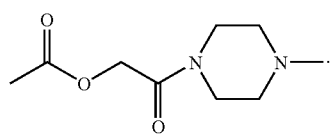

Also, lower alkyl (viz., $C_1$-$C_8$) ester prodrugs may be prepared by conventional means such as reacting the sodium or potassium salt (derived by forming the salt of any acidic compound of the invention; viz., reaction of a base such as KOH with an acidic group such as —$CO_2H$) of a compound of Formula I with an alkyl iodide such as methyl iodide, ethyl iodide, n-propyl iodide, isopropyl iodide. Typical ester prodrug substituents are

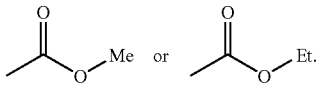

Pharmaceutical Formulations Containing the Novel Compounds of the Invention:

Pharmaceutical formulations of the invention are prepared by combining (e.g., mixing) a therapeutically effective amount of the compound of the invention (compounds of Formula I) together with a pharmaceutically acceptable carrier or diluent. The present pharmaceutical formulations are prepared by known procedures using well-known and readily available ingredients.

In making the compositions of the present invention, the compounds of Formula I will usually be admixed with a carrier, or diluted by a carrier, or enclosed within a carrier which may be in the form of a capsule, sachet, paper or other container.

When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the compound. The compounds of the present invention are preferably formulated prior to administration.

The compounds of the invention may also be delivered by suitable formulations contained in a transderm patch. Alternatively, the compounds of the invention may be delived to a patient by sublingual administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the compound of Formula I is mixed with a carrier having the necessary binding properties in suitable proportions and compacted in the shape and size desired. The powders and tablets preferably contain from about 1 to about 99 weight percent of the compound which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active Ingredient may be dissolved or suspended in a pharmaceutically acceptable carrier, such as sterile water, sterile organic solvent or a mixture of both. The compounds can often be dissolved in a suitable organic solvent, for instance aqueous propylene glycol. Other compositions can be made by dispersing the finely divided compounds of the invention in aqueous starch or sodium carboxymethyl cellulose solution or in a suitable oil.

Methods of Using the Compounds of the Invention:

Many disease states are benefited by treatment with the compounds of Formula I include, but are not limited to:
- disease states characterized by abnormal calcium regulation
- disease states characterized by abnormal cell proliferation
- disease states characterized by abnormal cell differentiation
- disease states characterized by abnormal immune response
- disease states characterized by abnormal dermatological conditions
- disease states characterized by neurodegenerative condition
- disease states characterized by inflammation
- disease states characterized by vitamin D sensitivity
- disease states characterized by hyperproliferative disorders.

Specific disease states benefited by treatment of the compounds of Formula I and II include, but are not limited to:
- Acne
- Actinic keratosis
- Alopecia
- Alzheimer's disease
- Benign prostatic hyperplasia
- Bladder cancer
- Bone maintenance in zero gravity
- Bone fracture healing
- Breast cancer
- Chemoprovention of Cancer
- Crohn's disease
- Colon cancer
- Type I diabetes
- Host-graft rejection
- Hypercalcemia
- Type II diabetes
- Leukemia
- Multiple sclerosis
- Myelodysplastic syndrome
- Insufficient sebum secretion
- Osteomalacia
- Osteoporosis
- Insufficient dermal firmness
- Insufficient dermal hydration
- Psoriatic arthritis
- Prostate cancer
- Psoriasis
- Renal osteodystrophy
- Rheumatoid arhritis
- Scleroderma
- Skin cancer
- Systemic lupus erythematosus
- Skin cell damage from Mustard vesicants
- Ulcerative colitis
- Vitiligo
- Wrinkles Particularly preferred is the treatment of psoriasis and osteoporosis by administration to a mammal (including a human) of a therapeutically effective amount of compounds of Formulae I. By "pharmaceutically effective amount" it is meant that quantity of pharmaceutical agent corresponding to formulae I which prevents, removes or reduces the deleterious effects of a disease state in mammals, including humans.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a pharmaceutically effective amount typically in the range of from about 0.0001 mg/kg/day to about 50 mg/kg/day of body weight of an active compound of this invention. Preferably the dose of compounds of the invention will be from 0.0001 to 5 mg/kg/day of body weight.

Preferably compounds of the invention (e.g., per Formula I) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.0001 to about 1000 milligrams or more according to the particular treatment involved. It may be appreciated that it is necessary to make routine variations to the dosage depending on the age and condition of the patient. Dosage will also depend on the route of administration. The compounds of the invention may be administered by a variety of routes including oral, aerosol, rectal, transdermal, sublingual, subcutaneous, intravenous, intramuscular, and intranasal. Particularly preferred is the treatment of psoriasis with an ointment type formulation containing the compounds of the invention. The ointment formulation may be applied as needed, typically from one to 6 times daily.

Treatment of psoriasis is preferably done with topical application by a formulation in the form of a cream, oil, emulsion, paste or ointment containing a therapeutically effective amount of a compound of the invention. The formulation for topical treatment contains from 0.5 to 0.00005 weight percent, preferably from 0.05 to 0.0005 weight percent, and most preferably from 0.025 to 0.001 of a Active Ingredient.

For example, two semisolid topical preparations useful as vehicles for VDR modulators in treatment and prevention of psoriasis are as follows:

Polyethylene Glycol Ointment USP (p. 2495)

Prepare Polyethylene Glycol Ointment as follows:

| | |
|---|---|
| Polyethylene Glycol 3350 | 400 g. |
| Polyethylene Glycol 400 | 600 g. |
| To make | 1000 g. |

Heat the two ingredients on a water bath to 65 C. Allow to cool, and stir until congealed. If a firmer preparation is desired, replace up to 100 g of the polyethylene glycol 400 with an equal amount of polyethylene glycol 3350.

Hydrophilic Ointment USP (p. 1216)

Prepare Hydrophilic Ointment as follows:

| | |
|---|---|
| Methylparaben | 0.25 g. |
| Propylparaben | 0.15 g. |
| Sodium Lauryl Sulfate | 10 g. |
| Propylene Glycol | 120 g. |
| Stearyl Alcohol | 250 g. |

-continued

| | |
|---|---|
| White Petrolatum | 250 g. |
| Purified Water | 370 g. |
| To make about | 1000 g. |

The Stearyl Alcohol and White Petrolatum are melted on a steam bath, and warmed to about 75 C. The other ingredients, previously dissolved in the water are added, warmed to 75 C, and the mixture stirred until it congeals.

For each of the above formulations the Active Ingredient is added during the heating step in an amount that is from 0.5 to 0.00005 weight percent, preferably from 0.05 to 0.0005 weight percent, and most preferably from 0.025 to 0.001 weight percent of the total ointment weight. (Source:— United States Pharmacopoeia 24, United States Pharmacopeial Convention, 1999)

Conventional therapy for osteoporosis includes; (i) estrogens, (ii) androgens, (iii) calcium supplements, (iv) vitamin D metabolites, (v) thiazide diuretics, (vi) calcitonin, (vii) bisphosphonates, (viii) SERMS, and (ix) fluorides (see, Harrison's Principles of Internal Medicine, 13$^{th}$ edition, 1994, published by McGraw Hill Publ., ISBN 0-07-0323704, pgs. 2172-77; the disclosure of which is incorporated herein by reference.). Any one or combination of these conventional therapies may be used in combination with the method of treatment using compounds of Formulae I as taught herein. For example, in a method of treating osteoporosis, the vitamin D receptor modulator compounds of the invention (e.g., as defined by formula I) may be administered separately or simultaneously with a conventional therapy. Alternatively, the vitamin D receptor modulator compounds of the invention may be combined with conventional therapeutic agents in a formulation for treatment of osteoporosis such as set out below:

A formulation for treating osteoporosis comprising:
Ingredient (A1): a vitamin D receptor modulator represented by formula (I), or a pharmaceutically acceptable salt or prodrug derivative thereof;
Ingredient (B1):
one or more co-agents that are conventional for treatment osteoporosis selected from the group consisting of:
a. estrogens,
b. androgens,
c. calcium supplements,
d. vitamin D metabolites,
e. thiazide diuretics,
f. calcitonin,
g. bisphosphonates,
h. SERMS, and
i. fluorides.
Ingredient (C1): optionally, a carrier or diluent.

Typically useful formulations are those wherein the weight ratio of (A1) to (B1) is from 10:1 to 1:1000 and preferably from 1:1 to 1:100.

Combination Therapy for Psoriasis:
Conventional therapy for psoriasis includes topical glucocorticoids, salicylic acid, crude coal tar, ultraviolet light, and methotrexate (see, Harrison's Principles of Internal Medicine, 13$^{th}$ edition, 1994, published by McGraw Hill Publ., ISBN 0-07-0323704, pgs. 2172-77). Any one or combination of these conventional therapies may be used in combination with the method of treatment using compounds of Formulae I as taught herein. For example, in a method of treating osteoporosis, the vitamin D receptor modulator compounds of the invention (e.g., as defined by formula I) may be topically administered separately or simultaneously with a conventional therapy. Alternatively, the vitamin D receptor modulator compounds of the invention may be combined with conventional therapeutic agents in a topically applied formulation for treatment of osteoporosis such as set out below:

A formulation for treating psoriasis comprising:
Ingredient (A2): a vitamin D receptor modulator represented by formula (I), or a pharmaceutically acceptable salt or prodrug derivative thereof;
Ingredient (B2):
one or more co-agents that are conventional for treatment psoriasis selected from the group consisting of:
a. topical glucocorticoids,
b. salicylic acid, or
c. crude coal tar.
Ingredient (C2): optionally, a carrier or diluent.

Typically useful formulations are those wherein the weight ratio of (A2) to (B2) is from 1:10 to 1:100000 and preferably from 1:100 to 1:10000.

Assays and Test Results:

TABLE 3

Summary of Experimental Results

| Test Cmpd.[1] | RXR-VDR heterodimer[2] EC$_{50}$ (nM) | VDR EC$_{50}$ (nM) (Caco-2 cells)[3] | OCN Promoter[4] EC$_{50}$ (nM) | Mouse Hypercal[5] µg/Kg/d |
|---|---|---|---|---|
| Ex. 1 | 3.41 | 117.81 | 2.72 | |
| Ex. 2 | | 46.5 | 5.1 | 50 |
| Ex. 3 | | 133 | 16.3 | 50 |
| Ex. 4 | | 164 | 0.91 | |
| Ex. 5 | | 1594.5 | 20.75 | >500 |
| Ex. 6 | | 1138 | 11.3 | 300 |
| Ex. 7 | | 331 | 84 | 100 |
| Ex. 8 | | 34.75 | 3.48 | |
| Ex. 9 | | 13 | | |
| Ex. 10 | | 15 | 0.3 | |
| Ex. 12 | | 112 | 2.325 | |
| Ex. 14 | | 89 | 9.77 | <300 |
| Ex. 17 | | | 3.75 | |
| Ex. 18 | 69.56 | 485.21 | 7.625 | 1500 |
| Ex. 19 | | | 16.75 | |
| Ex. 20 | | | 28.1 | 500 |
| Ex. 21 | | | 124.5 | |
| Ex. 22 | | | 29.8 | 500 |
| Ex. 23 | 0.817 | 6.0645 | 0.33 | 500 |
| Ex. 24 | | | 44.65 | <1000 |
| Ex. 25 | 47.26 | 1285.266 | 34.25 | |
| Ex. 26 | 5.697 | 333.00 | 3.685 | <1000 |
| Ex. 27 | | | 10.59 | 500 |
| Ex. 28 | | | 17.9 | 1000 |
| Ex. 29 | | | 4.585 | 100 |
| Ex. 30 | | | 103.8 | |
| Ex. 31 | | | 44 | |
| Ex. 32 | | | 239.57 | |
| Ex. 33 | | | 49.37 | |
| Ex. 34 | | | 373.53 | |
| Ex. 35 | 137.92 | 615.60 | 20.1 | |
| Ex. 36 2044283 | 15.226 | 592.38 | 45.5 | >3000 |
| Ex. 37 | | 308.25 | 67.23 | |
| Ex. 38 | | | 2.085 | <300 |
| Ex. 39 | | 18 | 1.79 | <100 |
| Ex. 40 | | 374.5 | 1.905 | 300 |
| Ex. 41 | | 614 | 111.4 | |
| Ex. 42 | 495.3014 | 728.4 | 25.15 | <1000 |
| Ex. 43, 51 | | | 7.525 | |
| Ex. 44 | 2.208 | 86.604 | 2.4 | |

TABLE 3-continued

Summary of Experimental Results

| Test Cmpd.[1] | RXR-VDR heterodimer[2] $EC_{50}$ (nM) | VDR $EC_{50}$ (nM) (Caco-2 cells)[3] | OCN Promoter[4] $EC_{50}$ (nM) | Mouse Hypercal[5] µg/Kg/d |
|---|---|---|---|---|
| Ex. 45, 51B | 24.00 | 353.18 | 13 | |
| Ex. 48 | | | 54.1 | <1000 |
| Ex 46, 52 | | | 217.1 | |
| Ex. 47, 53 | 12.53 | 430.90 | 92.45 | |
| AA | 12 | 16 | 5 | 0.06 |
| BB | | 225 | 11 | 20 |
| CC | | 710000 | 10000 | >30000 |

TABLE 4

Summary of Experimental Results

| Test Cmpd.[1] | Kera. Prolif. $IC_{50}$ (nM) | IL-10 $IC_{50}$ (nM) |
|---|---|---|
| Ex. 14 | 2 | |
| Ex. 17 | 2 | |
| Ex. 18 | 32 | |
| Ex. 21 | 67 | |
| Ex. 25 | 14.55 | |
| Ex. 26 | 4.4 | |
| Ex. 36 | 36 | |
| Ex. 42 | 9 | |
| Ex. 43, 51 | 4 | |
| Ex. 45, 51B | 27 | 39.5087 |
| Ex 46, 52 | 90 | |
| Ex. 47, 53 | 300 | |
| Ex. 48 | 13 | |
| AE | 18 | |

Explanation of Table 3 and 4 Column Numerical Superscripts:

1. Test Compound coded with Example numbers correspond to the products of the same numbered example in the specification. Alphbetical symbols (e.g., "AA", "BZ") correspond to the chemical species identified by the same symbol in the specificaton.

"AA"=1α,25-dihydroxyvitamin $D_3$

"BB"=3-(4-{1-Ethyl-1-[4-(2-hydroxy-3,3-dimethyl-butoxy)-3-methyl-phenyl]-propyl}-2-methyl-phenoxy)-propane-1,2-diol "CC"=1-(4-{1-[4-(3,3-Dimethyl-2-oxo-butoxy)-3-methyl-phenyl]-cyclohexyl}-2-methyl-phenoxy)-3,3-dimethyl-butan-2-one "DD"=compound represented by the formula:

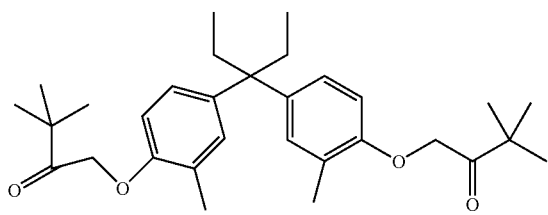

"EE"=compound represented by the formula:

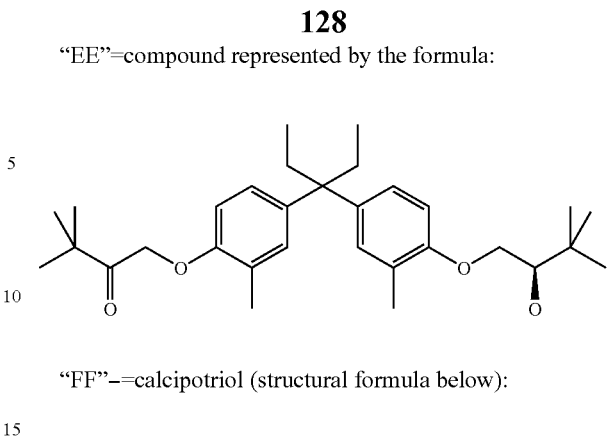

"FF"-=calcipotriol (structural formula below):

2. The RXR-VDR heterodimerization (SaOS-2 cells) test is described in the "Assay" section of the Description, infra.

3. The VDR CTF (Caco-2 cells) test is described in the "Assay" section of the Description, infra.

4. The OCN Promoter test is described in the "Assay" section of the Description, infra.

5. The Mouse Hypercalcemia test is described in the "Assay" section of the Description, infra.

6. The keratinocyte proliferation assay is described in the "Assay" section of the Description, infra.

7. The IL-10 induction assay is described in the "Assay" section of the Description, infra.

Assay Methods

Use of the Assay Methods:

The evaluation of the novel compounds of the invention for osteoporosis and other related diseases is done using a plurality of test results. The use of multiple assays is necessary since the combined properties of (i) high activity for the vitamin D receptor, and (ii) prevention of hypercalcemia must be achieved to have utility for the methods of treating diseases, which are also, aspects of this invention. Some of the tests described below are believed related to other tests and measure related properties of compounds. Consequently, a compound may be considered to have utility in the practice of the invention if is meets most, if not all, of the acceptance criteria for the above described tests.

The evaluation of the novel compounds of the invention for psoriasis is done using the Keratinocyte Proliferation Assay in combination with other assays that measure inhibition of UL-2 production and stimulation of IL-10 production in peripheral blood mononuclear cells (PBMCs).

Brief Description, Utility and Acceptance Criteria for the Assay Methods:

1. The RXR-VDR heterodimer Assay:

This assay provides the VDR activity of a test compound. It is desirable to have low EC50 values for a compound in this assay. The lower the EC50 value, the more active the compound will be as a VDR agonist. Desired assay results are EC50 values less than or equal to 600 nM. Preferred assay results are less than 250 nM, and most preferably less than 150 nM.

2. The Caco-2 Cell Co-Transfection Assay:

The Caco-2 cell assay is an indicator for the undesirable condition of hypercalcemia. This co-transfection assay is a surrogate assay for in vivo calcemic activity of VDR ligands. It is desirable to have high EC50 values for a test compound in this assay. The higher the EC50 values for a compound the less calcemic it will be in vivo. Desired assay results are EC50 greater than or equal to 300 nM. Preferred assay results are greater than 1000 nM.

3. The OCN (osteocalcin) Promoter Assay

The OCN Promoter Assay is an indicator and marker for osteoporosis. Desired assay results are EC50 less than or equal to 325 nM. Preferred assay results are less than 50 nM.

4. The Mouse Hypercalcemia Assay

The Mouse Hypercalcemia Assay is a six day hypercalcemia test for toxicity and selectivity. Acceptable test results are levels greater than 300 µg/kg/day. Preferred assay results are levels greater than 1000 µg/day.

5. The Keratinocte Proliferation Assay

This Assay is indicative for the treatment of psoriasis. An acceptable test result is IC50 value of less than or equal to 300 nM. Preferred assay results are IC50 values of less than 100 nM.

6. The IL-10 induction Assay

This is an in vitro efficacy assay for psoriasis, abscess and adhesion. Psoriasis involves both keratinocytes and immune cells. IL-10 is a unique cytokine because it is anti-inflammatory and immunosuppressive. This assay tells us whether a VDRM is able to function as an agonist in PBMCs (primary blood mononuclear cells) or not. A lower EC50 value is desirable in this assay since a compound with a lower EC50 value will be a better agonist in PBMCs. An acceptable test result is an EC50 value of less than 200 nM. Preferred assay results are EC50 values of less than 100 nM.

7. Other Compound Assay Standards

An alternative measusre of the efficacy of compounds of the invention for treatment of osteoporosis is a numerical ratio calculated as follows:

Dose Threshold needed to induce hypercalcemia divided by Dose Threshold needed for bone efficacy An alternative measusre of the efficacy of compounds of the invention for treatment of psoriasis is a numerical ratio calculated as follows:

Dose Threshold needed to induce hypercalcemia divided by Dose Threshold needed to induce keratinocyte proliferation For the above ratios, Dose Thresholds are determined from dose response curve data.

8. The CaT1 (Calcium Transport Protein 1) Assay

The CaT1 Assay is an indicator for the undesirable condition of hypercalcemia. The higher the EC50 values for a compound the less calcemic it will be in vivo. Desired assay results are EC50 greater than or equal to 500 nM. Preferred assay results are greater than 1000 nM.

Details of the Assay Methods:

(1) Materials and Method for RXR-VDR Heterodimerization Assay:

Transfection Method:
  FuGENE 6 Transfection Reagent (Roche Cat # 1 814 443)

Growth Media:
  D-MEM High Glucose (Gibco BRL Cat # 11054-020), 10% FBS, 1% antibiotic-antimycotic (Ab-Am)

FBS heat inactivated (Gibco BRL Cat # 10092-147)

Ab-Am (Gibco BRL Cat # 15240-062)

Cells:
  Grow SaOs-2 cells in T-152 $cm^2$ culture flasks in growth media.
  Keep the density at $5\text{-}6\times10^5$ cells/ml
  Passage cells 1:3 twice a week
  Add Trypsin EDTA (Gibco BRL Cat # 25300-020) and incubate
  Resuspend cells in plating media and transfer into growth media.

Wash Media:
  HBSS Low Glucose Without Phenol Red (Gibco BRL Cat # 14175-095), 1% Ab-Am Plating Media:
  D-MEM Low Glucose Without Phenol Red (Gibco BRL Cat # 11054-020), 1% Ab-Am

D-MEM

Stripped FBS (Hyclone Cat# SH30068.03 Lot # AHM9371)

Ab-Am

Transfection/Treatment Media:
  D-MEM Low Glucose Without Phenol Red only

T-152 $cm^2$ Culture Flask:
  Use Corning Coastar T-152 $cm^2$ culture flask (Cat # 430825) to grow the cells Flatwell Plates:
  Use well plate to plate cells
  Use Deep well plate sterile to make up treatment media.

Luciferase Assay Reagent:
  Use Steady-Glo Luciferase Reagent from Promega (Cat # E2550) Consists of:
  a. E2533 Assay Substrate, lyophilized product and
  b. E2543 Assay Buffer.
  Thaw at room temperature
  Store Day 1: Cell Plating:

Cell Harvesting

Aspirate media from culture flask, rinse cells with HBSS and aspirate.

Add trypsin and incubate.

When cells appear detached, resuspend cells in growth media.

Transfer into a new flask with fresh growth media for passaging the cells.

Plate well plates and two extra plates

A. Cell Count

Mix the cell suspension using pipette

Use Hematocytometer to count the cells

Load cell suspension onto the hemocytometer chamber

Count cells.

Plate seeding:

Use plating media 10% Stripped FBS in D-MEM Low Glucose, Without Phenol Red, 1%

Ab-Am

Plate 14 plates @ 165 μl/well.

In sterile flask add cell suspension to plating media.

Mix.

Add cells/well.

Place the cells in the incubator.

Cells should be about 75% confluent prior to transfection.

Step 1: DNA and Media

Add plain DMEM media to tubes for mixing the DNA

Add the Reporter gene pFR-LUC

Add the Gal4-RXR-DEF and VP16-VDR-LBD

Step 2: FuGENE and Media

Prepare plain DMEM media in a ubes for mixing FuGENE

Add FuGENE 6 Transfection Reagent

Incubate

Step 3: FuGENE, DNA and Media Complex

Add FuGENE Media complex from step 2 to DNA Media complex from step 1

Incubate

Step 4: FuGENE, DNA and Media Complex to-well plate

Add FuGENE-DNA-Media complex from step 3 to each plate

Incubate.

Day 3: Dosing

Treatment Preparation

Allow for transfection time

Make a stock solution of the compounds in DMSO

Vortex until all the compounds has been dissolved.

Further dilute in D-MEM (Low Glucose—With out Phenol Red)

Add compounds in quadruplicate to give final volume

Incubate.

Day 4: Luciferase Assay

Read the plates after drug treatment

Remove part of media from all the wells and leave remainder

Add Steady-Glo Luciferase Reagent mixture/wells

Incubate

Count each well using a Luminescence counter, Top Count NXT by Packard

Set a delay between plates to reduce the background.

(2) Materials and Method for The Caco-2 Cell Assay:

Caco-2 cells, grown in phenol red free, DMEM (Invitrogen, Carlsbad, Calif.) containing 10% charcoal-stripped FCS (Hyclone, Logan, Utah), were transfected with Fugene 6 reagent (Roche Diagnostics, Indianapolis, Ind.). Cells (5000/well) were plated 18 h before transfection in a 96 well plate. The Cells were transfected with Gal4-responsive reporter pFRLuc (150 ng, Stratagene, La Jolla Calif.) and the receptor expression vector pGal4-VDR-LBD (10 ng), along with Fugene 6 reagent (0.2 μl/well). The DNA-Fugene complex was formed by incubating the mixture for 30 min at room temperature. The cells were transfected in triplicate for 5 h, and treated with various concentrations of VDR ligands (form 0.01 nM to 10,000 nM concentration range) 18 h post-transfection. The luciferase activity was quantified using Steady-Glo reagent kit (Promega, Madison, Wis.) as per manufacturer's specifications.

(3) Materials and Method for the OCN Promoter Assay:

The activation of osteocalcin by VDR ligands was evaluated in a rat osteoblast-like cell line RG-15 (ROS 17/2.8) stably expressing rat osteocalcin promoter fused with luciferase reporter gene. The stable cell lines were established as reported before (Activation of Osteocalcin Transcription involves interaction of protein kinase A- and Protein kinase C-dependent pathways. Boguslawski, G., Hale, L. V., Yu, X.-P., Miles, R. R., Onyia, J. E., Santerre R. F., Chandrasekhar, S. J. Biol. Chem. 275, 999-1006, 2000). Confluent RG-15 cells maintained in DMEM/F-12 medium (3:1) containing 5% FBS, 300 μg/ml G418 and at 37° C. under 5% $CO_2$/95% air atmosphere were trypsinized (0.25% trypsin) and plated into white opaque 96-well cell culture plates (25000 cells/well). After 24 hr, cells (in DMEM/F-12 medium+2% FBS) were treated with various concentrations of compounds, dissolved in DMSO. The final DMSO concentration remained at 0.01% (v/v). After 48 hr treatment, the medium was removed, cells were lysed with 50 μl of lysis buffer (From Luciferase reporter assay system, Roche Diagnostics, Indianapolis, Ind.) and assayed for luciferase activity using the Luciferase Reporter Gene Assay kit from Boehringer Mannheim as per manufacturer's specifications.

(4) Materials and Method for the Mouse Hypercalcemia Assay:

Weanling, virus—antibody-free, five to six weeks old female DBF mice (Harlan, Indianapolis, Ind.) are used for all the studies. Animals are allowed to acclimate to local vivarium conditions for 2 days. Mice are maintained on a 12 hr light/dark cycle at 22° C. with ad lib access to food (TD 5001 with 1.2% Ca and 0.9% P, Teklad, Madison, Wis.) and water. The animals then are divided into groups with 4-5 mice per group. Different doses of test compounds prepared in 10% Ethanol and 90% sesame oil are administered to mice orally via gavage for 6 days. $1\alpha\text{-}25(OH)_2D_3$ 0.5 µg/kg/d was also given to one group of mice as the positive control. Serum ionized calcium is evaluated at 6 hours after the last dosing under isoflurane anesthesia by Ciba-Corning Ca++/PH Analyzer, (Model 634, Chiron Diagnostics Corp., East Walpole, Mass.). Raw data of group differences is assessed by analysis of variance (ANOVA) using Fisher's protected least significant difference (PLSD) where the significance level was $P<0.05$.

(5) The Keratinocyte Proliferation Assay:

KERtr cells (Human skin keratinocyte transformed with a retrovirus vector, obtained from ATCC) were plated in 96-well flat-bottomed plates (3000 cells/well) in 100 □l keratinocyte serum free medium supplemented with bovine pituitary extract in the absence of EGF (Life Technologies, Rockville, Md.) and incubated at 37° C. for two days. The cells were treated with various concentrations of VDR ligands (ten-fold serial dilution from 10,000 nM to 0.1 nM in triplicate), dissolved in 100 µl keratinocyte serum free medium supplemented with bovine pituitary extract in the absence of EGF and incubated at 37° C. for 72 hr. BrdU (5-bromo-2'-deoxyuridine) incorporation was analyzed as a measure of DNA replication (Cell proliferation ELISA kit, Roche Diagnostics, Indianapolis, Ind.) and absorbance was measured at 405 nm. Potency values ($IC_{50}$) values were determined as the concentration (nM) of compound that elicited a half-maximal response.

(6) Materials and Method for Human IL-10 Induction Assay:

Isolation of Peripheral Blood Mononuclear Cells (PBMCs):
A. Collect 50 ml of human blood and dilute with media, RPMI-1640.
B. Prepare sterile tubes with ficol.
C. Add diluted blood to tubes.
D. Centrifuge.
E. Discard the top layer and collect the cells from middle layer.
F. Divide all cells into four tubes and add media.
G. Centrifuge.
H. Aspirate off media and resuspend.
I. Collect all cells
J. Centrifuge. at 1200 rpm for 10 minutes.
K. Resuspend in RPMI-1640 with 2% FBS and count cells
Stimulation of PBMC:
L. Prepare TPA in DMSO.
M. Dissolve PHA in water.
N. Plate TPA/PHA treated PBMCs in well plates.
O. Incubate.
Treatment:
P. Prepare all compound dilutions in plain RPMI-1640 media.
Q. Add diluted compound.
R. Incubate.
Sample Collection and Assay:
S. Remove all the cells by centrifugation and assay the supernatant for IL-10 by immunoassay.
1) T. Perform IL-10 assay using anti-human IL-10 antibody coated beads, as described by the manufacturer (Linco Research Inc., St. Charles, Mo.).

(8) Materials and Methods for CaT-1 Assay:

Human colon carcinoma, Caco-2 cells, maintained in DMEM (high glucose with 25 mM Hepes buffer; Invitrogen, Carlsbad, Calif.) supplemented with 10% fetal bovine serum (Invitrogen, Carlsbad, Calif.), are plated at 5500 cell per well in a 96-well plate in a total volume of 100 µl/well. The cells are kept in the 96-well plate for 6 days to differentiate them to small intestinal cells that express the calcium transporter, CaT1. On day 3 after plating, old media is removed and replaced with fresh media (150 µl/well). On day 6 the old media is removed and the cells are kept in treatment media (180 µl/well) that contained 10% charcoal stripped fetal bovine serum (Hyclone, Logan, Utah) in DMEM (low glucose, without phenol red; Invitrogen, Carlsbad, Calif.). The cells are treated with various concentrations of VDR ligands (from 0.01 nM to 10,000 nM concentration range) prepared in treatment media (20 µl/well). Twenty hours post-treatment, total RNA is prepared by RNeasy 96 method as described by the manufacturer (Qiagen, Valencia, Calif.). The RNA is reverse transcribed and amplified for human CaT1 and GAPDH (control) messages by quantitative RT-PCR using ABI PRISM 7900HT Sequence Detection System according to manufacturer's instructions (Applied Biosystems, Foster City, Calif.). Optimized primer pairs and probes for human CaT1 and GAPDH genes are obtained commercially (Applied Biosystems, Foster City, Calif.). Each 20 µl quantitative RT-PCR reaction in a 384-well Taqman PCR plate consists of forward and reverse primers (900 nM), Taqman probe (200 nM), total RNA (4 µl form each well of the 96-well culture plate) and 10 µl of Taqman Universal PCR Master Mix (Roche Diagnostics, Indianapolis, Ind.). Reactions are incubated at 48° C. for 30 minutes, followed by 10 minutes at 95° C. and subjected to 40 cycles of PCR (95° C. for 15 seconds followed by 60° C. for 1 minute). GAPDH is used as an internal control and its primer and probe set are obtained commercially (Applied Biosystems, Foster City, Calif.).

We claim:
1. A compound represented by formula (I);

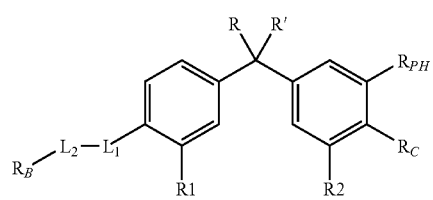

wherein;
R and R' are independently $C_1$-$C_5$ alkyl, or together R and R' form a saturated or unsaturated carbocyclic ring having from 3 to 8 carbon atoms;
$R_{PH}$ is hydrogen or methyl;
R1 and R2 are independently hydrogen, halo, or $C_1$-$C_5$ alkyl;
$L_1$ is —$(CH_2)_m$—O—;
$L_2$ is —$(CH_2)_m$CH(OH)— or —$(CH_2)_m$C(O)—;

where m is 0, 1 or 2, $R_B$ is a branched $C_3$-$C_5$ alkyl, $R_C$ is:
- —O—$SO_2$—(R50) where R50 is —$C_{1-3}$alkyl, or —$(CH_2)_{1-2}CF_3$;
- —NH—$SO_2$—(R50), where R50 is —$C_{1-3}$alkyl, —$CF_3$, or —$(CH_2)_{1-2}CF_3$;
- —N($CH_3$)—$SO_2$—$C_{1-2}$alkyl; or
- —N($SO_2R51)_2$ where each R51 is independently, —$C_{1-3}$ alkyl, —$CF_3$, or —$(CH_2)_{1-2}CF_3$.

2. A compound according to claim 1 wherein $R_{PH}$ is hydrogen.

3. A compound according to claim 1 represented by the structural formulae below as follows:

M-1)
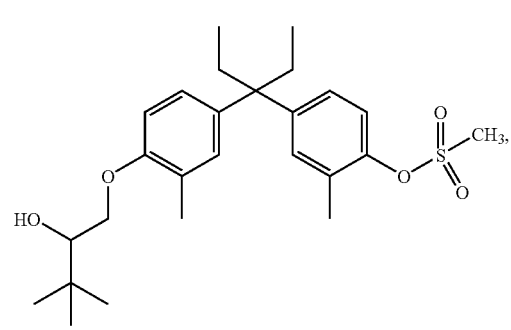

M-2)
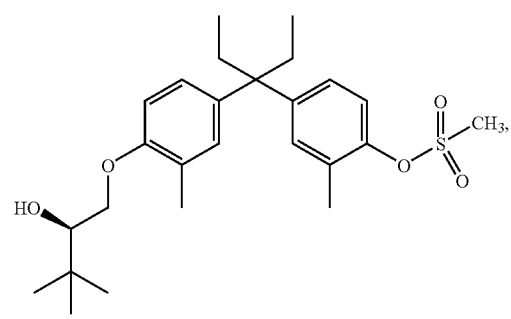

M-3)
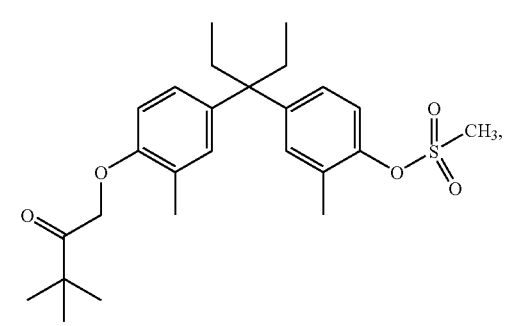

M-6)
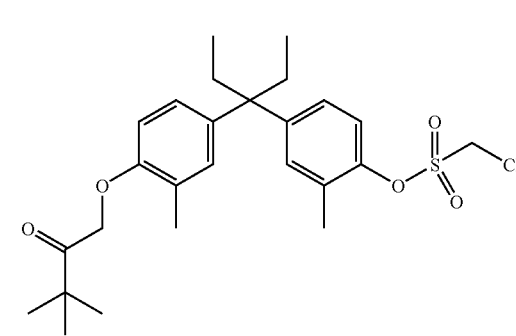

-continued

M-7)
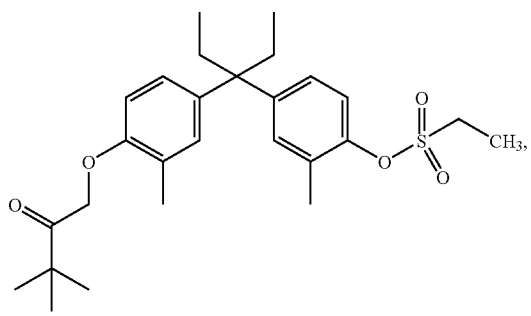

M-8)
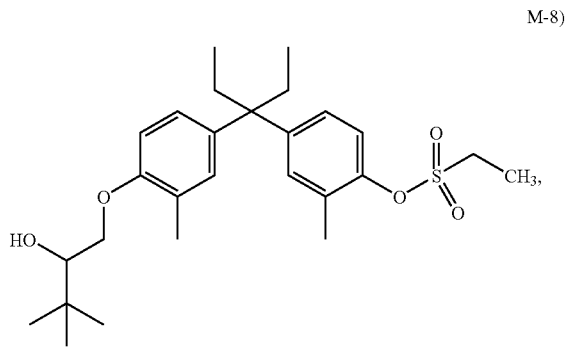

M-9)
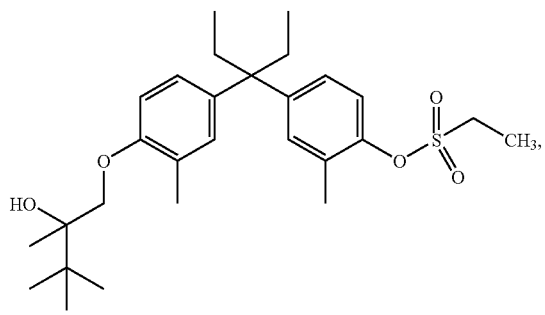

M-11)
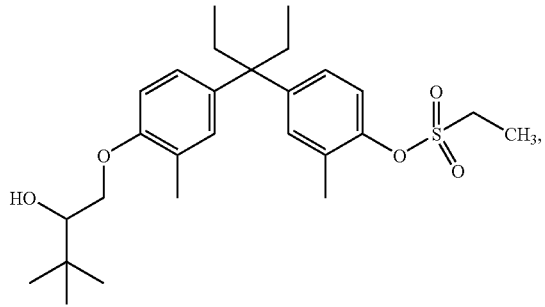

M-13)
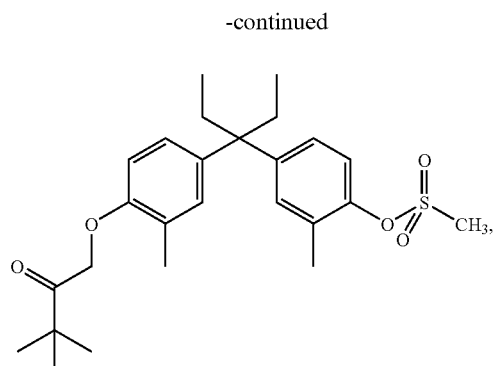
M-14)
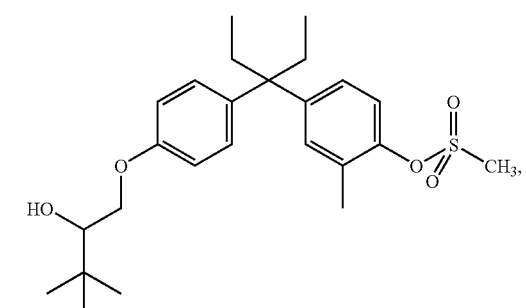
M-16)
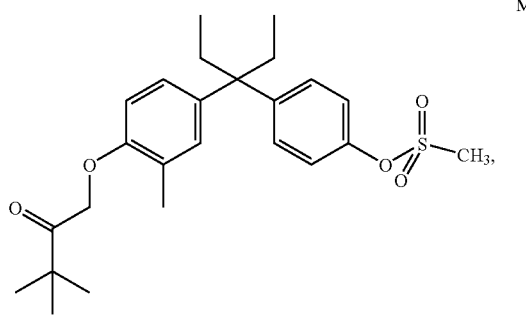
M-17)
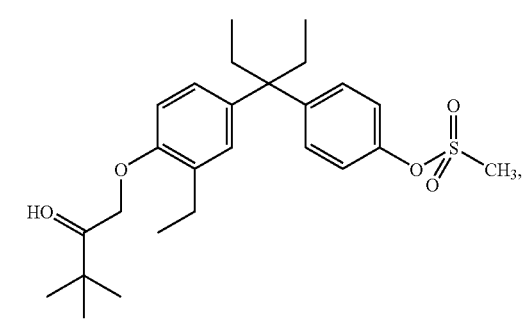
M-18)
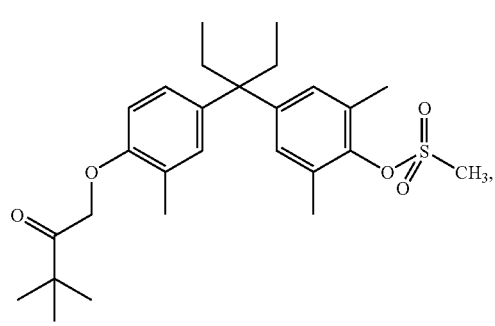
M-19)
M-20)
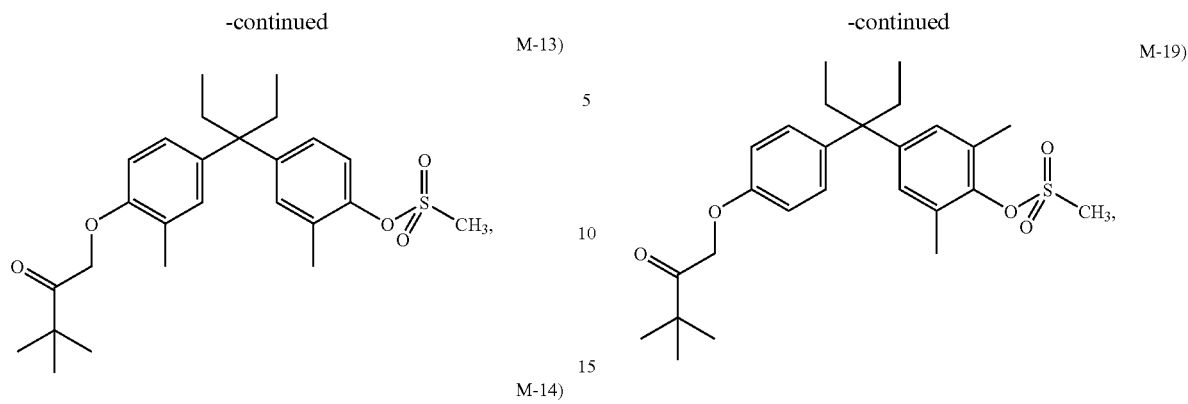
M-20)
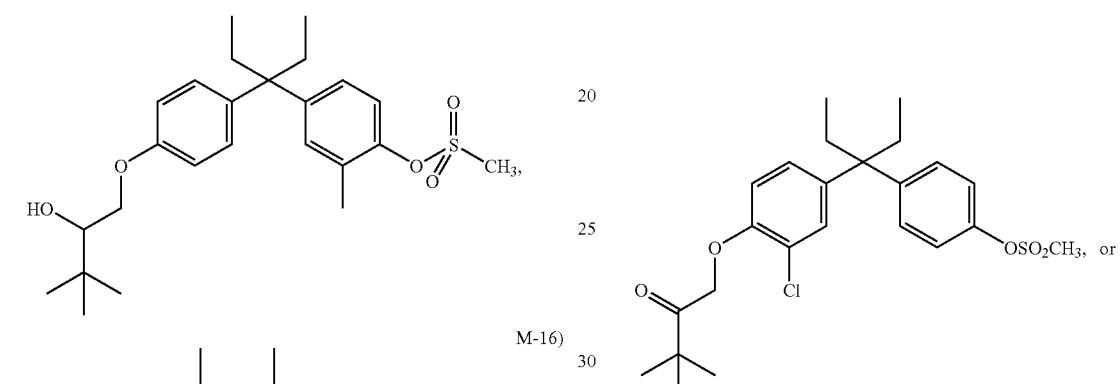
4. A compound represented by the structural formulae M-32 to M-50 as follows:
M-32)

M-34)
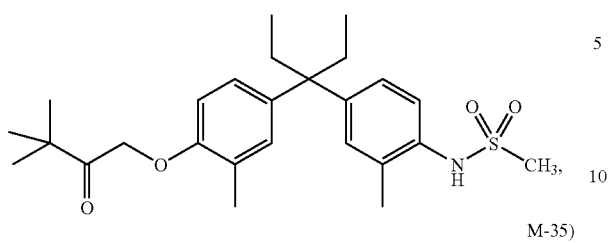
M-35)
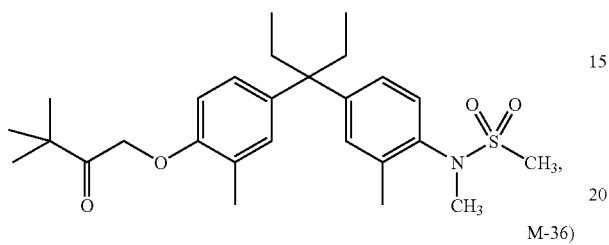
M-36)
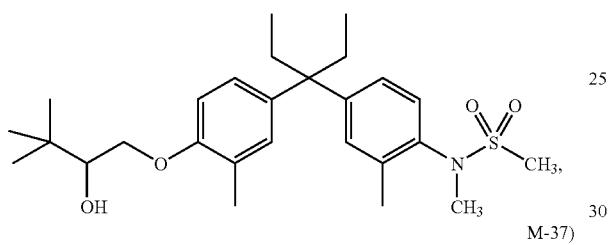
M-37)
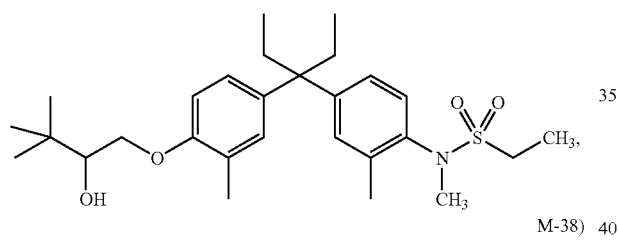
M-38)
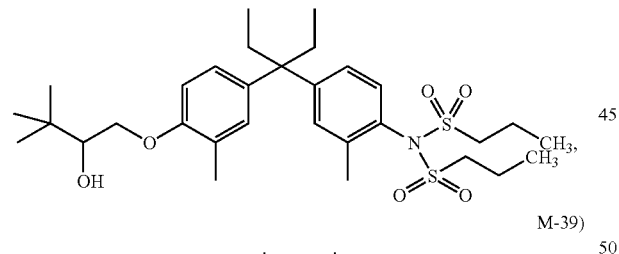
M-39)
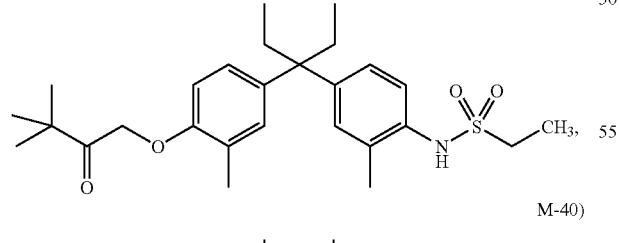
M-40)
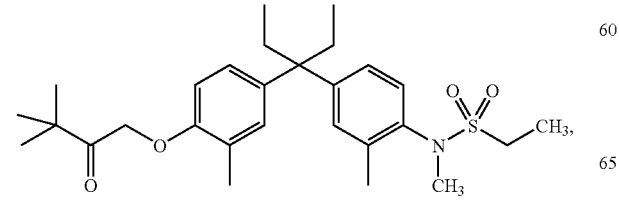
M-41)
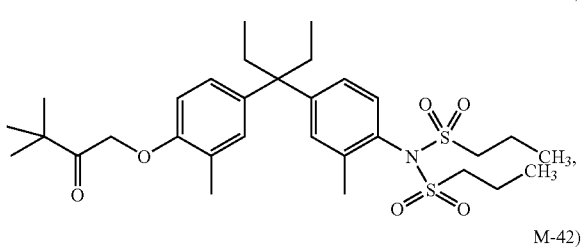
M-42)
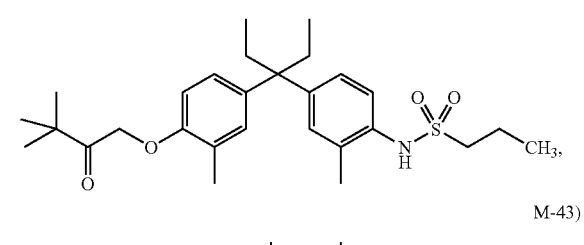
M-43)
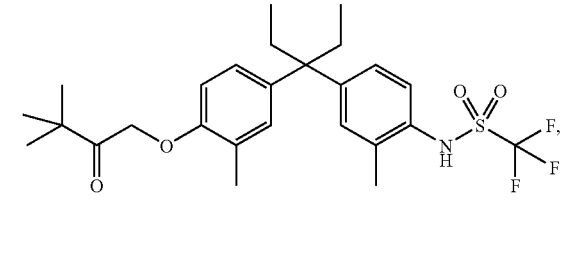
M-44)
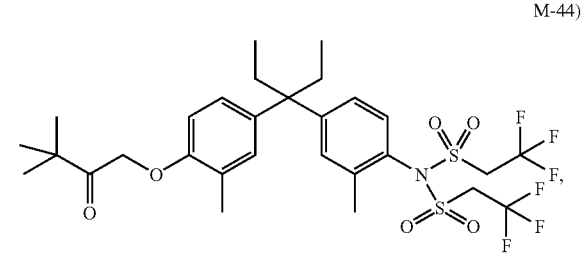
M-45)
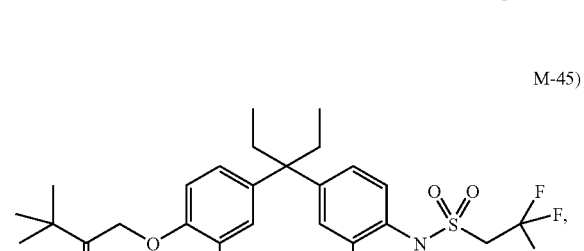
M-46)
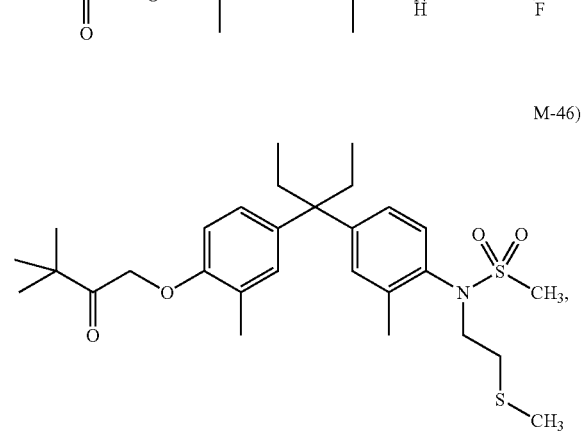

-continued

M-47)

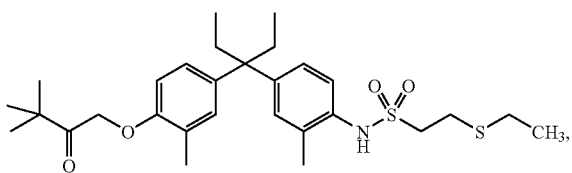

M-48)

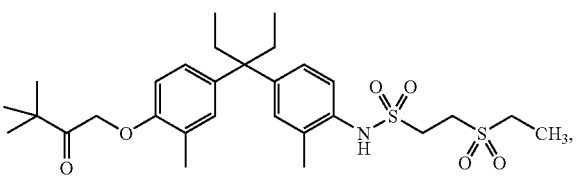

M-49)

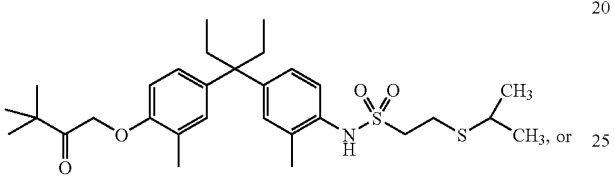

M-50)

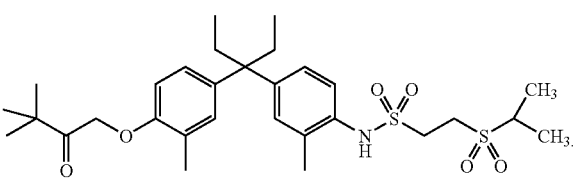

5. A compound represented by a formula below:

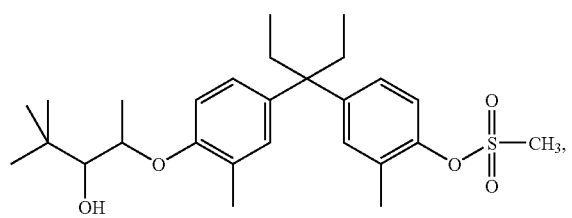

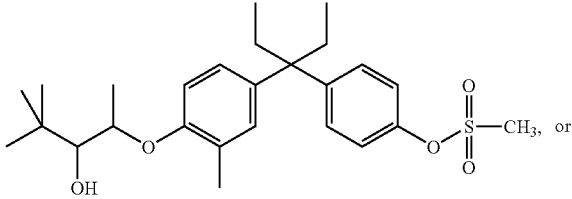

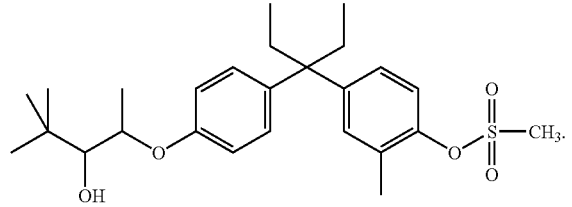

6. A pharmaceutical formulation comprising the compound according to claim 1 together with a pharmaceutically acceptable carrier or diluent.

7. A formulation for treating psoriasis comprising:
Ingredient (A2): the vitamin D receptor modulator of claim 1;
Ingredient (B2):
one or more co-agents that are conventional for treatment psoriasis selected from the group consisting of:
a. topical glucocorticoids,
b. salicylic acid,
c. crude coal tar; and
Ingredient (C2): optionally, a carrier or diluent.

8. A method of treating a mammal for Osteoporosis, Psoriasis, Scleroderma, or seborrheic dermatitis wherein the method comprises administering a pharmaceutically effective amount of at least one compound of claim 1.

9. The method of claim 8 for the treatment of psoriasis.

10. The method of claim 8 for the treatment of osteoporosis.

11. A compound represented by formula (II) or a pharmaceutically acceptable salt thereof:

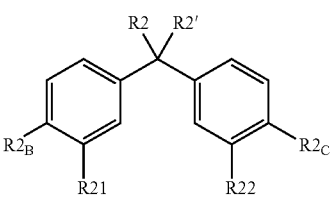

(II)

wherein;

R2 and R2' are independently methyl or ethyl;

R21 and R22 are independently selected from: hydrogen, methyl, ethyl, or —Cl, $R2_B$ is 3,3-dimethyl-2-hydroxybutoxy or 3,3-dimethyl-2-oxobutoxy; and $R2_C$ is

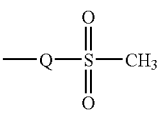

where Q is —O— or —NH—.

12. A compound represented by formula (III) or a pharmaceutically acceptable salt thereof:

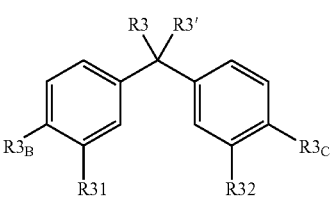

(III)

wherein;

R3 and R3' are independently methyl or ethyl;

R31 and R32 are independently selected from: hydrogen, methyl, ethyl, or —Cl,

R3$_B$ is 3,3-dimethyl-2-hydroxybutoxy or 3,3-dimethyl-2-oxobutoxy; and
R3$_C$ is

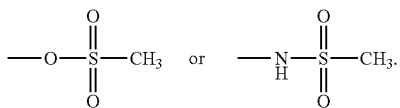

13. A compound represented by a formula below:

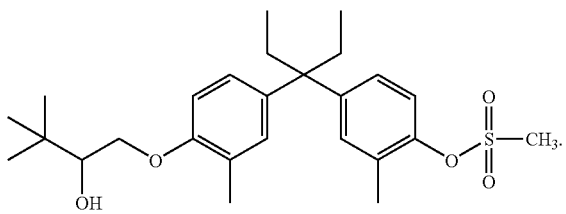

14. A compound represented by a formula below:

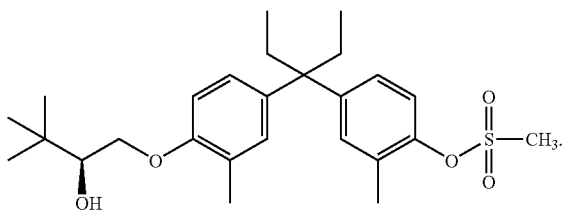

15. A compound represented by a formula below:

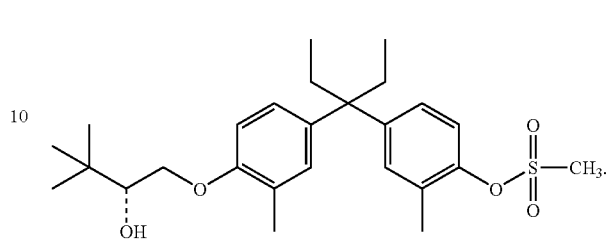

16. A pharmaceutical formulation comprising the compound according to one of claims 13, 14, or 15 together with a pharmaceutically acceptable carrier or diluent.

17. A method of treating a mammal for Osteoporosis, Psoriasis, Scleroderma, or seborrheic dermatitis wherein the method comprises administering a pharmaceutically effective amount of at least the compound of according to one of claims 13, 14, or 15.

18. The method of claim 17 for the treatment of psoriasis.

19. The method of claim 17 for the treatment of osteoporosis.

* * * * *

UNITED STATES PATENT AND TRADEMARK OFFICE
CERTIFICATE OF CORRECTION

PATENT NO.        : 7,750,184 B2
APPLICATION NO.   : 10/577967
DATED             : July 6, 2010
INVENTOR(S)       : Robert Peter Gajewski et al.

It is certified that error appears in the above-identified patent and that said Letters Patent is hereby corrected as shown below:

In the issued patent, please note the following corrections:

| S. No. | P/A | Original Page | Line | Issued Patent Column | Line | Description of Error |
|---|---|---|---|---|---|---|
| 1 | A | Sheet 2 of 2 List of References cited by applicant and considered by examiner (03/20/2009) | Entry 1 Line 2 (Non Patent Literature Documents) | First Page Col. 2 (Other Publications) | 23 | Delete "Kipogenesis" and insert -- Lipogenesis --, therefor. |
| 2 | P | Page 5 Claims (02/02/2010) | Claim 5 Line 2 (Structure M-15) | 137 | 30 (Approx.) | In Claim 3, after |

M-14)

" 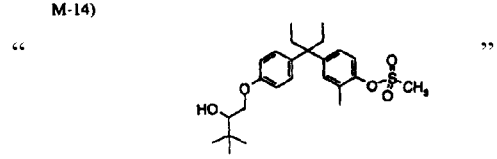 "

insert

M-15)

-- 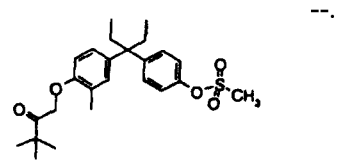 --.

Signed and Sealed this

Fourteenth Day of December, 2010

David J. Kappos
*Director of the United States Patent and Trademark Office*